United States Patent [19]
Sassanfar et al.

[11] Patent Number: 5,756,327
[45] Date of Patent: May 26, 1998

[54] RECOMBINANT MYCOBACTERIAL ISOLEUCYL-TRNA SYNTHETASE GENES, TESTER STRAINS AND ASSAYS

[75] Inventors: Mandana Sassanfar, Dedham; Paul R. Schimmel, Cambridge, both of Mass.

[73] Assignee: Cubist Pharmaceuticals, Inc., Cambridge, Mass.

[21] Appl. No.: 452,083

[22] Filed: May 26, 1995

Related U.S. Application Data

[63] Continuation-in-part of Ser. No. 305,765, Sep. 13, 1994, abandoned.
[51] Int. Cl.$^6$ .............................. C12N 9/00; C12N 5/00; C12N 15/00; C07H 21/04
[52] U.S. Cl. .................. 435/183; 435/240.1; 435/252.3; 435/320.1; 536/23.2
[58] Field of Search .................................. 435/69.1, 183, 435/240.1, 252.3, 320.1; 536/23.2

[56] References Cited

U.S. PATENT DOCUMENTS

| | | | |
|---|---|---|---|
| 4,713,337 | 12/1987 | Jasin et al. | 435/172.3 |
| 4,952,501 | 8/1990 | Jasin et al. | 435/69.2 |
| 4,963,487 | 10/1990 | Schimmel et al. | 435/172.3 |

FOREIGN PATENT DOCUMENTS

WO 95/09927  4/1995  WIPO.

OTHER PUBLICATIONS

Webster, T., et al., "Specific Sequence Homology and Three-Dimensional Structure of an Aminoacyl Transfer RNA Synthetase," *Science* 226:1315–1317, Dec. 1984.
Edwards, H., et al., "An *E. coli* Aminoacyl–tRNA Synthetase Can Substitute for Yeast Mitochondrial Enzyme Function In Vivo," *Cell* 51:643–649, Nov. 20, 1987.
Englisch, U., et al., "Structure of the Yeast Isoleucyl–tRNA Synthetase Gene (ILS1)," *Biol. Chem. Hoppe–Seyler* 368:971–979, Aug. 1987.
Martindale, D.W., et al., "Isolation and complete sequence of the yeast isoleucyl–tRNA synthetase gene (ILS1)," *Current Genetics* 15:99–106 (1989).
Jenal, U., et al., "Isoleucyl–tRNA Synthetase of *Methanobacterium thermautotrophicum* Marburg," *The Journal of Biological Chemistry* 266(16):10570–10577, Jun. 5, 1991.
Racher, K.I. et al., "Expression and Characterization of a Recombinant Yeast Isoleucyl–tRNA Synthetase," *The Journal of Biological Chemistry* 266(26):17158–17164, Sep. 15, 1991.
Csank, C., et al., Isoleucyl–tRNA Synthetase from the Ciliated Protozoan *Tetrahymena thermophila*, *The Journal of Biological Chemistry* 267(7):4592–4599, Mar. 5, 1992.
Shiba, K., et al., "Human cytoplasmic isoleucyl–tRNA synthetase: Selective divergence of the anticodon–binding domain and acquistion of a new structural unit," *Proc. Natl. Acad. Sci. USA*, 91:7435–7439, Aug. 1994.
von der Haar, F. et al, "Target Directed Drug Synthesis: The Aminoacyl–tRNA Synthetases as Possible Targets," *Angew. Chem. Int. Ed.*, 20(3):217–223 (1981).

Chalker, A.F., et al., "Analysis and Toxic Overexpression in *Escherichia coli* of a Staphylococcal Gene Encoding Isoleucyl–tRNA Synthetase," *Gene*, 141:103–108 (1994).
Hughes, J. and Mellows, G., "Interaction of Pseudomonic Acid A with *Escherichia coli* B Isoleucyl–tRNA Synthetase," *Biochem J.*, 191:209–219 (1980).
Weygand–Duraševi ć, I., et al., "Yeast Seryl–tRNA Synthetase Expressed in *Escherichia coli* Recognizes Bacterial Serine–Specific tRNAS in vivo," *Eur. J. Biochem.* 214:869–877 (1993).
Walter, R. D. and Kuhlow, F., "Parasite–Specific Interaction of N–[4–(4' Nitroanilino)–Phenyl]– S–(β–Carboxyethyl)–Dithiocarbamic Acid–Ester with Arginyl–tRNA–Synthetase from *Dirofilaria immitis*," *Trop. Med. Parasit.* 36:230–232 (1985).
Shepard, A., et al., "RNA Binding Determinant in Some Class I tRNA Synthetases Identified by Alignment–Guided Mutagenesids," *Proc. Natl. Acad. Sci. USA*, 89:9964–9968 (1992).
Shiba, K. and Shimmel, P., "Functional Assembly of a Randomly Cleaved Protein," *Proc. Natl. Acad. Sci. USA*, 89:1880–1884 (1992).
Iaccarino, M. and Berg, P., "Isoleucine Auxotrophy as a Consequence of a Mutationally Altered Isoleucyl–Transfer Ribonucleic Acid Synthetase," *J. Bacteriol.*, 105:527–537 (1970).
Meinnel, T., et al., "Aminoacyl–tRNA Synthetases: Occurrence, Structure, and Function." In tRNA: *Structure, Biosynthesis, and Function*, Söll, D. and RajBhandary, U., eds. (Washington, DC: American Society for Microbiology), pp. 251–300 (1995).

(List continued on next page.)

*Primary Examiner*—Robert A. Wax
*Assistant Examiner*—Lisa J. Hobbs
*Attorney, Agent, or Firm*—Hamilton, Brook, Smith & Reynolds, P.C.

[57] ABSTRACT

Isolated and/or recombinant nucleic acids encoding mycobacterial isoleucyl-tRNA synthetase have been characterized. Recombinant DNA constructs and vectors having a sequence which encodes mycobacterial isoleucyl-tRNA synthetase have been made, and can be used for the construction of tester strains as well as for the production of isolated and/or recombinant isoleucyl-tRNA synthetases. These enzymes or portions thereof are useful in the biochemical separation of isoleucine and quantification of isoleucine or ATP, and for producing antibodies useful in the purification and study of the enzyme, for example. Host cells and methods useful for producing recombinant mycobacterial isoleucyl-tRNA synthetases are described, as are tester strains, which are cells engineered to rely on the function of the tRNA synthetase encoded by an introduced cloned gene. Tester strains can be used to identify inhibitors of the essential tRNA synthetase enzyme encoded by the introduced cloned gene, and thus provide a means to assess the antimicrobial effect and specificity of the inhibitor without employing slow-growing, pathogenic strains of mycobacteria, such as *Mycobacterium tuberculosis*.

28 Claims, 25 Drawing Sheets

OTHER PUBLICATIONS

Jasin, M. and Schimmel, P., "Deletion of an Essential Gene in *Escherichia coli* by Site-Specific Recombinatin with Linear DNA Fragments," *J. Bacteriol.* 159(2):783–786 (1984).

Edwards, H. and Schimmel, P., "A Bacterial Amber Suppressor in *Saccharomyces cerevisiae* Is Selectively Recognized by a Bacterial Aminoacyl–tRNA Synthetase," *Molecular and Cellular Biology*, 10(4):1633–1642 (1990).

Shiba, K., et al., "Isolation of Higher Eukaryote Aminoacyl–tRNA Synthetase Genes by an Alignment–Guided Cross–Species PCR: Application to Human Isoleucine tRNA Synthetase," [From *Programme and Abstracts*, p. F.46], 15th International tRNA Workshop, Société Francaise de Biochimie et Biologie Moléculaire, Cap d'Agde, France, May–Jun. 4 (1993), Abstract No.364.

Printout of a computer record of parts of a poster presented at Cap d'Agde, France, May 30–Jun. 4, 1993, 15th International tRNA Workshop, Société Francaise de Biochimie et Biologie Moléculaire.

Sequence of Human Isoleucyl–tRNA Synthetase Gene, GenBank Name: HSU04953, Accession: U04953, National Center for Biotechnology Information Seq ID: 450850. Entered by Nichols, R.C., et al. First Available: Jan. 13, 1994; Undated: Jan. 26, 1994.

Hughes, J., et al., "Inhibition of Isoleucyl–Transfer Ribonucleic Acid Synthetase in *Echerichia coli* by Pseudomonic Acid," *Biochem. J.* 176:305–318 (1978), Great Britain.

Deobagkar, D. N. and Gopinathan, K. P., "Studies on Transfer RNA from Mycobacteria," *Can. J. Microbiol.*, 24:693–702 (1978).

Natarajan, V., and Gopinathan, K. P., "Mechanism of Aminoacylation of tRNA: Influence of Spermine on the Kinetics of Aminoacyl–tRNA Synthesis by Isoleucyl– and Valyl––tRNA Synthetases from *Mycobacterium smegmatis*," *Biochimica et Biophysica Acta.* 654:94–101 (1981).

Hou, Y–M., et al., "Sequence Determination and Modeling of Structural Motifs for the Smallest Monomeric Aminoacyl–tRNA Synthetase," *Proc. Natl. Acad. Sci.*, 88:976–980 (1991).

Heck, J. D., and Hatfield, G. W., "Valyl–tRNA Synthetase Gene of *Escherichia coli* K12, Primary Structure and Homology Within Family of Aminoacyl–tRNA Synthetases," *The Journal of Biological Chemistry* 263(2):868–877 (1988).

Laske, R., et al., "Untersuchungen zum Wirkmechanismus antimykobakterieller Benzylamine," *Arch. Pharm. (Weinheim)*, 322:297–299 (1989).

Gopinathan, K. P., "Molecular Biology of Mycobacteria and Mycobacteriophages," *J. Indian. Sci.*, 73:31–45 (1993).

Natarajan, V., and Gopinathan, K. P., "Stimulation of Valyl–and Isoleucyl–tRNA Synthase Reactions by Polyamines," *J. Biosci.*, 1(4):357–367 (1979).

Lazard et al. (1985) Biochemistry 24:5099–5106.

Nichols et al. (1995) Gene 155: 299–304.

```
         Nde I
TTGGCGTCGAGTCGTCACCAGATCAGCTCTTGGATCGACGGCTACGGAGACGGACCAACTCGGTTCAGTCCATATGTGCTCGTTTTGA
AACGCCGACTCAGCAGTGGTCGGAGAACCTAGCTGCCGATGCCTGCTGGTTGAGCCAAGTCAGGTATACACGAGCAAAACT   86

Bsg I
                                                       BspH I
TTTCCGTCCTCCGCTTGCAACTCCGTCTAGGAGGTCAGATCATGACGCGCTGCTCTGCACAATGACGTAGTAACCGTAGCTTCGGCCC
AAAGGCAGGAGGCGAACGTTGAGGCAGATCCTCCAGTCTAGTACTGCGCGACGAGACGTGTTACTGCATCATTGGCATCGAAGCCGGG  172

Xcm I                                                              NgoA IV
                                                                           Nae I
CCAAGCTGCGGGTGGTGCGGGATGTGCCCCGGCCCCCGCGTCCAAGAAGGTTGCTCGCCGGCTCGANGNGCAGCCTTTCGGCACC
GGTTCGACGCCCACCACGCCCTACACGGGGCCGGGGGCGCAGGTTCTTCCAACGAGCGGCCGAGCTNCNCGTCGGAAAGCCGTGG   258
```

FIG. 5B

```
GGAGGGGACCCGCTGGTCGACGGGCAGCTCGTTTGCTGAGCATTCCGCTGCCGCCACCTCTACGCCGGTTGTGGCGTCGGGCT
         |        |        |        |        |        |        |        |
        Drd I    Sca I                Bpu 1102 I                                    344
        Sal I                         Esp I
                                      BsaM I
                                      Bsm I

CCTCCCCTGGGCAGCCTGCCCGTCGAGCAAACGACTCGTAAGGCACGCCGGTGAGATGCCGCAACACCGCGCAGCCCGA
         |        |        |        |        |        |        |        |
                                                                                    430

GCTCGAGGTCCAGGTCCTAGTCCCGATGGGCAGCAGGCCGACCTTGCCGCCGATGTGTGGATTTGCCGCGATCGTGGGCTGGGCGACAATCCCGTA
         |        |        |        |        |        |        |        |
        Xho I    Stu I                                                   Eco52 I
        Sci I                                                            Xma III
                                                                         Sfi I
                                                                         Bgl I

CGAGCTCCAGGTCCGGATCAGGTCCGGCTACCGTCGGCTGGAACGCGACCCGCTGTTAGGGCAT
         |        |        |        |        |        |
                          Cla I                                         Bce83 I

GAATCAGGGGAACGGCATCGATCCGGCGATCACCGGGGAGCCTTCGGAAGAACGGCCGGTTAGGCCAGTAGAACCGAACGGGTTGG
         |        |        |        |        |        |        |        |
                                                                                    516

CTTAGTCCCCTTGCCGTAGCTAGGCCGCTAGTGGCCCTTCTTGCCGGCCAATCCGGTCATTCTTGGCTTGCCCAACC
         |        |        |        |        |        |        |
```

```
AACGATGCCTGCCGCGCATCCGTGTTGCGCTACACCGACGAGTGGCAGGGCGTATGTAACTCGGCAAGCTCGCTGGGTCGACTTCGA   1118
     |         |         |         |         |         |         |         |
TTGCTACGGACGGCGCGTAGGCACAACGCGATGTGGCTGCTCACCGTCCGCATACATTGAGCCGTTCGAGCGACCCAGCTGAAGCT
                                                                          |——Sal I
  N   D   A   C   R   A   S   V   L   R   Y   T   D   E   W   Q   A   Y   V   T   R   Q   A   R   W   V   D   F   D

CAACGATTACAAGACGCTCGATCTGGCTTACATGGAGTCGGTGATTTGGGCCTTCAAACAGTTGTGGGACAAGGGCCTGGCCTACG   1204
     |         |         |         |         |         |         |         |
GTTGCTAATGTTCTGCGAGCTAGACCGAATGTACCTCAGCCACTAAACCCGGAAGTTTGTCAACACCCTGTTCCCGGACCGGATGC
                                       |——Rle A I
  N   D   Y   K   T   L   D   L   A   Y   M   E   S   V   I   W   A   F   K   Q   L   W   D   K   G   L   A   Y

AGGGCTACCGGGTGCTGCCGTACTGCTGGCGGGACGAGACGCCGCTGTCGAATCACGAACTCCGCATGGACGACGACGTCTACCAA   1290
     |         |         |         |         |         |         |         |
TCCCGATGGCCCACGACGGCATGACGACCGCCCTGCTCTGCGGCGACAGCTTAGTGCTTGAGCGTACCTGCTGCTGCAGATGGTT
                                                              |——Drd I
                                                              |——Tth111 I
                                                                |——Aat II
  E   G   Y   R   V   L   P   Y   C   W   R   D   E   T   P   L   S   N   H   E   L   R   M   D   D   D   V   Y   Q
```

FIG. 5F

```
AGCCCGCCAAGATCCCGCGGTAACGGTGGGCTTCAAGGTGGTGGGCCAACCGGTGGCCAACCAGACAACGGGCTAGACGGTGCCTACTTGCTGGT  1376
TCGGGCGGTTCTAGGGCGCCATTGCCAAGTTCCACCACCCGAAGTTCCACCACCCGTTGGCCGATCGCCACGATGAACGACCA
 S  R  Q  D  P  A  V  T  V  G  F  K  V  V  G  G  Q  P  D  N  G  L  D  G  A  Y  L  L  V

GTGGACGACTCCGTGAGGACCTCGCTGTCGAACCTCGCCGTCAGTTGCGGTAAGCCCGGACATCACCTACGTACAGGTCCAGGCGGGCG  1462
CACCTGCTGAGGCACTCCTGGAGCGACAGCTTGGAGCGGCAGTCAACGCCATTCGGGCCTGTAGTGGATGCATGTCCAGGTCCGCCCGC
 W  T  T  P  W  T  L  P  S  N  L  A  V  A  V  S  P  D  I  T  Y  V  Q  V  Q  A  G

ATCGCCCGTTTCGTACTGGCCGAGGCACGGCTGGCCCGCTTACGCCGGTGAAGAGCCCGTTGGTGCTCGGCACCTATCGC  1548
TAGCGGGCAAAGCATGACCGGCTCCGTGCCGACCGGGCGAATGCGGCCACTTCTCGGGCAACCACGAGCCGTGGATAGCG
 D  R  R  F  V  L  A  E  A  R  L  A  R  Y  A  R  E  L  G  E  E  P  V  L  G  T  Y  R
```

Mlu113 I, Ksp I, Sac II, Sst II, Bal I, MluN I, Drd I, SnaB I, Afa22M I, Pvu I, Sgf I, Ear I, Ksp632 I, Sap I

FIG. 5G

```
          Kas I
          Nar I
          Ehe I
          Bbe I
                                                         BspM I                                                                              Nhe I
GGCGCCGAACTGCTGGGCACCCGCTACCTGCCGCCGTTTGCCTATTTCATGGACTGGCCCAACGCTTTTCAGGTGCTAGCAGGCGA
CCGCGGCTTGACGACCCGTGGGCGATGGACGGCGGCAAACGGATAAAGTACCTGACCGGGTTGCGAAAGTCCACGATCGTCCGCT       1634
  G  A  E  L  L  G  T  R  Y  L  P  P  F  A  Y  F  M  D  W  P  N  A  F  Q  V  L  A  G  D

Taq II                   Nde I                               Drd I
CTTTGTAACGACCGACGATGGCACCGGCATCGTGCATATGGCACCGGCCTATGGTGAGGACGACATGGTGGTCGCGGAGGCGGTCG
GAAACATTGCTGGCTGCTACCGTGGCCGTAGCACGTAGTATACCGTGGCCGGATACCACTCCTGCTGTACCACCAGCGCCTCCGCCAGC      1720
  F  V  T  T  D  D  G  T  G  I  V  H  M  A  P  A  Y  G  E  D  D  M  V  V  A  E  A  V

SgrA I                PshA I
                                Sal I                                                 Aat II
GTATCGGCCGCCGGTGACTCCGGTCGACTCCAAGGGACGCTTCGACGTCGCCGATTACCAGCATGTCTTTGACGCC
CATAGCCGGCGGCCACTGAGGCCAGCTGAGGTTCCCTGCGAAGCTGCAGCGGCTAATGGTTCCCGTCTACAGAAACTGCGG     1806
  G  I  A  P  V  T  P  V  D  S  K  G  R  F  D  V  T  V  A  D  Y  Q  H  V  F  D  A
```

FIG. 5H

```
         Bps I
         Bpu10 I
         Bsc91 I
AACGCGGCAGATCGTCCGGGACCTGAAGACCCAGAGCGGCCCTGCGGGTGAATGGCCCAGTGTTGATTCGTCACGAAACCTACGA  1892
TTGCGCCGTCTAGCAGGCCCTGGACTTCTGGGTCTCGCCGGGACGCCCACTTACCGGGTCACAACTAAGCAGTGCTTTGGATGCT
 N  A  Q  I  V  R  D  L  K  T  Q  S  G  P  A  A  V  N  G  P  V  L  I  R  H  E  T  Y  E
                                         Eco57 I

BstX I         RleA I              Age I
                                            PinA I
GCACCCTTACCCACACTGCTGCCGATGCCGCTAACCCGCTGATCTACCGGTCGGTTCGTGTTCGTCAGGGTGACGGACTTCC    1978
CGTGGGAATGGGTGTGACGACGGCTACGGCGATTGGGCGACTAGATGGCCAGCAGCAAGCAGTCCCACTGCCTGAAGG
 H  P  Y  P  H  C  W  R  C  R  N  P  L  I  Y  R  S  V  S  S  W  F  V  R  V  T  D  F
                                                                            Bsa I

PmaC I                                                             Pst I
         Eco72 I                                                            Kas I
                                                                            Nar I
                                                                            Ehe I
GAGACCCGGCATGGTGGAGCTAAACCAGCAGATCACGTGGTATCCCGAACACGTCAAGGACGGCTTCGGCAAGTGGCTGCAGGGC  2064
CTCTGGGCCGTACCACCTCGATTGGTCGTCTAGTGCACCATAGGGCTTGTGCAGTTCCTGCCGAAGCCGTTCACCGACGTCCCG
 R  D  R  M  V  E  L  N  Q  Q  I  T  W  Y  P  E  H  V  K  D  G  F  G  K  W  L  Q  G
                                            Bgl I
```

FIG. 5I

```
          Bbe I
          ┌──
GCCCGCGATTGGTCGATCTCCCGGAATCGTCCCCGATTCCGGTATGGAAGTCCGACGACCCGGCCTACCCGCGCAT
     ─────┼─────────┼─────────┼─────────┼─────────┼─────────┼─────────┼──
CGGGCGCTAACCAGCTAGAGGGCCTTAGCAGGGCCTATAGAGGGCTAAGGCCTATTGGGCCGGATGGGCGCGTA
                                                                        2150
                                                                        ─────
                                                                        Cla I
 A  R  D  W  S  I  S  R  N  R  Y  W  G  T  P  I  P  V  W  K  S  D  D  P  A  Y  P  R  I
```

```
                                  BsiW I
                                   Spl I
                                    Sun I
                                     Bpm I
                                      Gsu I                      Ecl136 II
                                                                  EcoICR I
                                                                   Sac I
                                                                    Sst I
CGATGTCTACGGCAGCCTCGACGAGCTTCGGCCGTACGCCCGGCCCAATTTGCACCGGCCCTACATCGACGAGCTCA
 ───┼─────────┼─────────┼─────────┼─────────┼─────────┼─────────┼─────────┼──
GCTACAGATGCCGTCGGAGCTGCTCGAAGCCGGCATGCGGGCCGGGTTAAACGTGGCCGGGATGTAGCTGCTCGAGT
                                                                            2236
 D  V  Y  G  S  L  D  E  L  E  R  D  F  G  V  R  P  A  N  L  H  R  P  Y  I  D  E  L
```

```
                                         BsmI
                                         BsaMI
CCCGTCCCAACCCAGACGATCCGACTGGGCCGCATTCCCGATGTGCTCGACGTGTTCGACTCGGGATCC
 ────┼─────────┼─────────┼─────────┼─────────┼─────────┼─────────┼──
GGGCAGGGTTGGGTCTGCTAGGCTGACCCGGCGTAAGGGCTACACGAGCTGCACAAGCTGAGCCCTAGG
                                                                  2322
                                                                  ─────
                                                                  Bam HI
 T  R  P  N  P  D  D  P  T  G  R  S  T  M  R  R  I  P  D  V  L  D  V  W  F  D  S  G  S
```

FIG. 5J

```
ATGCCGTATGCCCAGGTGCACTACCCGTTCGAGAACCTGGATTGGTTCCAGGGACACTACCCGGGCGACTTCATCGTCGAGTACAT  2408
TACGGCATACGGGTCCACGTGATGGGCAAGCTCTTGGACCTAACCAAGGTCCCTGTGATGGGCCGCTGAAGTAGCAGCTCATGTA
  M  P  Y  A  Q  V  H  Y  P  F  E  N  L  D  W  F  Q  G  H  Y  P  G  D  F  I  V  E  Y  I

CGGGCAGACCCGTGGTTTTACACACTGCATGTGTTGGCGCCGCTCTTTGACCGCCGGCCATTCAAAACCTGTGTGGCGC  2494
GCCCGTCTGGGCACCAAAATGTGTGACGTACACAACCGCGGCGAGAAACTGGCGGCCGGTAAGTTTGGACACACCGCG
  G  Q  T  R  G  W  F  Y  T  L  H  V  L  A  T  A  L  F  D  R  P  A  F  K  T  C  V  A

ATGGGGATTGTCCTTGGTTTCGATGGCCAGAAGATGAGCAAGAGTCGGTTGCGCAACTATCCAGACGTAACAGAGGTGTTCGATCGCGAC  2580
TACCCTAACAGGAACCAAAGCTACCGGTCTTCTACTCGTTCTCAGCCAACGCGTTGATAGGTCTGCATTGTCTCCACAAGCTAGCGCTG
  H  G  I  V  L  G  F  D  G  Q  K  M  S  K  S  V  R  N  Y  P  D  V  T  E  V  F  D  R  D
```

FIG. 5K

```
                                                    EcoR I        Nru I
GGCTCCGACGCCATGCGGTGGTTCCTGATGGCATCGCCGATTCTGCGCGGGGGCAACCTGATCGTCACTGAGCAAGGAATTCGCGA   2666
CCGAGGCTGCGGTACGCCACCAAGGACTACCGTAGCGGCTAAGACGCGCCCCGTTGGACTAGCAGTGACTCGTTCCTTAAGCGCT
 G  S  D  A  M  R  W  F  L  M  A  S  P  I  L  R  G  G  N  L  I  V  T  E  Q  G  I  R  D
PflM I
Van91 I

Acc65 I
                                                              Asp 718
                                                              Kpn I
CGGTGTGGACAAGTCCTGTGCCCCTGTGTGGAACACCTACAGCTTCCTGGCGCTGTATGCACCGAAAGTCGGTACCTGGCGCGTCG   2752
GCCACACCTGTTCAGGACACGGGGACACACCTTGTGGATGTCGAAGGACCGCGACATACGTGGCTTTCAGCCATGGACCGCGCAGC
 G  V  R  Q  V  L  L  P  L  W  N  T  Y  S  F  L  A  L  Y  A  P  K  V  G  T  W  R  V
                     Eco72 I           Ball          Bgl I
                     Pmac I            MluN I
                     Apa L I
ATTCGGTGCACGTGCTGGATCGCTATATCCTGGCCAAGCTGGCCGAGTCGATGAAGTTTACGAT   2838
TAAGCCACGTGCACGACCTAGCGATATAGGACCGGTTCGACCGGCTCAGCTACTTCAAATGCTA
 D  S  V  H  V  L  D  R  Y  I  L  A  K  L  A  V  L  R  D  D  L  S  E  S  M  E  V  Y  D
```

FIG. 5L

```
ATTCCCGGTGCCTGTGAACATTTGCGTTGACTAATTGGTATGTGCCGACGGTTCGCGTTCTGGGC  2924
TAAGGGCCACGGACACTTGTAAACGCAACTGATTAACCATACACGGCTGCCAAGCGCAAGACCCG
 I  P  G  A  C  E  H  L  R  Q  F  T  E  A  L  T  N  W  Y  V  R  R  S  R  F  W  A

Bps I
           Bpu10 I
           Bsc91 I
                            Dra III    BstE II    Bsi I    BstX I            Bcl I
AGAAGACGCCGATGCCATCGACACGCTACACACCGTGTTGGAGGTGACCACGAGGCTGGCCGCCCCGCTGCTTCCGCTGATCACCG  3010
TCTTCTGCGGCTACGGTAGCTGTGCGATGTGTGGCACAACCTCCACTGGTGCTCCGACCGGCGGGGCGACGAAGGCGACTAGTGGC
 E  D  A  D  A  I  D  T  L  H  T  V  L  E  V  T  T  R  L  A  A  P  L  L  P  L  I  T

Afa22M I
                         Pvu I       Bal I
                         Apa L I     Mlu N I         Bsp M I    Sex A I
AGATAATCTGGGCGTGGTCTGACGACGGATCGGTTGCGCACTTGACGGTGCACCTGACCTGCTGCCAGCGCCCAGCTGGATGCCGAC  3096
TCTATTAGACCGCACCAGACTGCTGCCTAGCCAACGCGTGAACTGCCACGTGGACTGGACGACGGTCGCGGGTCGACCTACGGCTG
 E  I  I  W  R  G  L  T  R  E  R  S  V  H  L  T  D  W  P  A  P  D  L  L  P  S  D  A  D
```

FIG. 5N

```
GATGTGCAGGCCGCCATCAAGGCGGTCAAGGCCGGGGACGGCGTCATAAACCCGGACGGCACCTTGTTGGGCCCCGCGGTGCT
                                                                                    3440
CTACACGTCCGGCGGGTAGTTCCGGCCAGTTCCGCGCCGTGCTGCCAGTATTTGGGCCTGCCGTGGAACAACCGCGGCGCCACGA
 D  V  Q  A  A  I  K  A  V  K  A  G  D  G  V  I  N  P  D  G  T  L  L  A  G  P  A  V  L
```

```
GACGCCCGACGAGTACAACTCCCGGCTGGTCGCCGCCGACCCGGAGTCCACCGCCGCCCTGCCCGACGGGGCGGGGCTGGTCGTTC
                                                                                    3526
CTGCGGGCTGCTCATGTTGAGGGCCGACCAGCGGCGGCTGGGCCTCAGGTGGCGCGGGACGGGCTGCCCCGCCCCGACCAGCAAG
 T  P  D  E  Y  N  S  R  L  V  A  A  D  P  E  S  T  A  A  L  P  D  G  A  G  L  V  V
```

```
TGGATGGCACCGTCACTGCCGCCGAACTCGAAGCCGAGGGCTGGGCCAAAGATCCGATCCGCGAAGAGCTGCGTAAGTCGACC
                                                                                    3612
ACCTACCGTGGCAGTGACGGCGGCTTGAGCTTCGGCTCCCGACCCGGTTTCTAGGCTTGAGCGCTTAGGGCGCATTCAGCTGG
 L  D  G  T  V  T  A  E  L  E  A  E  G  W  A  K  D  P  I  R  E  L  R  K  S  T
```

FIG. 10
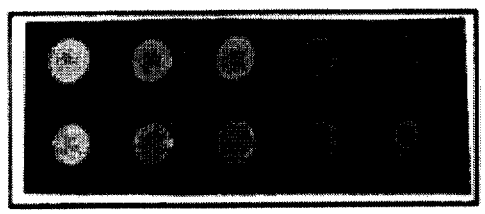
16 Hours, LB agar — 37°C
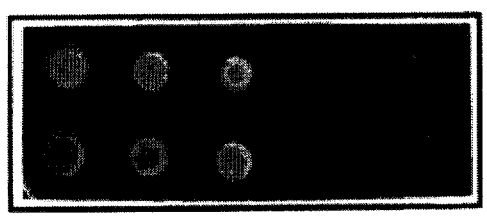
30°C
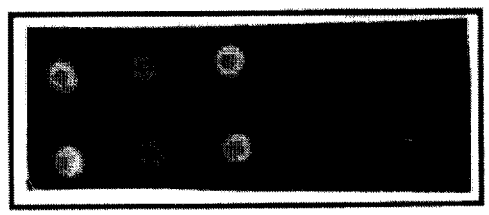
37°C
42°C
72 Hours, M9 agar

RECOMBINANT MYCOBACTERIAL ISOLEUCYL-TRNA SYNTHETASE GENES, TESTER STRAINS AND ASSAYS

RELATED APPLICATIONS

This application is a continuation-in-part of U.S. Ser. Number 08/305,765, filed Sep. 13, 1994, now abandoned, the teachings of which are incorporated herein by reference in their entirety.

BACKGROUND OF THE INVENTION

Mycobacteria are slow-growing aerobic bacteria characterized by their surface glycolipids, and by the high G-C content of their DNA (>63%). Organisms of the genus Mycobacterium include more than 30 well-characterized members and many that are as yet unclassified. Most are not pathogenic for humans, but among the mycobacteria are the etiologic agents for leprosy (*M. leprae*) and for tuberculosis (*M. tuberculosis*), the leading cause of death in the world from an infectious disease (Bloom, B. R. and C. J. L. Murray, *Science*, 257:1055–1064 (1992)).

It has been estimated that as much as one-third of the population of the world is infected with *M. tuberculosis*. Tuberculosis (TB) is responsible for about one in four avoidable adult deaths in developing countries (Murray, C. J. L. et al., 1993, In: *Disease Control Priorities in Developing Countries*, D. T. Jamison et al., Eds. (Oxford Univ. Press, New York) pp. 233–259). Since the 1980s the number of new cases of TB infections has steadily increased both in the US and in Europe. Individuals infected with the human immunodeficiency virus (HIV) are particularly susceptible to infection with *M. tuberculosis*, a growing problem that threatens the control of the spread of tuberculosis.

Infection caused by drug-sensitive strains of *M. tuberculosis* has been successfully treated by using a combination of isoniazid, rifampicin and pyrazinamide. However, in cities worldwide, the emergence of multidrug resistant isolates of *M. tuberculosis* is becoming alarming. The fatality rate for drug-resistant TB is 50%. According to the World Health Organization, almost 20% of the isolates tested in New York City in 1992 were resistant to both isoniazid and rifampicin.

It would be a great advantage in the control of diseases caused by the Mycobacteria to expand the number of target molecules whose function could be inhibited by antibiotic agents.

SUMMARY OF THE INVENTION

The invention relates to isolated and/or recombinant nucleic acids which encode isoleucyl-tRNA (Ile tRNA) synthetases (IleRSs) of mycobacterial origin. The invention also relates to recombinant DNA constructs and vectors containing DNA having a sequence which encodes a isoleucyl-tRNA synthetase of mycobacterial origin, or portions of the enzyme. These nucleic acids and DNA constructs can be used to produce recombinant isoleucyl-tRNA synthetase of mycobacterial origin.

A further embodiment of the invention is antisense nucleic acid which can hybridize to the nucleic acid which encodes the isoleucyl-tRNA synthetase of mycobacteria. In cells, antisense nucleic acid can inhibit the function of an RNA which encodes the isoleucyl-tRNA synthetase of mycobacteria.

The invention also relates to proteins or polypeptides, referred to herein as isolated, recombinant mycobacterial isoleucyl-tRNA synthetases. These enzymes are useful in biochemical separation of isoleucine and quantitations of isoleucine and ATP. Antibodies which bind to these enzymes can be made and can be used in the purification and study of the enzyme.

The recombinant mycobacterial isoleucyl-tRNA synthetases can be produced in host cells using cells and methods described herein. Tester strains, which are cells engineered to rely on the function of the tRNA synthetase encoded by an introduced cloned gene, are also an embodiment of the invention. Tester strains can be used to test the effectiveness of drug candidates in the inhibition of the essential tRNA synthetase enzyme encoded by the introduced cloned gene. In this way, potential inhibitors can be screened for antimicrobial or antibiotic effects, without having to employ slow-growing, pathogenic strains of mycobacteria.

BRIEF DESCRIPTION OF THE DRAWINGS

FIG. 10 is a photograph of clusters of cells on LB plus ampicillin agar or M9 plus ampicillin agar plates that grew when transferred by inoculation from cell suspensions derived from individual colonies. The photograph shows the result of complementation of MI1 *E. coli* cells by various plasmids at three different temperatures. *E. coli* strain MI1 has an isoleucine auxotrophy due to a mutation in ileS causing an elevated $K_m$ of the IleRS enzyme for isoleucine (Iaccarino, M. and Berg, P., *J. Bacteriol.* 105:527–537, 1971; Treiber, G. and Iaccarino, M., *J. Bacteriol.* 107:828–832, 1971). In column A, the plasmid is pKS21; in column B, the plasmid is pGX-56; in column C, the plasmid is pKS-56; in column D, the plasmid is pGEX-4T-2; and in column E, the plasmid is pBSKS(+). (See Example 6.)

DETAILED DESCRIPTION OF THE INVENTION

Figure 1:
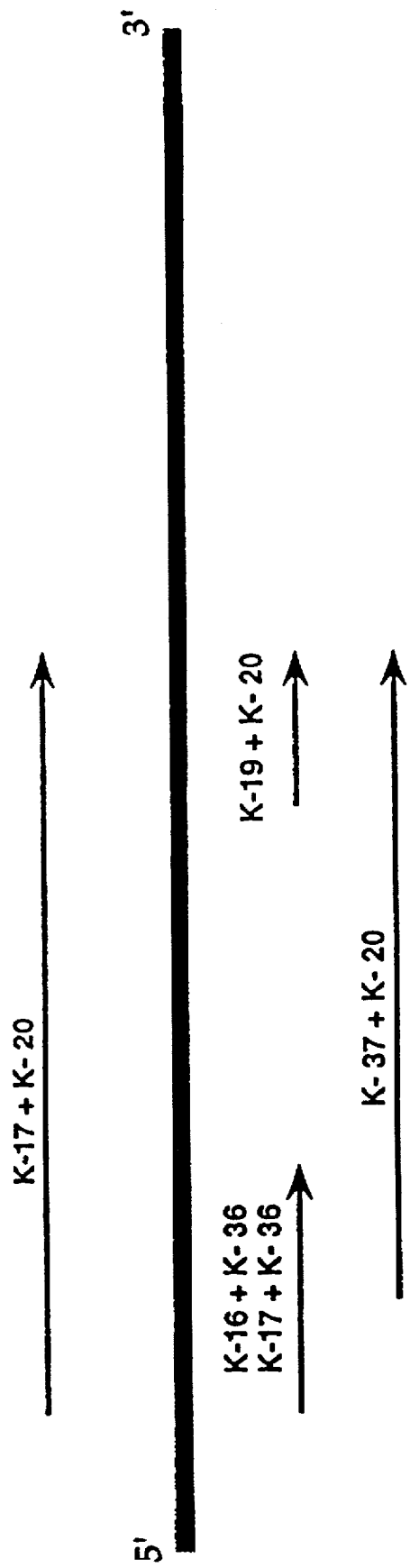
FIG. 1 is a diagram of DNA fragments resulting from PCR (polymerase chain reaction) amplification of *M. kansasii* template DNA using primers whose sequences were based on similarities among previously sequenced IleRS genes from other species (Table 1). The black line represents the coding sequence of the full-length gene.

The aminoacyl-tRNA synthetases are enzymes with the common general function of catalyzing the following reaction:

(aaRS=aminoacyl-tRNA synthetase; aa=amino acid; ATP=adenosine 5'-triphosphate; AMP=adenosine 5'-monophosphate; PP$_i$=inorganic pyrophosphate) The second (aminoacylation) step is often referred to as "charging" the tRNA.

Generally, in each bacterial organism, there are 20 different aaRSs, one specific for each amino acid. For each amino acid, eucaryotic organisms also have 20 different cytoplasmic aaRSs, and generally also encode a separate set of mitochondrial aaRSs. Each aminoacyl-tRNA synthetase enzyme recognizes and reacts with a specific amino acid and one or more tRNAs that recognize the codons specific for that amino acid (cognate tRNAs). The specificity of the aaRS for the amino acid is determined by protein-amino acid interactions, and the specificity of the aaRS for the tRNA is determined by protein-RNA interactions, using different sites on the aaRS.

Although the isolation of a complete aminoacyl-tRNA synthetase gene from an organism of the genus Mycobacterium has not been reported previously, tRNA synthetases of *E. coli* have been studied. Based on conserved sequences and structural motifs, the 20 tRNA synthetases are divided into two classes of 10 enzymes each (see e.g., Burbaum, J. J. and P. Schimmel, *J. Biol. Chem.*, 266(26):16965–16968 (1991)). Class I enzymes, have an N-terminal nucleotide binding fold comprised of alternating β-strands and α-helices and a C-terminal domain that is rich in α-helices and that contains residues needed for interactions with the parts of the tRNA distal to the amino acid attachment site (Shepard, A., et al., *Proc. Natl. Acad. Sci. U.S.A.* 89:9964–9968 (1992); Hou, Y.-M., et al., *Proc. Natl. Acad. Sci. U.S.A.* 88:976–980 (1991)). Five enzymes—cysteinyl-, isoleucyl-, leucyl-, methionyl-, and valyl-tRNA synthetases—are grouped together because they are more closely related in sequence and arrangement of their domains to each other than to the other five members of class I (Hou, Y.-M., et al., *Proc. Natl. Acad. Sci. U.S.A.* 88:976–980 (1991); Eriani, G., et al., *Nucleic Acids Res.* 19:265–269 (1991)). Furthermore, the C-terminal domains of isoleucyl-, leucyl-, methionyl-, cysteinyl- and valyl-tRNA synthetases appear to have a common origin, which is distinct from the C-terminal domain found in other class I enzymes (Shiba, K., et al., *Proc. Natl. Acad. Sci.* USA 89:1880–1884 (1992); Shepard, A., et al., *Proc. Natl. Acad. Sci. U.S.A.* 89:9964–9968 (1992)). In *E. coli*, these five enzymes of class I vary in size from 461 to 951 amino acids and are active as monomers. The size variation is in large part explained by the variability in the lengths of the two insertions designated connective polypeptide 1 (CP1), which is inserted between the second α-helix and third β-strand of the nucleotide binding fold, and CP2, which is placed between the third α-helix and fourth β-strand (Starzyk, R. M., et al., *Science* 237:1614–1618 (1987)). In all of these enzymes, CP1 is the larger of the two insertions and varies in *E. coli* from 61 in cysteinyl-tRNA synthetase to 300 amino acids in isoleucyl-tRNA synthetase (Hou, Y.-M., et al., *Proc. Natl. Acad. Sci. USA* 88:976–980 (1991)). While a portion of CP1 may be deleted from isoleucyl-tRNA synthetase without loss of function (Starzyk, R. M., et al., *Science* 237:1614–1618 (1987)), this insertion is known to facilitate acceptor helix interactions in the related glutaminyl-tRNA synthetase whose three dimensional structure in complex with tRNA$^{Gln}$ has been determined by X-ray crystallography (Rould, M. A., et al., *Science* 246:1135–1142 (1989)). The variable size of the CP1 insertion in class I enzymes possibly reflects the different origins of the motifs recruited into the catalytic domain for acceptor helix interactions (Schimmel, P., et al., *Protein Science* 1:1387–1391 (1992)).

Because the amino acid sequences of the tRNA synthetases have diverged over evolutionary time, significant differences exist between the structures of the enzymes from mammals (e.g., human, bovine) and mammalian pathogens. These differences can be exploited by finding inhibitors of aaRS activity which specifically target a tRNA synthetase of a pathogenic organism, and which may further have specific antimicrobial activity.

Isolation of Isoleucyl-tRNA Synthetase Gene from *Mycobacterium tuberculosis*

Programs designed by the Genetics Computer Group (Madison, Wis.) were used to compare the available DNA sequences of isoleucyl-tRNA synthetase genes and their deduced amino acid sequences to aid in designing the sequences of oligonucleotides to use as primers for PCR synthesis of fragments of the *Mycobacterium kansasii* IleRS gene (Table 1 and SEQ ID NOS:4–10). Multiple sequence alignments were performed using the PILEUP program which aligns multiple sequences based on the method of Needleman and Wunsch (*J. Mol. Biol.* 48:443–453, 1970). From the aligned sequences, the "distances" between any two selected sequences, the evolutionarily conserved residues, and the average similarity among all members at each position were calculated using the DISTANCE, the PRETTY and the PLOTSIMILARITY programs, respectively. These programs use the modified Dayhoff comparison table (Gribskov and Burgess, *Nucleic Acids Res.* 14:6745–6763 (1986)) for calculation.

Two eubacterial (*Escherichia coli*, Webster, T. A., et al., *Science* 226:1315–1317 (1984); *Staphylococcus aureus*, one archaebacterial (*Methanobacterium thermoautotrophicum*, Jenal, U., et al., *J. Biol. Chem.* 266:10570–10577 (1991)), two lower eucaryotic (*S. cerevisiae*, Englisch, U., et al., *Biol. Chem. Hoppe-Seyler* 368:971–979 (1987); Martindale, D. W., et al., *Curr. Genet.* 15:99–106 (1989) and *Tetrahymena thermophila*, Csank, C. and Martindale, D. W., *J. Biol. Chem.* 267:4592–4599 (1992)), and one higher eucaryotic (*Homo sapiens*, Shiba, K. et al., *Proc. Natl. Acad. Sci. USA*, 91:7435–7439 (1994)) isoleucyl-tRNA synthetase sequences have been reported. Multiple sequence alignment of five IleRS sequences revealed several conserved regions (see Table 1). For designing PCR primers, four regions were chosen (Table 1). These regions are well conserved only in IleRS (except region 3, which is also conserved in LeuRS and ValRS). Seven different degenerate primers were synthesized for these regions as shown in Table 1. In regions 1 and 3, the sequences were divided into two subgroups according to similarity, and primers were designed separately for each subgroup.

*M. kansasii* genomic DNA was used as a source of mycobacterial DNA template for the polymerase chain reaction (PCR) amplification of isoleucyl-tRNA synthetase gene fragments from eight different combinations of primers (see Example 1, and Tables 1–2). Five of the eight combinations yielded amplified PCR products of the expected sizes (Table 2), which were designated Ile-1B, Ile-2B, Ile-4A, Ile-4B and Ile-5 (see also, FIG. 1). The PCR fragments were cloned into pTZ19R (Pharmacia) by blunt end ligation, and the sizes of the inserted fragments were analyzed by PCR screening using vector-specific forward and reverse primers (Example 2).

Colonies containing the correct inserts were then used for DNA isolation and sequencing by an automated DNA sequencer (Applied Biosystems, Foster City, Calif.). All of the sequences exhibited the high G-C content characteristic of mycobacteria.

The sequences obtained were used to search the GeneBank and the Swiss protein Bank using the Genetics Computer Group package of programs. The computer program PILEUP was used to align the amino acid sequences of IleRSs from several different species for comparison with the deduced amino acid sequences of the *M. kansasii* PCR DNA fragments. The PCR fragments used in this comparison aligned clearly with known isoleucyl-tRNA synthetases.

Figure 2A:
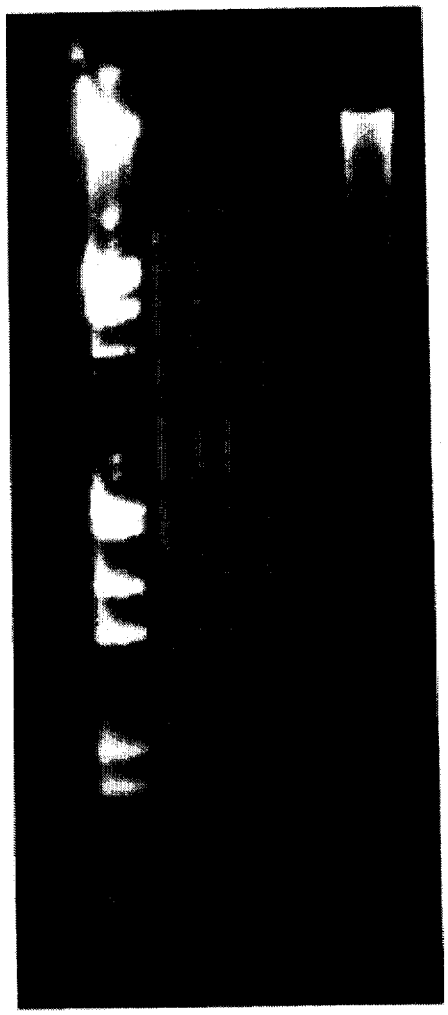
FIG. 2A is a photograph of an ethidium bromide-stained gel showing the separation of DNA fragments from enzymatically digested DNA from virulent *M. tuberculosis* H37Rv (lane 2), avirulent *M. tuberculosis* H37Ra (lane 3), *M. bovis* BCG (bacillus Calmette-Guérin) (lane 4), and *E. coli* (lane 5). (The first lane contains size markers.) The DNA on this gel was transferred to a nylon membrane (DuPont) for analysis by Southern hybridization (see FIG. 2B).
Figure 2B:
FIG. 2B is a photograph of an autoradiogram from a Southern hybridization experiment in which PCR fragments from *M. kansasii* (Ile-2B and Ile-4B) were used as radioactive probes.

Two of the five PCR fragments were radiolabeled and used to probe filters containing SmaI-digested H37Ra, H37Rv or BCG (Bacilli Calmette-Guérin) total DNA as well as BamHI-digested *E. coli* total DNA (Example 3). A single band of approximately 3.6 kilobases (kb) appeared in the lanes containing DNA from the mycobacterial species, but was absent from the lane containing *E. coli* DNA (FIGS. 2A–2B). This result provided evidence that these PCR fragments were of mycobacterial origin and could cross-hybridize to an isoleucyl-tRNA synthetase gene from other mycobacterial species. As a result, the PCR fragments obtained from *M. kansasii* could be used as probes to screen a *M. tuberculosis* library and isolate the isoleucyl-tRNA synthetase of *M. tuberculosis*.

The largest PCR fragment (Ile-1B; ~1.5 kb) was entirely sequenced. From that sequence, specific primers were designed and used to generate two PCR fragments from *M. kansasii* genomic DNA corresponding to the 5' and 3' ends of the ~1.5 kb fragment (Example 4). These PCR fragments were used as probes to screen a λgt11 genomic DNA library of *M. tuberculosis* (a gift of Richard A. Young; Young, R. A. et al., *Proc. Natl. Acad. Sci. USA*, 82:2583–2587 (1985); Example 4).

The screening of 50,000 plaques yielded eight plaques that showed hybridization with both probes. These plaques were further purified and their DNA was isolated and digested with either EcoRI or BsiWI. Cleavage of one of the λgt11, clones (λ clone MS-3) with EcoRI released a ~5.0 kb fragment, and that fragment was inserted into the EcoRI site of pUC19 to yield pMS3. The insert of a second λgt11 clone, designated λ clone SS-5, which contained the whole gene, could not be released with EcoRI. This clone was digested with BsiWI, releasing two fragments designated SS5A (~2.5 kb) and SS5B (~2.0 kb). Fragment SS5B, which contained the 3' end of the gene as determined by Southern analysis, was inserted into the BsiWI site of pBSi (a vector derived from pUC19 by modification of the polylinker to introduce a BsiWI site (see Example 5)) to yield pSS5B. pMS3 and pSS5B were each transformed into *E. coli* strain DH5α.

Although the resulting plasmids did not contain the full length isoleucyl-tRNA synthetase gene, as determined by Southern analysis, the inserts were found to be overlapping (see FIG. 3). pMS3 (pUC19 containing the ~5.0 kb EcoRI fragment) was found to contain the 5' end of the gene, and subclone pSS5B (pBSi containing a ~2.0 kb BsiWI fragment) was found to contain the 3' end of the gene. The insert in pSS5B also contains a portion of the right arm of λgt11 (from the EcoRI site to the BsiWI site).

Figure 5C:
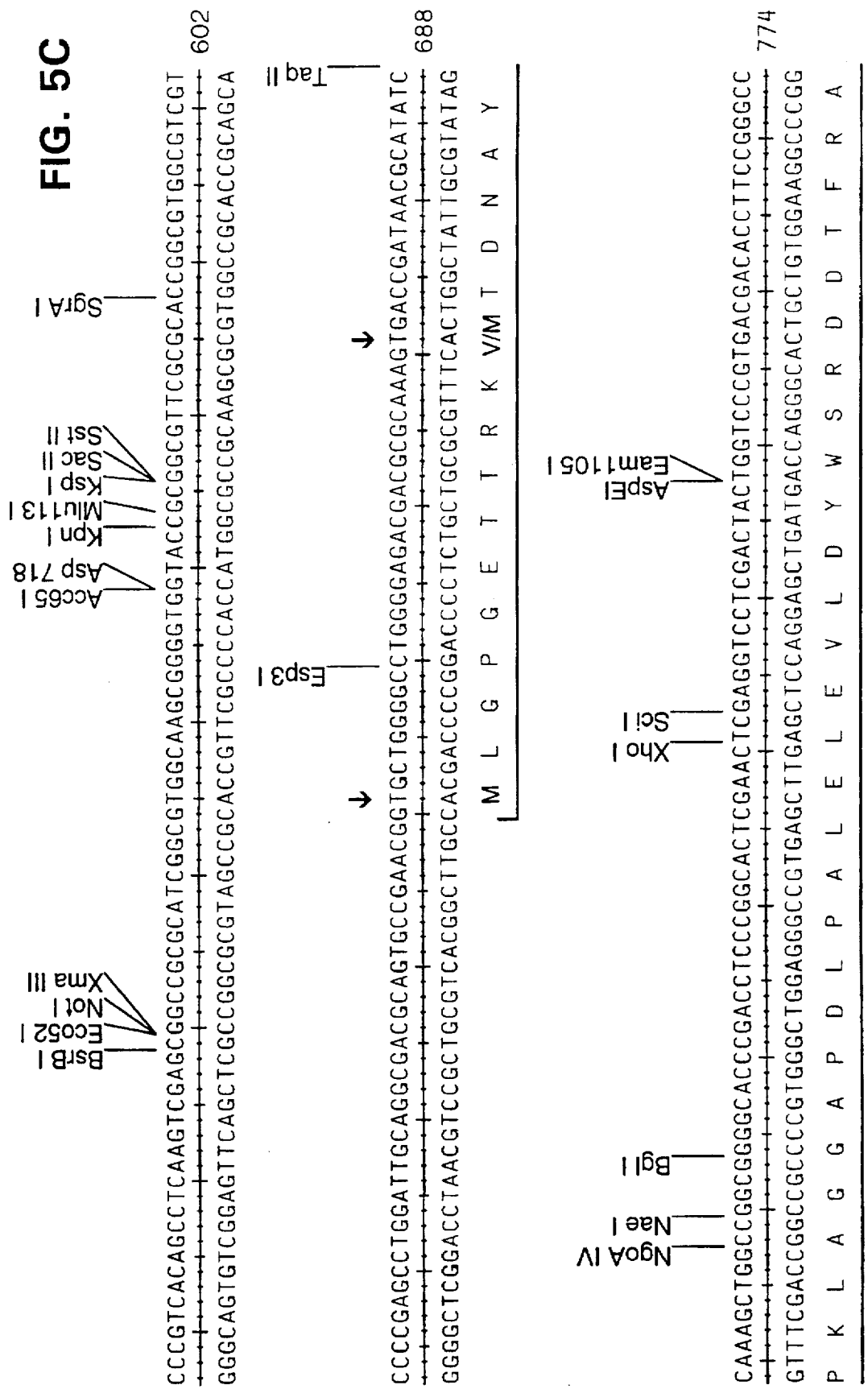
FIGS. 5A–5O is an illustration of the nucleotide sequence (N=G, A, T/U, or C; S=G or C) and predicted amino acid sequence determined for *M. tuberculosis* isoleucyl-tRNA synthetase (see also SEQ ID NO:1), showing an open reading frame with two possible GTG start sites (marked by arrows in FIG. 5C). If the first GTG codon (position 640) is used for initiation of translation, the GTG codon at position 670 would be translated as valine to yield a 1045 amino acid protein (see SEQ ID NO:2); however, if the GTG codon at position 670 is used for initiation, it would be translated as methionine, yielding a protein of 1035 amino acid residues having an N-terminal methionine and residues 12–1045 of SEQ ID NO:2). Either a C or a G residue is present where an S is indicated at positions 3147 and 3148 in FIG. 5M; thus, the amino acid encoded by the codon at 3148–3150 is either Leu (L) or Val (V), and is indicated by Xaa in SEQ ID NO:2.
Figure 5D:
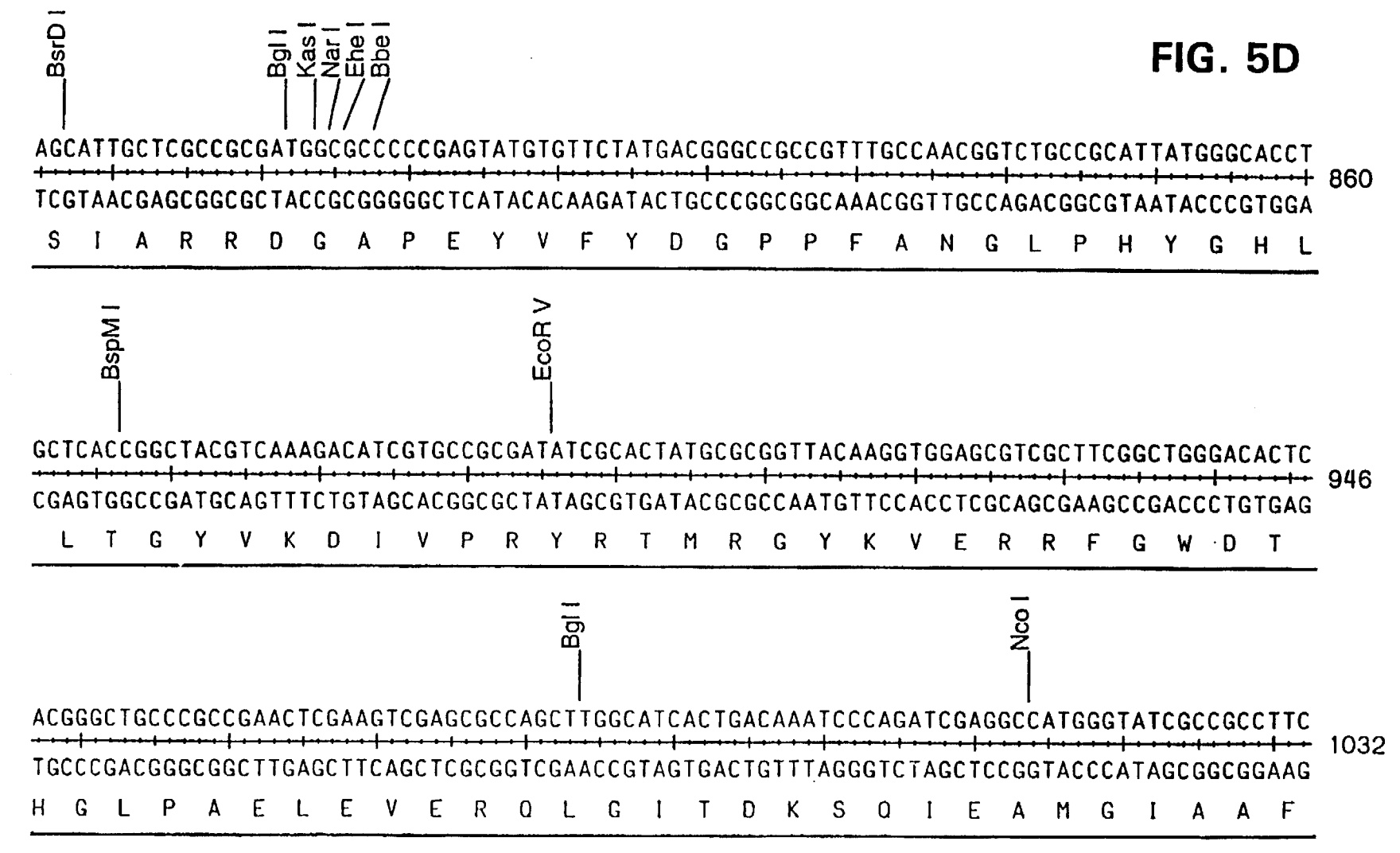
Figure 5M:
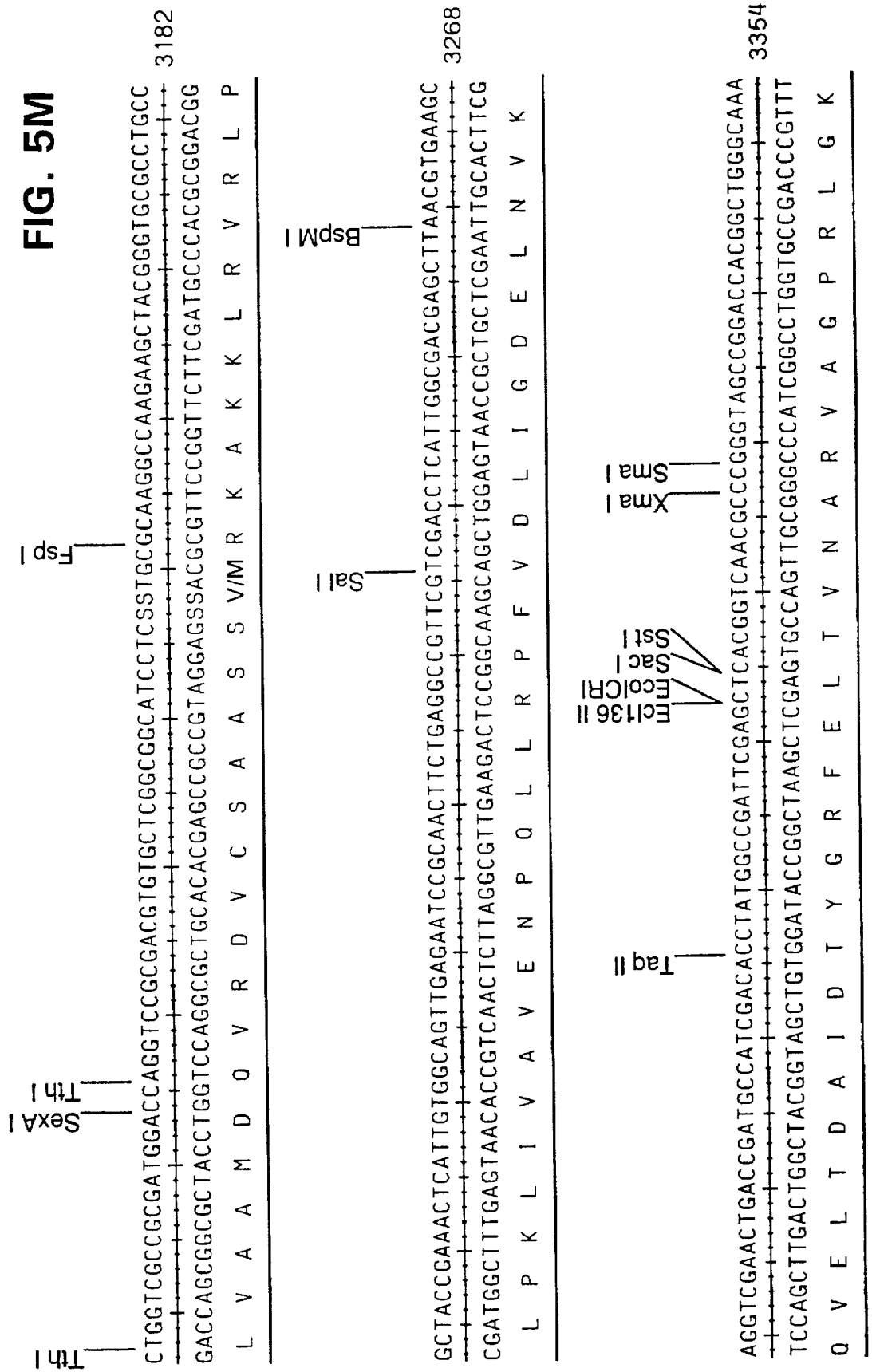
Figure 50:
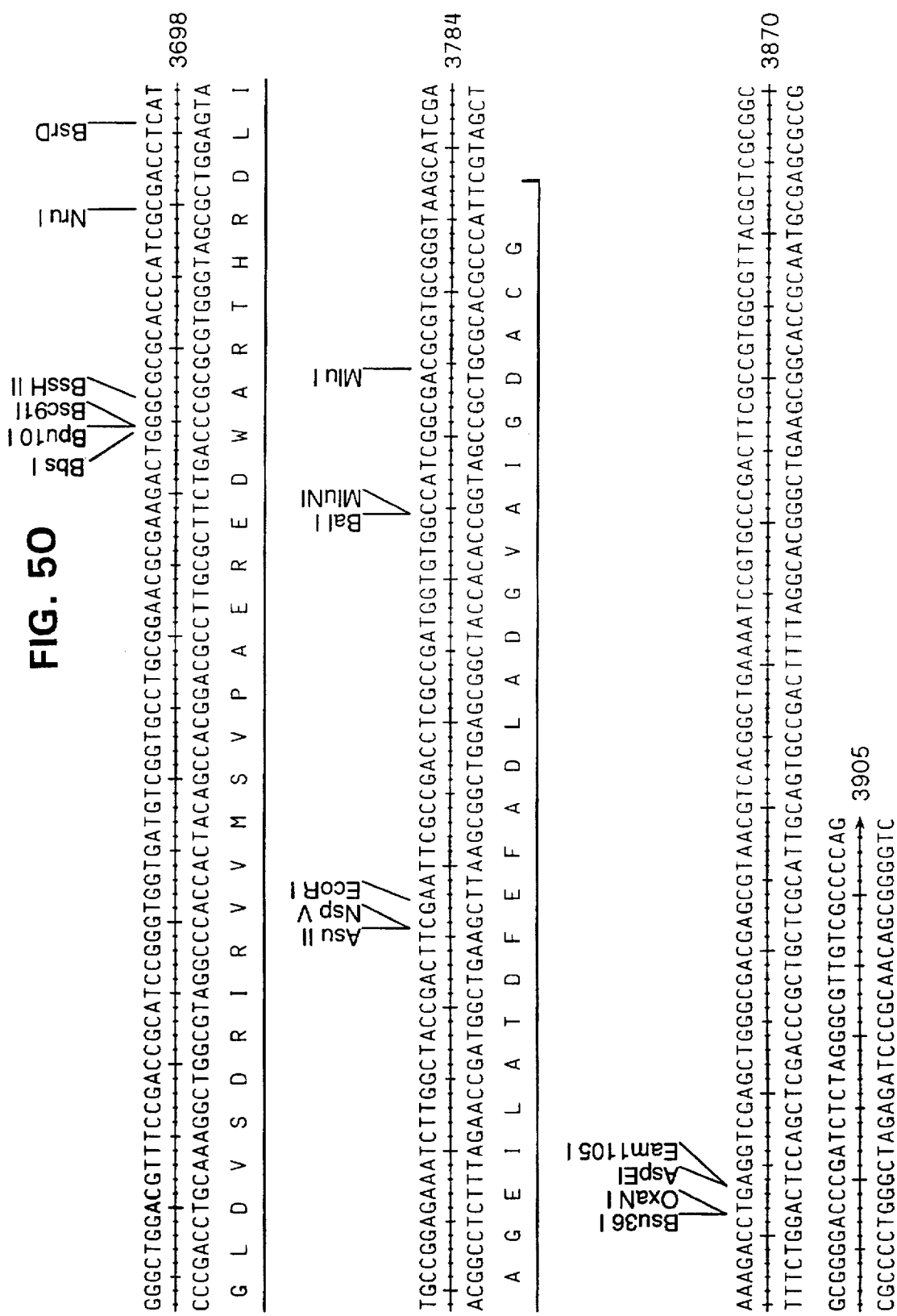

The entire gene and its flanking regions were sequenced (FIGS. 5A–5O; SEQ ID NO:1). An open-reading frame was identified having two possible start sites (FIG. 5C; GTG codons indicated by arrows) based on the distance from the HYGH signature sequence (located at amino acid position 70 relative to the first start site, or position 60 relative to the second start site). GTG (GUG in the mRNA) initiation codons have been observed in mycobacterial genes as well as in the genes of other organisms. However, where a codon other than AUG has been observed, invariably, the amino acid used for initiation has been determined to be methionine (Varshney, U. and U. L. RajBhandary, Proc. Natl. Acad. Sci. USA, 87:1586–1590 (1990)). Accordingly, SEQ ID NO:2 shows an N-terminal methionine for the 1035 amino acid protein illustrated therein.

The amino acid sequence of M. tuberculosis IleRS (translating from the second GTG at position 670 in FIG. 5C (nucleotides 670–672 of SEQ ID NO:1) to give a 1035 amino acid protein) aligned best at its N-terminus with IleRS proteins from other organisms. Consequently, that 1035 amino acid protein was analyzed, using the BLAST program (NCBI; National Center for Biotechnology Information) and the multiple sequence alignment program from the DNAS-TAR package. In particular, the BLAST program was used to identify proteins in the database with amino acid sequence homology to the sequence predicted for the M. tuberculosis IleRS protein. Those sequences identified all corresponded to IleRSs of other organisms. IleRS sequences of other organisms identified by BLAST were then compared to the predicted protein sequence for M. tuberculosis IleRS using the multiple sequence alignment program from the DNAS-TAR package. In particular, percent similarity and percent divergence were determined using the Clustal method with the Structural residue weight table. The predicted amino acid sequence of M. tuberculosis IleRS aligned most closely with the IleRS amino acid sequences of archeabacteria and the cytoplasmic IleRS amino acid sequences of eucaryotes. The percent similarity between the human and M. tuberculosis IleRS amino acid sequences was found to be 38%; the percent similarity between the S. cerevisiae ILS1 product (cytoplasmic enzyme) and M. tuberculosis IleRS amino acid sequences was 43%. For Tetrahymena thermophila, the similarity was 41%; for Methanobacterium thermautotrophicum the similarity was 40%. The percent similarity of M. tuberculosis IleRS to prokaryotic IleRSs was even lower: E. coli (25%); and Staphylococcus aureus (27.5%). Comparison of the 1.5 kb kansasii fragment with the corresponding region of the TB gene showed over 82% identity at the DNA sequence level, suggesting a high level of conservation among IleRSs of mycobacteria, and over 86% identity at the amino acid sequence level, suggesting a high conservation of the IleRS protein sequence in mycobacteria.

Expression of Isoleucyl-tRNA Synthetase Gene of Mycobacterium tuberculosis

Figure 4:
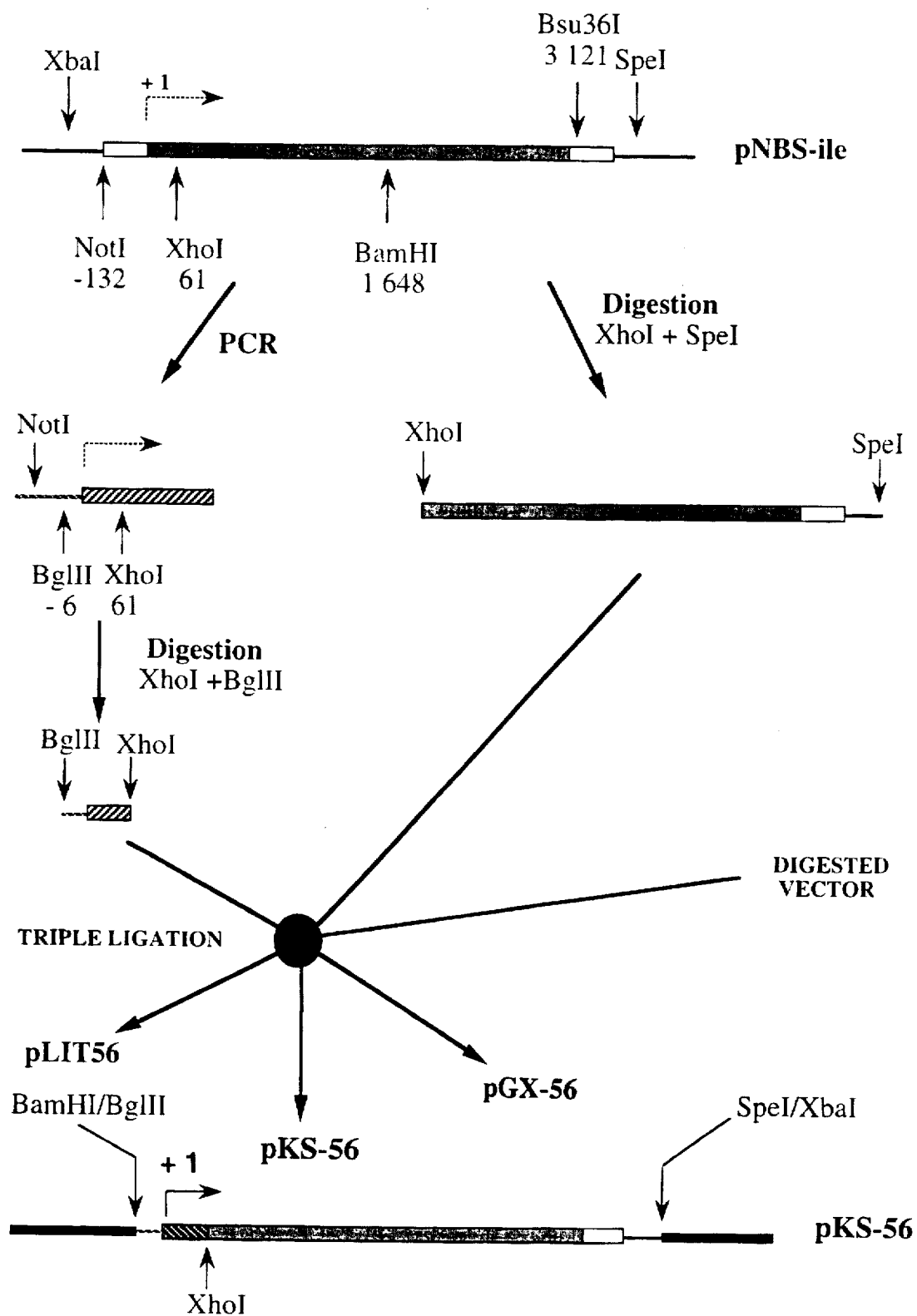
FIG. 4 is a diagram illustrating the construction of expression vectors pKS-56, pGX-56 and pLIT56, containing an *M. tuberculosis* IleRS gene which is modified at its 5' end to facilitate expression of the protein in *E. coli*. The figure is oriented such that the 5' end of the gene is on the left, with numbering as in FIG. 3.

To generate a full-length isoleucyl-tRNA synthetase gene, fragments containing the 5′- and 3′-ends of the gene were ligated together as follows (see FIG. 3). pMS3 was digested with BamHI and NotI, releasing a ~2 kb fragment containing the 5′ end of the gene, which was gel purified. The 3′ end was isolated following digestion of pSS5B with BamHI and BsiWI. The two fragments were then ligated to each other, restoring the BamHI site, and cloned into the NotI and BsiWI digested pNBS vector (a derivative of pUC19 modified by the introduction of NotI, BsiWI and other unique restriction sites (see Example 5)). The resulting plasmid was designated pNBS-ile and was used to transform E. coli strain DH5α. Further modifications made for expression of the M. tuberculosis IleRS gene in E. coli are illustrated in FIG. 4 (see also, Example 5).

pNBS-ile was used to construct several expression plasmids (FIG. 4 and Example 5). The expression vectors were introduced into various E. coli strains to optimize expression or test for genetic complementation. The expression of the TB IleRS was monitored by SDS-PAGE (PAGE is polyacrylamide gel electrophoresis), and the activity of the proteins was tested in vivo by genetic complementation and in vitro by monitoring tRNA aminoacylation (tRNA charging). The activity of the TB IleRS proteins encoded by the various plasmid constructs was confirmed by tRNA charging assay. The M. tuberculosis proteins encoded by pKS-56 and pTR56 and the fusion proteins encoded by pKS-51 and pGX-56 are all active and complement E. coli cells deficient in IleRS activity (see Example 6 and Example 7).

Figure 9A:
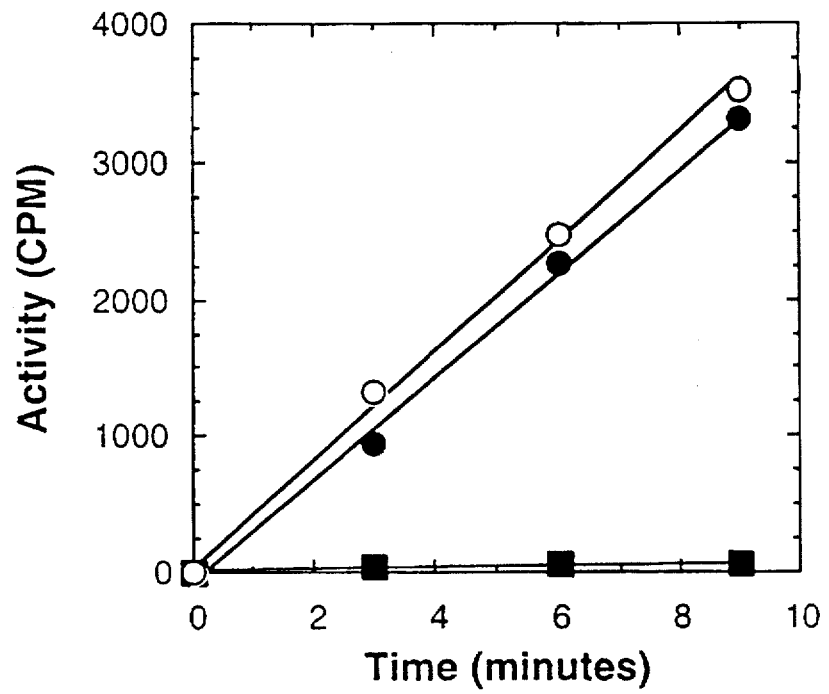
FIG. 9A is a graph showing the aminoacylation activity of the purified GST-fusion protein before (open circles) and after (filled circles) thrombin cleavage. The filled squares show the no tRNA control. The $K_m$ for isoleucine (1.1±0.2 μM) and the rate of tRNA charging activity were similar in the presence or the absence of the GST moiety.
Figure 9B:
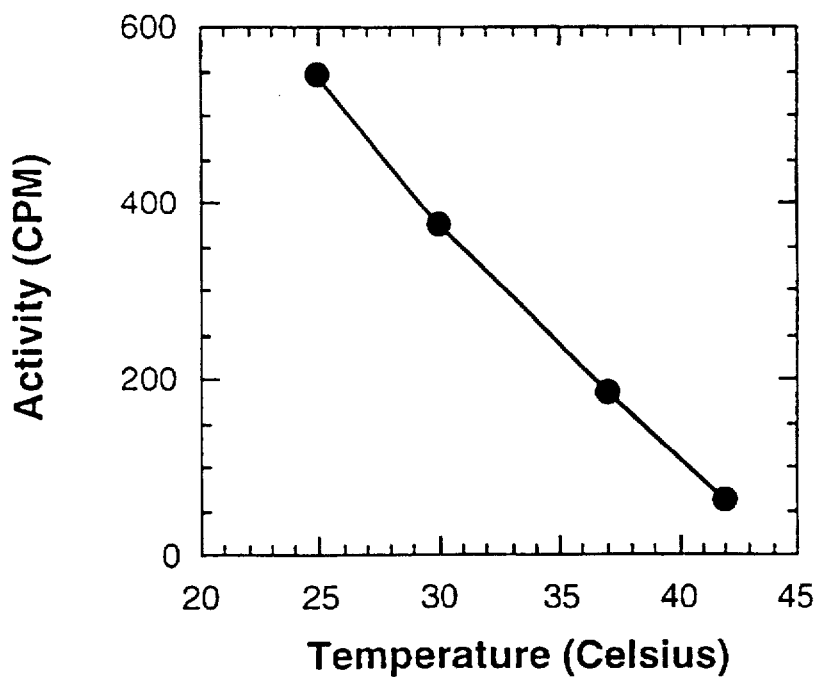
FIG. 9B is a graph which shows the effect of temperature on the in vitro aminoacylation activity of the purified TB GST-IleRS enzyme from JM109 cells carrying plasmid pGX-56.
Figure 11:
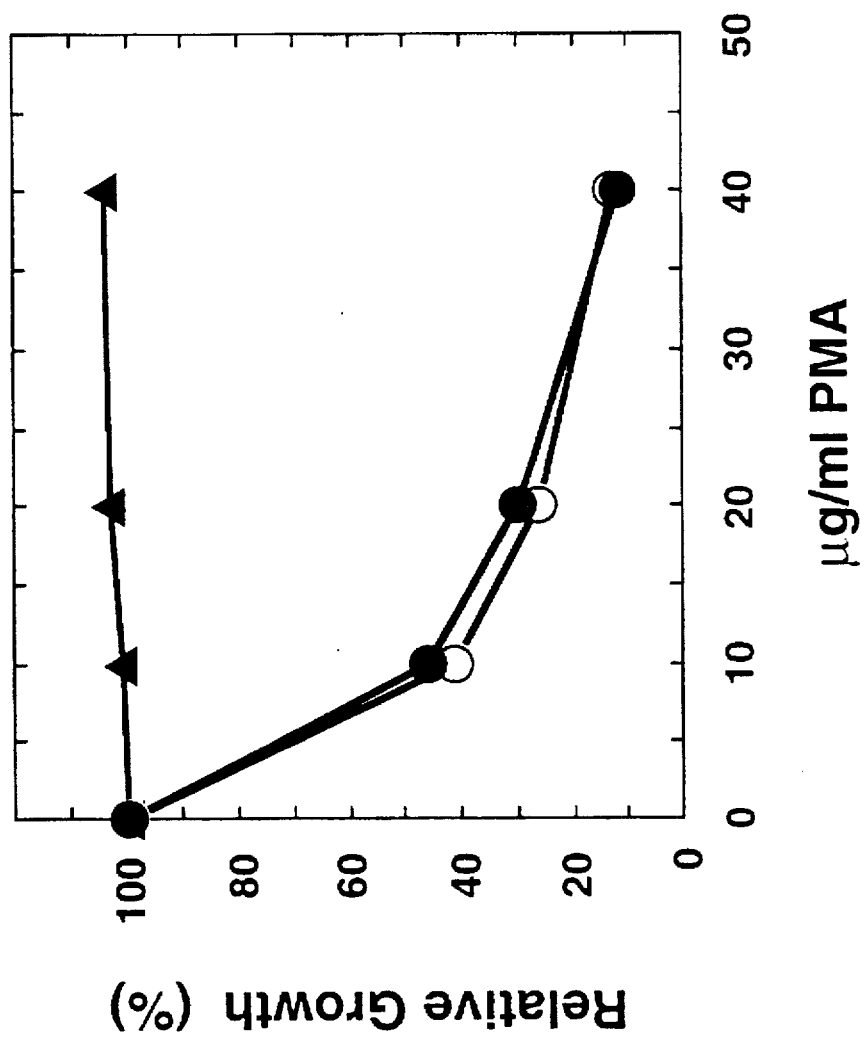
FIG. 11 is a graph illustrating the effect of the administration of various concentrations of pseudomonic acid A (PMA) to liquid cultures of *E. coli* DH5α cells which express the *M. tuberculosis* isoleucyl-tRNA synthetase gene (from pKS-56; ▲) or which express the *E. coli* isoleucyl-tRNA synthetase gene (from pKS21; ○) or the *E. coli* isoleucyl-tRNA synthetase gene from the normal chromosomal location (vector control; ●). (See Example 9.)

Complementation of MI1 E. coli cells (auxotrophic for isoleucine) was most efficient at 30° C. and less efficient at 42° C. (FIG. 10). These observations correlated with the in vitro tRNA charging activity of the purified and unpurified TB IleRS enzyme at different temperatures (FIG. 9B). Activity was optimal at 25° C. (lower temperatures were not tested) and decreased linearly with increasing temperature. All M. tuberculosis IleRS protein constructs behaved similarly in vitro and efficiently aminoacylated tRNAs from both E. coli and yeast (FIGS. 6A and 6B, FIG. 7 and FIG. 9A).

Thrombin cleavage of the GST moiety from the N-terminus of the protein encoded by pGX-56 was very efficient. $K_m$ calculations for isoleucine and kinetic studies showed that the activity of the protein was unchanged upon removal of the GST moiety ($K_m$=1.1±0.2 μM)

The sensitivity of the TB IleRS for the drug pseudomonic acid A (PMA; a specific inhibitor of some prokaryotic IleRS enzymes) was tested. Concentrations of up to 250 μM did not inhibit the charging activity of the enzyme. This result suggests that the TB enzyme is not sensitive to PMA, in contrast to the E. coli IleRS, which is extremely sensitive to PMA (Hughes, J. and Mellows, G., Biochem. J. 176:305–318 (1978)).

In addition, genes encoding proteins with the activity of M. tuberculosis isoleucyl-tRNA synthetase were introduced into E. coli strains having a defect in the endogenous gene for isoleucyl-tRNA synthetase, and complementation of the defect was observed.

Nucleic Acids, Constructs and Vectors

The present invention relates to isolated and/or recombinant (including, e.g., essentially pure) nucleic acids having sequences which encode a mycobacterial isoleucyl-tRNA synthetase, or a portion of a mycobacterial isoleucyl-tRNA synthetase. In one embodiment, the nucleic acid or portion thereof encodes a protein or polypeptide having at least one function characteristic of a mycobacterial isoleucyl-tRNA synthetase, such as a catalytic activity (e.g., catalysis of aminoacyl-adenylate formation, catalysis of aminoacylation of a tRNA with isoleucine), and/or binding function (e.g., tRNA-, amino acid-, or ATP-binding) and/or antigenic function (e.g., binding of antibodies that also bind to a non-recombinant mycobacterial isoleucyl-tRNA synthetase), and/or oligomerization function. Oligomerization activity is the ability of a protein subunit or protein fragment to bind together with one or more other protein subunits or protein fragments, thus altering the quaternary structure of the resulting complex. For example, "adhesive" fragments with oligomerization activity can bind to another fragment with no catalytic activity of its own to restore or partially restore enzymatic activity (Jasin, M., et al., U.S. Pat. No. 4,952, 501). The present invention also relates more specifically to isolated and/or recombinant nucleic acids or a portion thereof having sequences which encode isoleucyl-tRNA synthetase of *M. tuberculosis* or a portion thereof.

The invention further relates to isolated and/or recombinant nucleic acids that are characterized by (1) their ability to hybridize to a nucleic acid having the sequence SEQ ID NO:1 (having an GTG initiator codon as shown or an ATG initiator codon) or its complement, or to a portion thereof comprising nucleotides 640–3777 or its complement, or (2) by their ability to encode a polypeptide of the amino acid sequence SEQ ID NO: 2 or functional equivalents thereof (i.e., a polypeptide which aminoacylates the isoaccepting cognate isoleucine tRNAs of *M. tuberculosis* with isoleucine), or (3) by both characteristics. In one embodiment, the percent amino acid sequence similarity between SEQ ID NO:2 and functional equivalents thereof is at least about 60% ($\geq$60%). In a preferred embodiment, functional equivalents of SEQ ID NO:2 share at least about 70% sequence similarity with SEQ ID NO:2. More preferably, the percent amino acid sequence similarity between SEQ ID NO:2 and functional equivalents thereof is at least about 80%, and still more preferably, at least about 90%. Isolated and/or recombinant nucleic acids meeting these criteria comprise nucleic acids having sequences identical to sequences of naturally occurring mycobacterial IleRS and portions thereof, or variants of the naturally occurring sequences. Such variants include mutants differing by the addition, deletion or substitution of one or more residues, modified nucleic acids in which one or more residues is modified (e.g., DNA or RNA analogs), and mutants comprising one or more modified residues.

Such nucleic acids can be detected and isolated under high stringency conditions or moderate stringency conditions, for example. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M. et al., eds., Vol. 1, Suppl. 26, 1991), the teachings of which are hereby incorporated by reference. Factors such as probe length, base composition, percent mismatch between the hybridizing sequences, temperature and ionic strength influence the stability of nucleic acid hybrids. Thus, high or moderate stringency conditions can be determined empirically, depending in part upon the characteristics of the known DNA to which other unknown nucleic acids are being compared for homology.

Isolated and/or recombinant nucleic acids that are characterized by their ability to hybridize to a nucleic acid having the sequence SEQ ID NO: 1 or its complement (e.g. under high or moderate stringency conditions) may further encode a protein or polypeptide having at least one function characteristic of a mycobacterial isoleucyl-tRNA synthetase, such as a catalytic activity (e.g., aminoacyl-adenylate formation, aminoacylation of a tRNA with isoleucine), binding function (e.g., tRNA-, amino acid-, or ATP-binding), antigenic function (e.g., binding of antibodies that also bind to a non-recombinant mycobacterial isoleucyl-tRNA synthetase), and/or oligomerization function. The catalytic or binding function of a protein or polypeptide encoded by a hybridizing nucleic acid may be detected by standard enzymatic assays for activity or binding (e.g., assays which monitor aminoacyl-adenylate formation, aminoacylation of tRNA). Functions characteristic of isoleucyl-tRNA synthetase may also be assessed by in vivo complementation activity or other suitable methods. Enzymatic assays, complementation tests, or other suitable methods can also be used in procedures for the identification and/or isolation of nucleic acids which encode a polypeptide of the amino acid sequence SEQ ID NO: 2 or functional equivalents thereof. The antigenic properties of proteins or polypeptides encoded by hybridizing nucleic acids can be determined by immunological methods employing antibodies that bind to a mycobacterial isoleucyl-tRNA synthetase, such as immunoblot, immunoprecipitation and radioimmunoassay.

Nucleic acids of the present invention can be used in the production of proteins or polypeptides. For example, DNA containing all or part of the coding sequence for mycobacterial isoleucyl-tRNA synthetase, or DNA which hybridizes to the sequence SEQ ID NO: 1, and having either a GTG or an ATG initiation codon, or its complement, can be incorporated into various constructs and vectors created for further manipulation of sequences or for production of the encoded polypeptide in suitable host cells.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

Portions of the isolated nucleic acids which code for polypeptides having a certain function can be identified and isolated by, for example, the method of Jasin, M., et al., U.S. Pat. No. 4,952,501. The aminoacyl-tRNA synthetases are known to have different quaternary structures, including both monomeric and multimeric structures (e.g., homodimers, tetramers and heteromultimeric $\alpha_2\beta_2$ forms). Thus, as used herein, a nucleic acid which encodes a portion of a mycobacterial isoleucyl- or aminoacyl-tRNA synthetase can also refer to one of two or more distinct subunits of said tRNA synthetase.

A further embodiment of the invention is antisense nucleic acid, which is complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acid can inhibit the expression of the gene encoded by the sense strand. Antisense nucleic acids can be produced by standard techniques.

In one embodiment, the antisense nucleic acid is wholly or partially complementary to and can hybridize with a target nucleic acid, wherein the target nucleic acid can hybridize to a nucleic acid having the sequence of the complement of SEQ ID NO:1. For example, antisense nucleic acid can be complementary to a target nucleic acid having the sequence of SEQ ID NO: 1 or a portion thereof sufficient to allow hybridization. In another embodiment, the antisense nucleic acid is wholly or partially complementary to and can hybridize with a target nucleic acid which encodes a mycobacterial isoleucyl-tRNA synthetase (e.g., *Mycobacterium tuberculosis* IleRS).

*M. tuberculosis* is the major causative agent of infectious tuberculosis in humans. Because advances in the understanding and treatment of this disease would be of tremendous benefit, it was the mycobacterial species selected for most of the experimental work described herein. However, the approaches described to isolate and manipulate the IleRS gene of *M. tuberculosis*, to construct vectors and host strains, and to produce and use the IleRS enzyme, can be applied to other members of the genus of Mycobacteria, including, but not limited to, pathogenic strains such as *M. leprae, M. kansasii, M. avium, M. intracellulare, M. bovis,* and *M. paratuberculosis,* or fast-growing, non-pathogenic strains, such as *M. smegmatis.* The entire *M. tuberculosis* isoleucyl-tRNA synthetase gene described here, or sufficient portions thereof, whether isolated and/or recombinant or synthetic, including fragments produced by PCR, or the *M. kansasii* PCR fragment described herein, can be used as probes or primers to detect and/or recover homologous genes of the other mycobacterial species. This can be achieved using the procedures described herein or other suitable methods (e.g., by hybridization, PCR or other suitable methods).

Proteins

The invention also relates to proteins or polypeptides encoded by nucleic acids of the present invention. The proteins and polypeptides of the present invention can be isolated and/or recombinant. Proteins or polypeptides referred to herein as "isolated" are proteins or polypeptides purified to a state beyond that in which they exist in mycobacterial cells. "Isolated" proteins or polypeptides include proteins or polypeptides obtained by methods described herein, similar methods or other suitable methods, including essentially pure proteins or polypeptides, proteins or polypeptides produced by chemical synthesis, or by combinations of biological and chemical methods, and recombinant proteins or polypeptides which are isolated. Proteins or polypeptides referred to herein as "recombinant" are proteins or polypeptides produced by the expression of recombinant nucleic acids.

In a preferred embodiment, the protein has at least one function characteristic of a mycobacterial isoleucyl-tRNA synthetase, such as a catalytic activity (e.g., catalysis of aminoacyl-adenylate formation, catalysis of aminoacylation of a tRNA with isoleucine), binding function (e.g., tRNA-, amino acid-, or ATP-binding), antigenic function (e.g., binding of antibodies that also bind to a non-recombinant mycobacterial isoleucyl-tRNA synthetase), and/or oligomerization activity. As such, these proteins are referred to as isoleucyl-tRNA synthetases of mycobacterial origin or mycobacterial isoleucyl-tRNA synthetases, and include, for example, naturally occurring mycobacterial isoleucyl-tRNA synthetases, variants of those proteins and/or portions thereof. Such variants include mutants differing by the addition, deletion or substitution of one or more amino acid residues, or modified polypeptides in which one or more residues is modified, and mutants comprising one or more modified residues.

In a particularly preferred embodiment, like naturally occurring mycobacterial isoleucyl-tRNA synthetases, the mycobacterial isoleucyl-tRNA synthetases of the present invention aminoacylate the isoaccepting cognate isoleucine tRNAs of the mycobacterium with isoleucine in a two-step reaction. For example, in the case of *M. tuberculosis*, an isolated mycobacterial isoleucyl-tRNA synthetase is able to aminoacylate each of the isoaccepting species of cognate $tRNA^{Ile}$ of *M. tuberculosis* with isoleucine. In the first step, mycobacterial isoleucyl-tRNA synthetase catalyzes the covalent linkage of isoleucine to ATP to form an adenylate complex (isoleucyl-adenylate) with the release of pyrophosphate, and, in a second step, catalyzes the covalent linkage of isoleucine to a specific tRNA recognized by the enzyme, releasing AMP.

The invention further relates to fusion proteins, comprising a mycobacterial isoleucyl-tRNA synthetase (as described above) as a first moiety, linked to second moiety not occurring in the mycobacterial IleRS as found in nature. Thus, the second moiety can be an amino acid or polypeptide. The first moiety can be in an N-terminal location, C-terminal location or internal to the fusion protein. In one embodiment, the fusion protein comprises an *M. tuberculosis* isoleucyl-tRNA synthetase as the first moiety, and a second moiety comprising a linker sequence and affinity ligand.

Fusion proteins can be produced by a variety of methods. For example, some embodiments can be produced by the insertion of an IleRS gene or portion thereof into a suitable expression vector, such as Bluescript SK+/−(Stratagene), pGEX-4T-2 (Pharmacia; glutathione S-transferase (GST) fusions) and pET-15b (Novagen; His tail fusions). The resulting construct is then introduced into a suitable host cell for expression. Upon expression, fusion protein can be purified from a cell lysate by means of a suitable affinity matrix (see e.g., Example 5; *Current Protocols in Molecular Biology* (Ausubel, F. M. et al., eds., Vol. 2, Suppl. 26, pp. 16.4.1–16.7.8 (1991)).

The invention also relates to isolated and/or recombinant portions of a isoleucyl-tRNA synthetase of mycobacterial origin. A portion of a mycobacterial isoleucyl-tRNA synthetase can also refer to one of two or more distinct subunits of said tRNA synthetase. Portions of the enzyme can be made which have full or partial function on their own, or which when mixed together (though fully, partially, or nonfunctional alone), spontaneously assemble with one or more other polypeptides to reconstitute a functional protein having at least one function characteristic of a mycobacterial isoleucyl-tRNA synthetase. (See, e.g., Shiba, K. and Schimmel, P., *J. Biol. Chem.* 267:22703–22706 (1992) for an example of three inactive peptides from *E. coli* IleRS spontaneously assembling in vivo to reconstitute active enzyme; see also, Burbaum, J. and Schimmel, P., *Biochemistry* 30(2): 319–324 (1991), describing non-overlapping segments of *E. coli* MetRS which can fold together to reconstitute an active enzyme capable of recognizing and charging tRNA in vitro and in vivo). Portions of the enzyme having at least one function characteristic of isoleucyl-tRNA synthetase, such as a catalytic and/or binding function, can be made. Extensive studies on the structure and function of the aaRSs provide the basis for being able to divide the mycobacterial IleRS enzymes into functional domains (Schimmel, P., *Current Biology* 1:811–816 (1991)).

The sequences and structures of the catalytic domain of tRNA synthetases already purified and studied are the basis for dividing them into two distinct classes of ten enzymes each, Class I and Class II (Schimmel, P., *Ann. Rev. Biochem.* 56:125–158 (1987); Webster, T. A., et al., *Science* 226:1315–1317 (1984); Eriani, G. et al., *Nature* 347:203–206 (1990) and Cusack, S., et al., *Nature* 347:249–255 (1990)). Class I enzymes have a well-conserved N-terminal nucleotide binding fold responsible for amino acid binding, aminoacyl-adenylate formation, and tRNA acceptor helix docking. Within this domain are CP1 and CP2, segments of nonconserved amino acid sequence of lengths varying with the species of origin. Studies of the function of mutant aaRS gene products and analyses of the aligned amino acid sequences of aaRSs have revealed conserved and nonconserved regions and likely sites for interactions with other molecules (Shepard, A., et al., *Proc. Natl. Acad. Sci. USA* 89:9964–9968 (1992)). Extensive deletions could be made in the CP1-encoding region of the IleRS gene of *E. coli* without destroying activity of the mutant enzyme (Starzyk, R. M., et al., *Science* 237:1614–1618 (1987)), for example.

Joined to the class-defining domain is a second domain, idiosyncratic to the tRNA synthetase, which provides interactions with the parts of the tRNA which are distal to the amino acid attachment site. In some tRNA synthetases, this second domain interacts directly with the anticodon (Rould, M. A. et al., *Science* 246:1135–1142 (1989) and Cavarelli, J., et al., *Nature* 362:181–184 (1993)), while in other enzymes there is no contact made between the second domain and the anticodon (Biou, V., et al., *Science* 263:1404–1410 (1994)). To a first approximation, the two domains in Class I tRNA synthetases interact with the two distinct domains of the L-shaped tRNA structure. Thus, the recognition elements of the tRNA synthetase and of the tRNA which are needed for the operational RNA code are segregated into discrete protein and RNA domains.

Method of Producing Recombinant Mycobacterial IleRSs

Another aspect of the invention relates to a method to produce mycobacterial isoleucyl-tRNA synthetase or a portion thereof and an expression system and host cells containing a vector appropriate for expression of the mycobacterial isoleucyl-tRNA synthetase.

Cells that express a recombinant mycobacterial isoleucyl-tRNA synthetase or a portion thereof can be made and grown in culture to produce the enzyme for isolation and purification. These cells can be procaryotic or eucaryotic. Examples of procaryotic cells that can be used to express mycobacterial isoleucyl-tRNA synthetases include *Escherichia coli*, *Bacillus subtilis* and other bacteria. Examples of eucaryotic cells that can be used to express mycobacterial isoleucyl-tRNA synthetases include yeasts, such as *Saccharomyces cerevisiae*, and other lower eucaryotic cells, and cells of higher eucaryotes such as those from insects and mammals. (See, e.g., Ausubel, F. M. et al., eds. *Current Protocols in Molecular Biology*, Greene Publishing Associates and John Wiley & Sons Inc., (1993)).

To make host cells that produce a recombinant mycobacterial IleRS protein or portion thereof for isolation and purification, as a first step the gene encoding the IleRS can be inserted into a nucleic acid vector, e.g., a DNA vector, such as a plasmid, virus or other suitable replicon, which can be present in a single copy or multiple copies, or the gene can be integrated in a host cell chromosome. Such a suitable replicon contains all or part of the coding sequence for mycobacterial isoleucyl-tRNA synthetase operably linked to one or more expression control sequences whereby the coding sequence is under the control of transcription signals and linked to appropriate translation signals to permit translation of the IleRS, portion thereof, or of a fusion protein comprising IleRS or portion thereof. As a second step, the vector can then be introduced into cells by a method appropriate to the type of host cells (e.g., transformation, electroporation, infection). In a third step, for expression from the isoleucyl-tRNA synthetase gene, the host cells can be maintained under appropriate conditions, e.g., in the presence of inducer, normal growth conditions, etc.).

As a particular example of the above approach to producing active mycobacterial isoleucyl-tRNA synthetase, a gene encoding the mycobacterial IleRS can be integrated into the genome of a virus that enters the host cells. By infection of the host cells, the components of a system which permits the transcription and translation of the mycobacterial aaRS gene are present in the host cells. Alternatively, an RNA polymerase gene, inducer, or other component required to complete such a gene expression system may be introduced into the host cells already containing the mycobacterial IleRS gene, for example, by means of a virus that enters the host cells and contains the required component. The mycobacterial IleRS gene can be under the control of an inducible or constitutive promoter. The promoter can be one that is recognized by the non-mycobacterial host cell RNA polymerase. The promoter can, alternatively, be one that is recognized by a viral RNA polymerase and is transcribed following infection of the host cells with a virus.

Antibodies

The invention further relates to antibodies raised against an isolated and/or recombinant mycobacterial isoleucyl-tRNA synthetase, including portions thereof (e.g., a peptide), which can specifically recognize and bind to the enzyme. These can be used in methods to purify the protein or portions thereof, or to selectively inactivate one of the enzyme's active sites, or to study other aspects of the enzyme's structure, for example.

The antibodies of the present invention can be polyclonal or monoclonal, and the term antibody is intended to encompass both polyclonal and monoclonal antibodies. Antibodies of the present invention can be raised against an appropriate immunogen, including proteins or polypeptides of the present invention, such as an isolated and/or recombinant mycobacterial isoleucyl-tRNA synthetase or portion thereof, or synthetic molecules, such as synthetic peptides. The immunogen, for example, can be a protein having at least one function of a mycobacterial isoleucyl-tRNA synthetase, as described herein.

The term antibody is also intended to encompass single chain antibodies, chimeric, humanized or primatized (CDR-grafted) antibodies, as well as chimeric or CDR-grafted single chain antibodies, comprising portions from more than one species. For example, the chimeric antibodies can comprise portions of proteins derived from two different species, joined together chemically by conventional techniques or prepared as a contiguous protein using genetic engineering techniques (e.g., DNA encoding the protein portions of the chimeric antibody can be expressed to produce a contiguous protein chain). See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., *BioTechnology*, 10: 1455–1460 (1992), regarding primatized antibody, and Ladner et al., U.S. Pat. No. 4,946,778 and Bird, R. E. et al., *Science*, 242: 423–426 (1988)) regarding single chain antibodies.

Whole antibodies and biologically functional fragments thereof are also encompassed by the term antibody. Biologically functional antibody fragments which can be used include those fragments sufficient for binding of the antibody fragment to a mycobacterial IleRS to occur, such as Fv, Fab, Fab' and F(ab')$_2$ fragments. Such fragments can be produced by enzymatic cleavage or by recombinant techniques. For instance, papain or pepsin cleavage can generate Fab or F(ab')$_2$ fragments, respectively. Alternatively, antibodies can be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the CH$_1$ domain and hinge region of the heavy chain.

Preparation of immunizing antigen, and polyclonal and monoclonal antibody production can be performed using any suitable technique. A variety of methods have been described (see e.g., Kohler et al., *Nature*, 256: 495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0) with antibody producing cells. The antibody producing cell, preferably those obtained from the spleen or lymph nodes, are obtained from animals immunized with the antigen of interest. The fused cells (hybridomas) are isolated using selective culture conditions, and cloned by limiting dilution. Cells which produce antibodies with the desired specificity can be selected by a suitable assay (e.g., ELISA).

Assays for Inhibitors and Tester Strains

The enzymatic assays, binding assays, and construction of tester strains described below, which rely upon the nucleic acids and proteins of the present invention, can be used, alone or in combination with each other or other suitable methods, to identify inhibitors of one or more mycobacterial isoleucyl-tRNA synthetases.

Enzyme Assay

Upon the isolation of an IleRS gene from mycobacteria (as described herein), the gene can be incorporated into an expression system for production of the IleRS or a fusion protein, followed by isolation and testing of the enzyme in vitro. The isolated or purified mycobacterial IleRSs can also be used in further structural studies that allow for the design of antibiotics which specifically target one or more aaRSs of mycobacteria, while not affecting or minimally affecting host or mammalian (e.g., human) aaRSs. Because the amino acid sequences of the tRNA synthetases have diverged over evolution, significant differences exist between the structure of the enzymes from mammals (e.g., human, bovine) and mammalian pathogens, and the design or selection of inhibitors can exploit the structural differences between the pathogen aaRS and the host (e.g., a mammalian host, such a human) aaRS to yield specific inhibitors, which may further have antimicrobial activity.

Furthermore, isolated, active mycobacterial IleRSs can be used in an in vitro method of screening for inhibitors of aminoacyl-tRNA synthetase activity in which the inhibitory effect of a compound is assessed by monitoring IleRS activity according to standard techniques. For example, inhibitors of the activity of isolated, recombinant *M. tuberculosis* IleRS can be identified by the method. In one embodiment, the isolated IleRS enzyme is maintained under conditions suitable for isoleucyl-adenylate formation, the enzyme is contacted with a compound to be tested, and formation of the isoleucyl-adenylate is monitored by standard assay. A reduction in the activity measured in the presence of compound, as compared with the activity in the absence of compound, is indicative of inhibition of isoleucyl-tRNA synthetase activity by the compound. For example, the extent of isoleucyl-adenylate formation catalyzed by purified IleRS can be measured using an ATP-pyrophosphate exchange assay in the presence and in the absence of a candidate inhibitor (Calendar, R. and P. Berg, *Biochemistry*, 5:1690–1695 (1966)). In this reaction, the enzymatic synthesis of ATP from AMP and pyrophosphate in the absence of tRNA is monitored. A candidate inhibitor can be added to a suitable reaction mixture (e.g., 100 mM TrisCl, pH 7.5/5 mM MgCl$_2$/10 mM 2-mercaptoethanol/10 mM KF/2 mM ATP/2 mM [$^{32}$P]-pyrophosphate/1 mM isoleucine), and the mixture is incubated at 25° C. IleRS (to a final concentration of ~10 nM) is added to initiate the reaction. Aliquots of the reaction are removed at various times and quenched in 7% (vol/vol) cold perchloric acid, followed by the addition of 3% (wt/vol) charcoal suspended in 0.5% HCl. The ATP adsorbed to charcoal is filtered onto glass fiber pads (Schleicher & Schuell), and formation of [$^{32}$P]-ATP is quantified by liquid scintillation counting in Hydrofluor (National Diagnostics, Manville, N.J.). The enzyme activity measured in the presence of the compound is compared with the activity in the absence of the compound to assess inhibition. Alternatively, a candidate inhibitor can be preincubated with enzyme under suitable conditions. Preincubation in the absence of substrate provides a more sensitive assay for the detection of inhibition (e.g., detects slow binding inhibitors). For example, the compound can be added to a mixture containing ~10 nM isoleucyl-tRNA synthetase in 100 mM TrisCl, pH 7.5/5 mM MgCl$_2$/10 mM 2-mercaptoethanol/10 mM KF, and preincubated at 25° C. for 20 minutes. To initiate the reaction, ATP, [$^{32}$P]-pyrophosphate and isoleucine are added to final concentrations of 2 mM, 2 mM and 1 mM, respectively. The reaction is monitored as described above, and the activity measured in the presence of compound is compared with the activity in the absence of compound to assess inhibition.

In another embodiment, formation of the aminoacylated tRNA is monitored in a standard aminoacylation assay. Inhibitors identified by enzymatic assay can be further assessed for antimicrobial activity using tester strains as described herein, or using other suitable assays. For example, the extent of aminoacylation of tRNA with isoleucine catalyzed by IleRS (e.g., a GST fusion) can be measured by monitoring the incorporation of [$^3$H]-isoleucine into trichloroacetic acid-precipitable [$^3$H]-isoleucyl-tRNA in the presence of a candidate inhibitor, as compared with activity in the absence inhibitor. Appropriately diluted IleRS (~0.4 nM) can be preincubated for 20 minutes at 25° C. in, for example, 50 mM HEPES, pH 7.5/0.1 mg/ml BSA (bovine serum albumin)/10 mM MgCl$_2$/10 mM 2-mercaptoethanol/20 mM KCl/1–20% DMSO (preferably about 1%) in the presence or absence of a compound to be tested. The preincubation mixture can be supplemented with ATP, [$^3$H]-isoleucine and tRNA to final concentrations of, for example, 4 mM ATP/ 20 µM [$^3$H]-isoleucine (0.6 µCi), and 90 µM crude tRNA or 2 µM specific tRNA$^{Ile}$. The reaction can be maintained at 25° C., and aliquots are removed at specific times, and applied to filter paper discs (3 MM, Whatman) that have been presoaked with 5% (wt/vol) trichloroacetic acid. Filters are washed for three 10-minute periods in 5% trichloroacetic acid, rinsed in 95% ethanol and 100% ether, and the incorporation of [$^3$H]-isoleucine into tRNA (formation of [$^3$H]-Ile-tRNA) is measured in Betafluor by liquid scintillation counting. The aminoacylation assay can also be performed without preincubation under suitable conditions (e.g., using ~0.4 nM IleRS in a reaction mixture containing 50 mM HEPES, pH 7.5/0.1 mg/ml BSA (bovine serum albumin)/10 mM MgCl$_2$/10 mM 2-mercaptoethanol/20 mM KCl/1–20% DMSO/4 mM ATP/20 µM [$^3$H]-isoleucine (0.6 µCi), and 90

μM crude tRNA or 2 μM specific tRNA$^{Ile}$) in the presence or absence of test compound. An IC$_{50}$ value (the concentration of inhibitor causing 50% inhibition of enzyme activity) for a known amount of active IleRS can be determined.

Binding Assay

Isolated, recombinant aaRS or a portion thereof, and suitable fusion proteins can be used in a method to select and identify compounds which bind specifically to mycobacterial aaRSs, such as *M. tuberculosis* Ile tRNA synthetase, and which are potential inhibitors of aaRS activity. Compounds selected by the method can be further assessed for their inhibitory effect on aaRS activity and for antimicrobial activity.

In one embodiment, isolated or purified mycobacterial IleRS can be immobilized on a suitable affinity matrix by standard techniques, such as chemical cross-linking, or via an antibody raised against the isolated or purified mycobacterial IleRS and bound to a solid support. The matrix is packed in a column or other suitable container and is contacted with one or more compounds (e.g., a mixture) to be tested under conditions suitable for binding of compound to the IleRS. For example, a solution containing compounds is made to flow through the matrix. The matrix can be washed with a suitable wash buffer to remove unbound compounds and non-specifically bound compounds. Compounds which remain bound can be released by a suitable elution buffer. For example, a change in the ionic strength or pH of the elution buffer can lead to a release of compounds. Alternatively, the elution buffer can comprise a release component or components designed to disrupt binding of compounds (e.g., one or more substrates or substrate analogs which can disrupt binding of compound to the aaRS, such as isoleucine, ATP, tRNA$^{Ile}$ for IleRS, or other suitable molecules which competitively inhibit binding).

Fusion proteins comprising all of, or a portion of, a mycobacterial aaRS linked to a second moiety not occurring in the mycobacterial aaRS as found in nature (see above), can be prepared for use in another embodiment of the method. Suitable fusion proteins for this purpose include those in which the second moiety comprises an affinity ligand (e.g., an enzyme, antigen, epitope). The fusion proteins can be produced by the insertion of a mycobacterial aaRS gene or portion thereof into a suitable expression vector, which encodes an affinity ligand (e.g., pGEX-4T-2 and pET-15b, encoding glutathione S-transferase and His-Tag affinity ligands, respectively). The expression vector is introduced into a suitable host cell for expression. Host cells are lysed and the lysate, containing fusion protein, can be bound to a suitable affinity matrix by contacting the lysate with an affinity matrix under conditions sufficient for binding of the affinity ligand portion of the fusion protein to the affinity matrix.

In one aspect of this embodiment, the fusion protein is immobilized on a suitable affinity matrix under conditions sufficient to bind the affinity ligand portion of the fusion protein to the matrix, and is contacted with one or more compounds (e.g., a mixture) to be tested, under conditions suitable for binding of compound to the aaRS portion of the bound fusion protein. Next, the affinity matrix with bound fusion protein is washed with a suitable wash buffer to remove unbound compounds and non-specifically bound compounds. Compounds which remain bound can be released by contacting the affinity matrix with fusion protein bound thereto with a suitable elution buffer (a compound elution buffer). Wash buffer is formulated to permit binding of the fusion protein to the affinity matrix, without significantly disrupting binding of specifically bound compounds. In this aspect, compound elution buffer is formulated to permit retention of the fusion protein by the affinity matrix, but is formulated to interfere with binding of the compound (s) tested to the aaRS portion of the fusion protein. For example, a change in the ionic strength or pH of the elution buffer can lead to release of compounds, or the elution buffer can comprise a release component or components designed to disrupt binding of compounds to the aaRS portion of the fusion protein (e.g., one or more substrates or substrate analogs which can disrupt binding of compounds to the aaRS portion of the fusion protein, such as isoleucine, ATP, tRNA$^{Ile}$ for IleRS, or other suitable molecules which competitively inhibit binding).

Immobilization can be performed prior to, simultaneous with or after contacting the fusion protein with compound as appropriate. Various permutations of the method are possible, depending upon factors such as the compounds tested, the affinity matrix-ligand pair selected, and elution buffer formulation. For example, after the wash step, fusion protein with compound bound thereto can be eluted from the affinity matrix with a suitable elution buffer (a matrix elution buffer, such as glutathione for a GST fusion). Where the fusion protein comprises a cleavable linker, such as a thrombin cleavage site, cleavage from the affinity ligand can release a portion of the fusion with compound bound thereto. Bound compound can then be released from the fusion protein or its cleavage product by an appropriate method, such as extraction.

To enrich for specific binding to the aaRS portion of the fusion protein, compounds can be pre-treated, for example with affinity matrix alone, with affinity ligand or a portion thereof (e.g., the portion present in the fusion protein), either alone or bound to matrix, under conditions suitable for binding of compound to the aaRS portion of the bound fusion protein.

One or more compounds can be tested simultaneously according to the method. Where a mixture of compounds is tested, the compounds selected by the foregoing processes can be separated (as appropriate) and identified by suitable methods (e.g., PCR, sequencing, chromatography). Large combinatorial libraries of compounds (e.g., organic compounds, peptides, nucleic acids) produced by combinatorial chemical synthesis or other methods can be tested (see e.g., Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; see also Rebek et al., Process for Creating Molecular Diversity, U.S. Ser. No. 08/180,215, filed Jan. 12, 1994, relating to compounds without tags; see also, Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible. Where compounds do not carry tags, chromatographic separation, followed by mass spectrophotometry to ascertain structure, can be used to identify individual compounds selected by the method, for example.

Random sequence RNA and DNA libraries (see Ellington, A. D. et al., *Nature* 346: 818–822 (1990); Bock, L. C. et al., *Nature* 355: 584–566 (1992); and Szostak, J. W., *Trends in Biochem. Sci.* 17:89–93 (March, 1992)) can also be screened according to the present method to select RNA or DNA molecules which bind to an aaRS, such as *M. tuberculosis* IleRS. Such molecules can be further assessed for antimicrobial effect upon introduction into a cell (e.g., by expression in the case of an RNA molecule selected by the method).

Tester Strains

Nucleic acids of the present invention can also be used in constructing tester strains for in vivo assays of the effect on the activity of the mycobacterial enzyme of a substance which is added to tester strain cells. A tester strain comprises a host cell having a defect in a gene encoding a mycobacterial aaRS, and a heterologous mycobacterial aaRS gene which complements the defect in the host cell gene. Thus, complementation of a particular defective host cell aaRS gene by a heterologous mycobacterial aaRS gene is a threshold requirement for a tester strain. Because the aaRS genes are essential, the heterologous gene can be introduced into the host cell simultaneously with inactivation of the host cell gene to preserve viability. Alternatively, the heterologous gene can be introduced into the host cell before inactivation or loss of the host cell gene. In this case, to test for complementation, the host cell is then subjected to some change in conditions (e.g., a change in temperature, growth medium, selection conditions) which causes inactivation or loss of either the host aaRS gene or gene product, or both.

For example, temperature-sensitive alleles of the genes encoding cytoplasmic IleRS and MetRS have been described in *S. cerevisiae* (Hartwell, L. H., and McLaughlin, C. S., *J. Bacteriol.* 96:1664–1671 (1968)), and are available from the Yeast Genetic Stock Center (University of California-Berkeley; catalog nos. 341 and 19:3:4, respectively). Temperature-sensitive serS strains of *E. coli* have also been described (Low, B., et al., *J. Bacteriol.* 108:742–750 (1971); Clarke, S. J. et al., *J. Bacteriol.* 113:1096–1103 (1973)).

If the heterologous gene complements the inactivated host cell gene, such a cell can be used in a test of whether a substance that enters the cells specifically interacts with the mycobacterial tRNA synthetase (or a component in the pathway of tRNA synthetase gene expression) introduced for testing, to cause loss of function of the tested mycobacterial tRNA synthetase in those host cells. Thus, such cells are "tester strains." Successful cross-species complementation has been described already, for example, for yeast seryl-tRNA synthetase and for yeast isoleucyl-tRNA synthetase in *E. coli* (Weygand-Durasevic, I., et al., *Eur. J. Biochem* 214:869–877 (1993); Racher, K. I., et al., *J. Biol. Chem.* 266:17158–17164 (1991)). Cross-species complementation within the genus Mycobacterium can also serve as the basis for testing, for example, the aaRS enzymes of *M. tuberculosis* in *M. smegmatis*.

In tester cells to be used in an assay for chemical substances that can inhibit the function of a specific mycobacterial aaRS, the gene for the mycobacterial tRNA synthetase can, for example, physically replace the host aaRS gene or can be present in addition to a host aaRS gene that does not produce a functional product, and the mycobacterial gene whose gene product is to be tested complements the host gene. A substance to be tested is administered to the tester cells, and the viability or growth of such cells can be compared with that of cells of a suitable control.

Suitable host cells can be mycobacterial or non-mycobacterial host cells. As a tester strain comprises a host cell comprising a heterologous mycobacterial aaRS gene (i.e., one from a heterologous species), a suitable mycobacterial host cell is heterologous with respect to the species from which the mycobacterial gene to be tested is isolated. One feature of using a heterologous mycobacterial species as a host cell in a tester strain is that mycobacterial species are likely to be more similar to each other than to non-mycobacterial species with respect to their enzymatic and structural composition. *M. smegmatis* or other fast growing, non-pathogenic species of mycobacteria, are preferred mycobacterial species to use as hosts for the construction of tester strains such as those comprising a *M. tuberculosis* SerRS gene.

Preferred non-mycobacterial species to use as hosts for the construction of tester strains are *E. coli*, *S. cerevisiae*, and *B. subtilis*. These species are especially amenable to genetic manipulation because of their history of extensive study.

Suitable host cells having a genotype useful for the construction of a tester strain can be constructed or selected using known methods. For example, both in *E. coli* and in *S. cerevisiae*, a first plasmid which contains a functional copy of a host chromosomal aaRS gene which is to be inactivated later, along with some selectable marker gene, can be constructed and introduced into cells. Then, an inactivating mutation can be caused in the chromosomal copy of the aaRS gene. One way to do this is by causing or selecting for a double crossover event which creates a deletion and insertion. This can be done by introducing into the cells double-stranded DNA having regions of homology to the DNA flanking the target aaRS gene, and having between these regions a gene encoding a selectable marker, either on a suitable vector or as a DNA fragment, as appropriate (Jasin et al., U.S. Pat. No. 4,713,337; Schimmel, P., U.S. Pat. No. 4,963,487; Toth, M. J. and Schimmel, P., *J. Biol. Chem.* 261(15):6643–6646 (1986); Rothstein, R., Methods in Enzymology 194:281–301 (1991)). Such an approach simultaneously inserts a selectable marker and results in a deletion of the endogenous gene between the flanking sequences provided. Where needed to maintain viability, a compatible maintenance plasmid is provided encoding an endogenous or complementing aaRS. A test plasmid which is compatible with the maintenance plasmid, and which contains a mycobacterial aaRS gene to be tested for complementation, can be introduced into the host cells. If the first plasmid has been constructed to have a mechanism to allow for inhibition of its replication (for example, a temperature sensitive replicon) or to have a mechanism by which cells containing the first plasmid can be selected against (by, for example, the use of 5-fluoroorotic acid to select against *S. cerevisiae* cells which have a first plasmid containing the URA3 gene), cells which survive by virtue of having a complementing mycobacterial aaRS gene on the second plasmid can be selected (Sikorsky, R. S. and Boeke, J. D., Methods in Enzymology 194:302–318 (1991)).

A number of *E. coli* strains already exist in which an aaRS gene has been inactivated by some method, in whole or in part, yielding an observable phenotypic defect which can be complemented. For example, a null strain in which the gene encoding IleRS has been inactivated by deletion and insertion of a selectable marker, and a mutant strain designated MI1 in which the gene encoding IleRS has been conditionally inactivated by a point mutation, have been described (Shiba, K. and P. Schimmel, *Proc. Natl. Acad. Sci. USA*, 89:1880–1884 (1992); Shiba, K. and P. Schimmel, *Proc. Natl. Acad. Sci. USA*, 89:9964–9968 (1992); and Shiba, K. and P. Schimmel, *J. Biol. Chem.*, 267:22703–22706 (1992), each describing ΔileS203::kan *E. coli* strains; see also Iaccarino, M. and Berg, P., *J. Bacteriol.* 105:527–537 (1971) and Treiber, G. and Iaccarino, M., *J. Bacteriol.* 107:828–832 (1971), each describing *E. coli* strain MI1 having an isoleucine auxotrophy due to an elevated Km for isoleucine of IleRS encoded by the IleS gene).

Several *S. cerevisiae* strains have been constructed in which a gene encoding a mitochondrial aaRS has been inactivated (see e.g., Edwards et al., *Cell* 51:643–649

(1987)) or a cytoplasmic IleRS has been cloned (see Meinnel, T. et al., 1995, "Aminoacyl-tRNA synthetases: Occurrence, structure and function", In: *tRNA: Structure, Biosynthesis and Function*, Söll, D. and U. RajBhandary, Eds., (American Society for Microbiology: Washington, D.C.), Chapter 14, pp. 251–292, the teachings of which are incorporated herein by reference, and references cited therein).

The pathogenicity and long generation time of *Mycobacterium tuberculosis* (24 h) are major obstacles in the genetic manipulation of this organism. Thus, in another embodiment, a fast growing species of mycobacteria, such as Mycobacterium smegmatis (2–3 h), can be used as a host to construct a tester strain.

For example, an *M. smegmatis* host cell having a defect in the endogenous IleRS gene can be constructed. The isoleucyl-tRNA synthetase gene from *M. smegmatis* can be obtained and analyzed (e.g., by restriction mapping, sequence analysis) in order to identify a suitable site or sites for the insertion of a spectinomycin resistance cassette or other suitable marker gene to disrupt expression of the gene. The cassette can inserted into the *M. smegmatis* IleRS gene to disrupt the gene at a single site (e.g., by ligation into a particular restriction site) or can replace all or part of the gene (e.g., by ligation into two restriction sites, with deletion of intervening *M. smegmatis* IleRS gene sequences). The resulting construct can be introduced into the *M. smegmatis* host by suitable methods, and homologous recombination between flanking sequences in the construct and on the chromosome leads to inactivation of the *M. smegmatis* gene. Introduction of a heterologous mycobacterial aaRS gene which can complement the host cell defect prior to or simultaneous with inactivation can yield a tester strain.

For example, a linear fragment comprising the *M. smegmatis* gene disrupted by the insertion of a spectinomycin resistance cassette can be used to electroporate *M. smegmatis*. Homologous recombination between this construct and the wild type gene on the chromosome can occur (Husson, R. N., et al., *J. Bacteriol.* 172:519–524 (1990)), inactivating the host gene. Simultaneous with the introduction of the linear fragment, *M. smegmatis* can be transformed with a suitable rescue plasmid, such as pAL5000 (Labidi, A., et al., *Curr. Microbiol.* 11:235–240 (1984)) into which a heterologous mycobacterial (e.g., *M. tuberculosis*) isoleucyl-tRNA synthetase gene has been cloned, which replicates in mycobacteria. Selection of transformants can be performed on 7H media (formulated for the growth of *M. smegmatis*; see Husson, R. N., et al., *J. Bacteriol.* 172:519–524 (1990)) containing spectinomycin.

In another approach, a linear fragment containing the *M. smegmatis* gene disrupted by the insertion of a spectinomycin resistance cassette can be cloned into a pUC vector or other suitable vector which does not replicate in mycobacteria (see, e.g., Yanisch-Perron, C., et al., *Gene* 33:103–119 (1985) regarding pUC vectors). The resulting nonreplicable vector can be used to electroporate *M. smegmatis* simultaneously with a suitable rescue plasmid, such as pAL5000 into which a heterologous mycobacterial (e.g., *M. tuberculosis*) isoleucyl-tRNA synthetase gene has been cloned. The nonreplicable vector will be lost; however, cells in which recombination between the wild type gene on the chromosome and the disrupted gene present on the nonreplicable vector has occurred prior to loss of the construct, leading to inactivation of the host cell IleRS gene, can be selected as indicated above.

Causing or selecting for a double crossover event which creates a deletion and insertion can be used in itself as a one-step method of constructing a tester strain in which a native aaRS gene is replaced by the corresponding mycobacterial gene whose gene product is to be tested. Endogenous recombination mechanisms have been used to advantage previously in *E. coli*, *B. subtilis*, *M. smegmatis*, and *S. cerevisiae*, among other organisms. This method depends on the ability of the mycobacterial gene to be tested to complement the native corresponding aaRS gene. This can be done by introducing into the cells double-stranded DNA having regions of homology to the DNA flanking the target native aaRS gene, and having between these regions a gene encoding a selectable marker as well as the mycobacterial aaRS gene intended to replace the native aaRS gene. The survival of cells expressing the selectable marker is indicative of expression of the introduced mycobacterial aaRS gene and complementation of the defect in the endogenous synthetase.

For example, a tester strain, useful for testing the effect of a compound on the function of IleRS expressed by an inserted *M. tuberculosis* gene, can be constructed in a one-step method. Optional positive and negative controls for this cross-species transformation can be used to show that the resulting strain depends on the IleRS gene from *M. tuberculosis* for growth and that this recombination event is not lethal. For example, *B. subtilis* cells made competent for transformation (Dubnau, D. and Davidoff-Abelson, R., *J. Mol. Biol.* 56:209–221 (1971)) can be transformed with a suitable construct, such as a linearized plasmid containing an insert. Generally, the construct includes a selectable marker gene for antibiotic resistance, or other suitable selectable marker. In one embodiment, a linearized plasmid which contains the *M. tuberculosis* IleRS gene and an antibiotic resistance gene, situated between sequences homologous to the flanking sequences of the endogenous IleRS gene of the host cells, is used to transform the host cell. For a positive control, the linearized plasmid can be constructed in a similar fashion, except that the native *B. subtilis* IleRS gene replaces the *M. tuberculosis* gene, such that a normal *B. subtilis* IleRS gene is located adjacent to the antibiotic resistance marker in the insert. As a negative control, the insert can be designed to contain only the flanking sequences and the antibiotic resistance marker, for example. Antibiotic resistant transformants are not expected upon transformation with the negative control construct, as homologous recombination with the construct results in deletion of the endogenous IleRS gene. Successful construction of a tester strain can also be confirmed by Southern analysis.

The yeast *S. cerevisiae* offers additional possibilities for genetic manipulations to create tester strains, relative to bacteria. Yeast integrating plasmids, which lack a yeast origin of replication, can be used for making alterations in the host chromosome (Sikorski, R. S. and Heiter, P., *Genetics*, 122:19–27 (1989); Gietz, R. D. and Sugino, A., *Gene*, 74:527–534 (1988)). In another embodiment, one-step gene disruptions can be performed in diploid cells using a DNA fragment comprising a copy of an aaRS gene optionally containing a deletion of the aaRS gene and having an insertion of a selectable marker in the gene. For example, ILS1, the gene encoding cytoplasmic isoleucyl-tRNA synthetase from *S. cerevisiae*, has been cloned and sequenced (Englisch, U. et al., *Biol. Chem. Hoppe-Seyler* 368:971–979 (1987)). A suitable fragment can be introduced into a diploid cell to disrupt one chromosomal copy of the yeast gene. Successful integration of the disrupted aaRS gene can be confirmed by Southern blotting and by tetrad analysis of the sporulated diploid cells. The diploid cells heterozygous for the disrupted aaRS gene provide a diploid host strain which can be transformed with a plasmid containing the mycobacterial aaRS gene. These cells can be sporulated and the haploid spores analyzed for rescue of the defective chromosomal aaRS by the mycobacterial aaRS gene.

Alternatively, those diploid cells that are found to contain one copy of the disrupted chromosomal aaRS gene, as well as one functional copy, can be transformed with a maintenance plasmid which contains a gene which complements the disruption, such as the corresponding wild type yeast aaRS gene, and which provides for a mechanism to select against survival of the cells containing this plasmid. These cells can then be made to sporulate to obtain a haploid null strain containing the disrupted chromosomal aaRS gene and the wild type gene on the maintenance plasmid. This haploid tester strain can then be transformed with a test plasmid which expresses a mycobacterial aaRS gene, and the maintenance plasmid can be selected against by growing this strain under appropriate conditions.

In S. cerevisiae, to construct a maintenance plasmid or a test plasmid carrying a heterologous gene, a suitable vector, such as a yeast centromere plasmid (CEN; single-copy) or 2μ vector (high copy) can be used. A heterologous gene to be tested can also be incorporated into the chromosome, using an integrating plasmid, for example. Examples of convenient yeast vectors for cloning include vectors such as those in the pRS series (integrating, CEN, or 2μ plasmids differing in the selectable marker (HIS3, TRP1, LEU2, URA3); see Christianson, T. W., et al., Gene, 110:119–122 (1992) regarding 2μ vectors; see Sikorski, R. S. and Hieter, P. Genetics, 122:19–27 (1989) regarding integrating and CEN plasmids which are available from Stratagene, La Jolla)) and shuttle vectors (integrating, CEN or 2μ vectors) which contain the multiple cloning site of pUC19 (Gietz, R. D. and Sugino, A., Gene, 74:527–534 (1988)). Examples of expression vectors include pEG (Mitchell, D. A. et al., Yeast, 9:715–723 (1993)) and pDAD1 and pDAD2, which contain a GALL promoter (Davis, L. I. and Fink, G. R., Cell 61:965–978 (1990)).

A variety of promoters are suitable for expression. Available yeast vectors offer a choice of promoters. In one embodiment, the inducible GAL1 promoter is used. In another embodiment, the constitutive ADH1 promoter (alcohol dehyrogenase; Bennetzen, J. L. and Hall, B. D., J. Biol. Chem., 257:3026–3031 (1982)) can be used to express an inserted gene on glucose-containing media.

In another embodiment, a eucaryotic host cell is used to construct a mitochondrial tester strain. For example, in yeast, each of the mitochondrial tRNA synthetases is essential for growth on non-fermentable carbon sources (e.g., glycerol). Thus, complementation tests can be conducted in mitochondrial tester strains. As the genes encoding mitochondrial aminoacyl-tRNA synthetases are typically nuclear-encoded, the procedures described above can be modified to construct mitochondrial tester strains, having a defect in a mitochondrial aminoacyl-tRNA synthetase. Modification is necessitated by the fact that yeast strains with a defect in mitochondrial protein synthesis, such as a defective aminoacyl-tRNA synthetase, lose their mitochondrial DNA, rapidly becoming rho$^-$. As a result, these strains are unable to grow on non-fermentable carbon sources even if a complementing gene is introduced into the strain. Therefore, in a haploid strain having a defect in, for example, the yeast mitochondrial isoleucyl-tRNA synthetase gene (e.g., a gene disruption with a cosegregating selectable marker constructed as indicated above), the haploid strain can be crossed with a rho$^+$ strain having a wild-type mitochondrial isoleucyl-tRNA synthetase gene to restore the mitochondrial DNA. The resulting rho$^+$ diploid can then be transformed with a plasmid which encodes the wild-type yeast mitochondrial isoleucyl-tRNA synthetase (i.e., a maintenance plasmid) and a second selectable marker. Following sporulation, progeny spores which carry the defective mitochondrial IleRS, identified by the presence of the cosegregating selectable marker, and the maintenance plasmid, identified by the presence of the second selectable marker, and which are rho$^+$, can be isolated (e.g., by tetrad analysis). Strains constructed in this manner would be suitable for complementation assays using the mycobacterial aminoacyl-tRNA synthetases.

For instance, a plasmid encoding a mycobacterial isoleucyl-tRNA synthetase gene can be introduced into such a strain on a second plasmid having a third selectable marker. As indicated above, the maintenance plasmid can be selected against (e.g., where the selectable marker is URA3, selection on 5-fluoroorotic acid leads to loss of the maintenance plasmid), and complementation by the mycobacterial gene can be monitored on a non-fermentable carbon source.

In another embodiment, a mitochondrial isoleucyl-tRNA synthetase gene disruption with a cosegregating selectable marker can be constructed in diploid rho$^+$ strain (see e.g., Edwards, H. and P. Schimmel, Cell, 51:643–649 (1987)). A plasmid encoding a mycobacterial isoleucyl-tRNA synthetase gene is introduced on a plasmid having a second selectable marker. Sporulation of a resulting diploid will yield two progeny spores carrying the yeast mitochondrial isoleucyl-tRNA synthetase gene disruption, identified by the presence of a cosegregating selectable marker, and two progeny spores carrying the corresponding wild-type gene. The presence of the plasmid can be monitored by the presence of the second selectable marker. Complementation by the mycobacterial gene on the introduced plasmid is indicated by growth on non-fermentable carbon sources of spores carrying the disrupted isoleucyl-tRNA synthetase gene.

In the case of a mitochondrial tester strain, the mycobacterial isoleucyl-tRNA synthetase can be imported into mitochondria to achieve complementation of the mitochondrial defect. When it is necessary to achieve import or desirable to improve the efficiency of import of the mycobacterial isoleucyl-tRNA synthetase in the non-mycobacterial host cell, a gene fusion can be constructed using a sequence encoding a mitochondrial targeting sequence which functions in the host cell. For example, a mitochondrial targeting sequence can be introduced at the amino-terminal end of the mycobacterial isoleucyl-tRNA synthetase. In one embodiment in yeast, the mycobacterial IleRS gene or a sufficient portion thereof is introduced into a vector in which it is placed under the control of the minimal alcohol dehydrogenase promoter and is fused to the yeast cytochrome oxidase IV targeting signal derived from plasmid pMC4 (Bibus et al., J. Biol. Chem., 263: 13097 (1988)). Expression of the construct yields a fusion protein with an N-terminally located cytochrome oxidase IV targeting signal joined to the mycobacterial IleRS protein.

If the construction methods described here are not successful initially, one or more natural or synthetic mycobacterial or other (e.g., procaryotic, such as a bacterial, or eukaryotic, such as a mammalian or fungal) tRNA gene(s) can be introduced into the host cell to provide one or more cognate tRNAs for the mycobacterial aaRS. The tRNA genes of many species have been cloned and sequenced (Steinberg, S., Misch, A. and M. Sprinzl, "Compilation of tRNA sequences and sequences of tRNA genes", Nucleic Acids Res. 21:3011–3015 (1993)). A method for constructing a strain of *Streptomyces lividans* in which an essential tRNA gene has been inactivated in the chromosome, and the gene is instead maintained on a plasmid, has been described (Cohen, S. N., WO 94/08033 (1994)).

Use of Tester Strains

To assess the inhibitory effect of a substance on a tester strain, the cells are maintained under conditions suitable for complementation of the host cell defect, under which complementation of the host cell defect is dependent upon the test gene (i.e., assay conditions). A substance to be tested is administered to the tester cells, and the viability or growth of the tester cells can be compared with that of cells of one or more suitable controls. A variety of control experiments can be designed to assess the inhibitory effect of a substance and/or the specificity of inhibition. The following examples are provided for purposes of illustration.

A preliminary test for inhibitory effect may be conducted where desired. For example, a substance to be tested can be administered to tester cells maintained under assay conditions, and the viability or growth of the tester cells in the presence of the substance can be compared with that of tester cells maintained under the same conditions in the absence of the substance. If it is determined that the substance inhibits growth of the tester cells, a further assessment of the specificity of inhibition by the substance can be conducted as described below.

Alternatively, the inhibitory effect of a substance on tester cell growth and the specificity of inhibition can be determined without conducting the preliminary test for inhibitory activity. The following examples, in which the various cell types are in each case exposed to drug, are provided for purposes of illustration only.

To determine the specificity of inhibition, the viability or growth of the tester cells can be compared with that of cells of one or more suitable control strains maintained under the same conditions. In particular, tester strains and control strains are maintained under assay conditions, and exposed to the substance to be tested.

Strains which are similar to the tester strain, but lack the heterologous mycobacterial aminoacyl-tRNA synthetase gene present in the tester strain (i.e., the "test gene"), can serve as control strains. These control strains comprise a "control gene" which is an aminoacyl-tRNA synthetase gene other than the heterologous mycobacterial aaRS gene present in the tester strain (i.e., an aaRS gene from a different species, such as a heterologous mycobacterial species or non-mycobacterial (procaryotic or eukaryotic) species). The control gene can be a cytoplasmic or mitochondrial aaRS gene, and it encodes an aaRS specific for the same amino acid as the aaRS encoded by the test gene. Viability or growth of the control strain is dependent upon the control gene under the conditions of the assay.

In one embodiment, a cell which is a cell of the same species as the host cell used to construct the tester strain, and which further comprises a control aaRS gene, is selected as a control. For example, the control gene can be a wild-type aaRS gene from the control strain species which encodes an aaRS specific for the same amino acid as the aaRS encoded by the test gene. Such a cell can be used when, for example, the substance or compound to be tested does not significantly affect growth of the control strain under the assay conditions. For example, where an *E. coli* host is used to construct a tester strain having an *M. tuberculosis* aaRS gene, an *E. coli* strain having a wild-type *E. coli* control gene can be used as a control strain. As another example, if a yeast host cell having a defect in a mitochondrial aaRS gene is used to construct the tester strain, a yeast strain comprising the wild type mitochondrial gene can be used as a control strain.

In another embodiment, the control strain can be a strain distinct from the tester strain, which is constructed in a manner which generally parallels that of the tester strain comprising the test gene, such that complementation of the host cell defect, which is also present in the control strain, is dependent upon the control gene under the assay conditions. In this embodiment, the control strain preferably comprises a host cell of the same species as the host cell used to construct the tester strain, and is closely related in genotype to the tester strain. These preferred control strains comprise a "control gene", which, as indicated above, is an aaRS gene other than the test gene (i.e., an aaRS gene from a different species, such as a heterologous mycobacterial species or non-mycobacterial (procaryotic or eucaryotic) species). Furthermore, the control gene, which can be cytoplasmic or mitochondrial, encodes an aaRS specific for the same amino acid as the test gene (e.g., an isoleucyl-tRNA synthetase gene is used as a control for an isoleucyl-tRNA synthetase test gene).

Preferably, the control gene is selected from a species which is a host for the mycobacterial pathogen from which the test gene is derived, permitting the identification of specific inhibitors which selectively inhibit the mycobacterial aaRS (e.g., human control gene for an *M. tuberculosis* test gene; a bovine control gene for an *M. bovis* test gene). Human IleRs genes have been cloned (See e.g., U.S. Ser. No. 08/250,852; Shiba, K. et al., *Proc. Natl. Acad. Sci. USA*, 91:7435–7439 (1994); see also, Accession no. gp|U04953|HSU4953 from the Non-redundant PDB+Swiss Prot+Spupdate+PIR+Gen Pept+GPupdate Database, IleRS of *Homo sapiens*). Alternatively, because the eucaryotic aminoacyl-tRNA synthetases are generally more closely related to each other than to procaryotic aminoacyl-tRNA synthetases, a control gene from another eucaryote (e.g., a different mammalian species) can be used in lieu of one selected from the host species (e.g., a bovine control gene for an *M. tuberculosis* test gene).

For example, a strain isogenic with a tester strain, except for the substitution of a human control gene, can serve as a control strain. Such a control strain can be constructed using the same methods and the same host cell used to construct the tester strain, with the exception that a human control gene is introduced into the host cell in lieu of the heterologous mycobacterial aaRS gene present in the tester.

Under the conditions of this assay, growth or viability of the control strain is dependent upon the control aaRS gene, which complements the host cell aaRS defect in the control strain. Specific inhibition by a substance can be determined by comparing the viability or growth of the tester strain and control strain in the presence of the substance.

In some cases, further controls may be desired to assess specific inhibition. For this purpose, one or more additional "comparison control" strains are used for purposes of comparison. These additional controls can be used to assess the relative effects of a substance upon growth of the tester and control strains in the presence of the substance.

Strains useful for this purpose include, for example, strains of the same species as the host cell used to construct the tester strain, which contain a wild type version of the aaRS gene which is inactivated in the tester strain. In one embodiment, where an *E. coli* host is used to construct a tester strain comprising an *M. tuberculosis* test gene, an *E. coli* strain comprising a wild-type *E. coli* aaRS gene can be used as a comparison control strain. In another embodiment, "parental-type" cells (e.g., parent host cells or a similar strain) are used as comparison controls. For example, the parent host cells of the tester strain can serve as a comparison control strain for the tester strain. Where the tester strain and the control strain have the same parent, a single strain can be used as the comparison control strain for both tester and control strains.

For example, a parent host cell from which the tester and control strains were both constructed (e.g., by inactivation and replacement of the wild type host aaRS gene) can be used as a comparison control strain. This comparison control strain contains a wild type version of the aaRS gene which is inactivated in the tester and control strains, and the viability or growth of this comparison control strain is dependent upon the wild type aaRS under the conditions of the assay. Specific inhibition of the heterologous mycobacterial aaRS encoded by the test gene (or a step in the expression of the mycobacterial gene) is indicated if, after administering the substance to the tester strain, growth of the tester strain is reduced as compared with an appropriate comparison control strain, and growth of the control strain is not reduced, or is relatively less reduced, as compared with its appropriate comparison control strain.

Testing for Antibiotic Resistance to tRNA Synthetase Inhibitors

Mutation of a drug target can reduce the effectiveness of antimicrobial or antibiotic agents, and can confer drug resistance. Thus, mutation of a target mycobacterial aminoacyl-tRNA synthetase, such as a mycobacterial IleRS, could reduce the effectiveness of an inhibitor of aaRS activity. To test for mutations that confer resistance to an inhibitor (e.g., an inhibitor of IleRS activity, including such an inhibitor having antimicrobial activity) a variety of approaches can be used. Mutant mycobacterial aaRS genes can be obtained, for example, by isolation of a mutant gene, or by preparing an individual mutant gene or an expression library of mutant mycobacterial aaRS genes, such as a library of mutants of a mycobacterial IleRS gene. The mutant gene or gene library can be introduced into suitable host cells for screening for resistance to a compound.

An isolated mycobacterial tRNA synthetase gene, such as an *M. tuberculosis* IleRS gene, can be mutagenized by any suitable method including, but not limited to, cassette mutagenesis, PCR mutagenesis (e.g., the fidelity of PCR replication can be reduced to induce mutation by varying $Mg^{2+}$ concentration, increasing the number of amplification cycles, altering temperatures for annealing and elongation, to yield random mutants), or chemical mutagenesis (e.g., nitrosoguanidine, ethylmethane sulfonate (EMS), hydroxylamine) of the entire gene or a portion thereof. The mutagenesis products can be used to construct an expression library of mutant genes (e.g., by inserting the gene into an expression vector, or replacing a portion of an expression vector comprising the wild-type gene with mutant fragments) which is introduced into a host cell.

In one embodiment, if the inhibitor is known to inhibit the host cell (e.g., *E. coli*, yeast, *Bacillus subtilis*, another mycobacterial species) aminoacyl-tRNA synthetase for the same amino acid, the mutant genes can be introduced into the wild-type host and the resulting cells can be exposed to drug to assess resistance.

In another embodiment, the procedures described above relating to tester strains are used in the method to identify mutants resistant to inhibitor. Introduction of the heterologous mycobacterial mutant aaRS gene(s) (i.e., mutant test gene(s)) into a host cell is carried out as described above for the production of tester strains. For example, the library can be introduced into a host cell having a defect in the endogenous gene encoding IleRS. *E. coli* strain IQ843/pRMS711, and its derivative IQ844/pRMS711, are examples of host cells which can be used for the introduction of mutant mycobacterial IleRS gene(s) (Shiba, K. and P. Schimmel, *Proc. Natl. Acad. Sci. USA*, 89:1880–1884 (1992); Shiba, K. and P. Schimmel, *Proc. Natl. Acad. Sci. USA*, 89:9964–9968 (1992); Shiba, K. and P. Schimmel, *J. Biol. Chem.*, 267:22703–22706 (1992)), describing *E. coli* strains having a null allele of the ileS gene (ΔileS203::kan) and a temperature sensitive maintenance plasmid, carrying a wild type ileS allele (encoding *E. coli* IleRS) and having a temperature sensitive replicon which causes loss of the maintenance plasmid at the non-permissive temperature).

Active, drug-resistant mutants are then identified by a selection process in which cells containing mutant genes encoding active aaRS are identified, and the effect of an inhibitor upon aaRS activity is assessed. Cells are maintained under conditions suitable for expression of the mutated gene, and cells containing an active mutant aaRS (e.g., active recombinant *M. tuberculosis* IleRS) are identified by complementation of the host cell defect. Where complementation occurs, each resulting transformant is, in essence, a tester strain comprising a mutant test gene. Cells containing active mutant aaRS as determined by complementation of the host cell defect are then exposed to inhibitor, and the effect of inhibitor on cell growth or viability is assessed to determine whether the active mutant aaRS further confers resistance to inhibitor.

In the case of an ileS null strain, complementation by the mycobacterial gene is indicated by growth at the non-permissive temperature at which the maintenance plasmid is lost. Cells which survive loss of the maintenance plasmid due to the presence of the complementing mutant gene are then challenged with inhibitor to assess resistance.

Resistance can be assessed by comparison to a suitable control by methods analogous to those described above for determining inhibition and/or the specificity of inhibition of a substance in tester cells. For example, the relative effects of an inhibitor upon a tester strain comprising the mutant test gene and upon a tester strain differing only in that it contains the test gene lacking the mutation, can be assessed by comparing the viability or growth of cells which are dependent upon either the test gene or mutant test gene for growth under conditions suitable for complementation of the host cell defect. For instance, the effect of inhibitor on the protein encoded by the test gene lacking the mutation can be determined by comparing the growth of cells containing the test gene in the presence of drug to the growth of such cells in the absence of drug, and the effect of inhibitor on the protein encoded by a mutant test gene can be determined by comparing growth of cells containing the mutant test gene in the presence of drug to the growth of such cells in the absence of drug. A decrease in the inhibitory effect on growth of cells carrying the mutant test gene as compared to the inhibitory effect against cells carrying the test gene lacking the mutation is indicative of resistance.

Cells containing a complementing mutant test gene which further confers resistance to an inhibitor can be used to identify derivatives of the inhibitor with improved antimicrobial effect, which circumvent resistance. Such cells can also be used to identify additional inhibitors having inhibitory activity against the active mutant aaRS encoded by the mutant test gene.

In another embodiment, a naturally occurring mutant mycobacterial aaRS gene, which confers resistance to an inhibitor upon a mycobacterial cell, can be isolated from the mycobacterium using nucleic acids of the present invention as probes. The cloned gene can then be introduced into a host cell as described for the production of tester strains.

Tester cells comprising the mutant test gene which confers resistance, and complements the host defect, can be used as described herein to identify additional inhibitors having reduced susceptibility to the resistance mutation or derivatives of the inhibitor with improved inhibitory activity.

Vectors carrying mutant genes which confer resistance to inhibitor can be recovered and the insert analyzed to locate and identify the mutation by standard techniques, such as DNA sequence analysis, to yield additional information regarding the nature of mutations capable of conferring resistance to selected inhibitors. Mutant proteins can also be expressed and purified for further characterization by in vitro kinetic and binding assays.

Applications in Biochemistry

The mycobacterial isoleucyl-tRNA synthetase or stable subdomains of the protein can be used in a method to separate isoleucine from a mixture of isoleucine and other compounds such as other amino acids, or to specifically isolate L-isoleucine from D-isoleucine. The tRNA synthetase can be chemically attached to a solid support material packed in a column or other suitable container. Alternatively, a fusion protein such as a GST-Ile tRNA synthetase fusion or a His tail-Ile tRNA synthetase fusion permits attachment to a suitable solid support which binds the GST portion or His tail portion of the fusion protein, respectively. The mixture of isoleucine and other compounds can be loaded onto the column under conditions in which isoleucine binds to the tRNA synthetase enzyme, while other compounds present in the mixture flow through the column. In a later step, isoleucine can be released from the enzyme by changing the conditions in the column, such as washing with a solution of high ionic strength to elute L-isoleucine.

In a similar manner, the mycobacterial isoleucyl-tRNA synthetase can be used in a method to isolate tRNA that specifically recognizes the tRNA synthetase.

The mycobacterial isoleucyl-tRNA synthetase can be used in the quantitative determination of isoleucine by its conversion to isoleucyl hydroxamate. An example of an appropriate assay is illustrated by the following series of reactions:

$$\text{isoleucine+ATP} \rightarrow \text{isoleucine} \leftrightarrows \text{AMP+PP}_i$$

(in the presence of excess pyrophosphatase and ATP at pH 7.5, where pyrophosphatase catalyzes the conversion of the product inorganic pyrophosphate ($PP_i$) to inorganic orthophosphate ($P_i$); ATP is adenosine triphosphate; AMP is adenosine monophosphate)

$$\text{isoleucine–AMP+NH}_2\text{OH} \rightarrow \text{isoleucine–NHOH+AMP (at pH 7.5)}$$

$$\text{isoleucine–NHOH+FeCl}_3 \rightarrow \text{colored complex (at acidic pH)}$$

The resulting colored complex can be quantitated by spectrophotometric measurements of absorbance at 540 nm, and compared with a standard curve made using known concentrations of isoleucine. This assay is based on the reactions described by Stulberg and Novelli, *Methods in Enzymology* 5:703–707 (1962).

The mycobacterial isoleucyl-tRNA synthetase can also be used for the quantitative determination of ATP. In the presence of excess isoleucine, and in the presence of pyrophosphatase to convert the product $PP_i$ to $P_i$, the ATP will be quantitatively converted to AMP and inorganic pyrophosphate by the isoleucyl-tRNA synthetase.

$$\text{isoleucine+ATP} \rightarrow \text{isoleucyl–AMP+PP}_i \text{ (in the presence of IleRS)}$$

$$\text{PP}_i\text{+H}_2\text{O} \rightarrow 2\text{P}_i \text{ (in the presence of pyrophosphatase)}$$

$P_i$ can be quantitated by reaction with molybdate, measuring the absorbance at 580 nm and comparing to a standard curve made using known quantities of orthophosphate.

The present invention is more specifically illustrated in the following examples, which are not intended to be limiting in any way.

EXAMPLE 1

PCR Amplification of *M. kansasii* DNA Using Degenerate Primers

Each 50 μl PCR reaction contained 10 ng of DNA template, 100 pmoles of each primer, 1 mM Tris HCl, pH 8.3, 150 μM $MgCl_2$, 5 mM KCl, 10 μg/ml gelatin, 50 μM of each dNTP, and 1.25 units of Taq DNA polymerase (Boehringer Mannheim). The reactions were performed in a Perkin Elmer GeneAmp 9600 thermal cycler for 30 cycles (30" at 94° C., 30" at 55° C., 90" at 72° C.) followed by a 4 minute extension at 72° C. Ten μl of each PCR product were loaded onto a 1.2% or 2% agarose gel in TAE buffer (Sambrook et al., *Molecular Cloning: A Laboratory Manual*, Cold Spring Harbor Press (1989) for separation by electrophoresis, along with DNA size markers in separate lanes. The gels were stained with ethidium bromide and photographed to allow determination of the lengths of the PCR fragments from the distance migrated through the gel.

EXAMPLE 2

PCR Screening of *E. coli* Transformants

The PCR fragments were separated by gel electrophoresis, purified using a GeneClean II kit according to the supplier (Bio 101, LaJolla, Calif.), the ends were filled in with Klenow enzyme, and the fragments were purified again using a Geneclean II kit. The resulting fragments were cloned into a pTZ19R vector (Promega, Madison, Wis.) which had been digested with SmaI and treated with calf intestinal alkaline phosphatase to remove 5' phosphate groups (Boehringer Mannheim, Indianapolis, Ind.). The ligation mixtures were used to transform *E. coli* electrocompetent cells (XL1-Blue; Stratagene) which were then spread on LB agar plates containing 50 μg/ml ampicillin, 50 μg/ml X-Gal (5-bromo-4-chloro-3-indolyl-β-D-galactoside) and 1 mM IPTG (isopropyl-β-D-thiogalactopyranoside).

Colonies containing inserts were identified by their white color and the size of the inserted DNA fragments contained in the plasmids were verified by colony PCR using reverse and forward M13 universal primers. Individual white colonies were picked with a sterile toothpick, streaked on an LB-amp plate and used to inoculate a 50 μl PCR reaction containing 10 pmoles of each M13 universal reverse and forward primers, 1 mM Tris HCl, pH 8.3, 150 μM $MgCl_2$, 5 mM KCl, 10 μg/ml gelatin, 50 μM of each dNTP, and 1.25 units of Taq DNA polymerase (Boehringer Mannheim). The reactions were incubated at 90° C. for 10 minutes to lyse the cells, followed by 30 cycles (94° C. for 90", 57° C. for 90" and 72° C. for 2') and a 4 minute extension at 72° C. Ten μl of each PCR product were separated by electrophoresis on a 1.2% or 2% agarose gel in TAE buffer, followed by staining with ethidium bromide.

EXAMPLE 3

Southern Analysis

Total DNA from Bacille Calmette-Guérin and from *M. tuberculosis* strains H37Ra (avirulent) and H37Rv (virulent;

see Oatway, W. H. et al., *J. Infect Dis.* 59:306–325 (1936)) was digested overnight with SmaI. *E. coli* DNA was digested with BamHI. About 2–3 μg of each DNA sample was loaded onto a 0.8% agarose gel in TBE buffer and the gel was electrophoresed overnight. The gel was then briefly exposed to UV light, treated with HCl and neutralized with NaOH. The DNA was transferred onto a nylon membrane overnight in 20X SSC. The PCR products from Ile-2B and Ile-4B were [$^{32}$P]-labeled using a nick translation kit (Boehringer Mannheim). The unincorporated nucleotides were removed by gel filtration using pre-packed Nap-5 columns (Pharmacia). Prehybridization and hybridization solutions consisted of 5X SSC, 5X Denhardt's, 0.5% SDS, and 5 mM EDTA. Each filter was incubated overnight at 65° C. with 10$^6$ cpm of probe per ml hybridization solution. The filters were washed two times, for at least half and hour each time, in 2X SSC, 0.1% SDS at 65° C., and were placed in cassettes overnight at −70° C. to expose film (Kodak X-OMAT) Similar results were observed if salmon sperm DNA was included at 20 mg/l.

EXAMPLE 4

Screening of *M. tuberculosis* Genomic Library

The largest *M. kansasii* PCR fragment (Ile-1B; ~1.5 kb), which was obtained with the KY-17 (SEQ ID NO:5)+KY-20 (SEQ ID NO:9) primer combination, was fully sequenced. This sequence was used to design four specific nondegenerate synthetic oligonucleotide primers, MS-4 (MS-28-4), MS-6 (MS-22-6), MS-8 (MS-22-8) and MS-10 (MS-26-10), which were used to generate two PCR fragments from *M. kansasii* genomic DNA to be used as radioactive probes for the screening of a λgt11 genomic expression library of *M. tuberculosis* (a gift of Richard A. Young; Young, R. A. et al., *Proc. Natl. Acad. Sci. USA*, 82:2583–2587 (1985)). The primer sequences are shown below.

| Primer Sequence | Orientation |
|---|---|
| MS-4: 5' - TCACCGACAAATCGCAGATCGACGCCAT - 3' | → (SEQ ID NO: 11) |
| MS-6: 5' - GGATCGGCGCAATCGACCCCGT - 3' | ← (SEQ ID NO: 12) |
| MS-8: 5' - AATGCGCCGGCCAGCTCTTCAA - 3' | ← (SEQ ID NO: 13) |
| MS-10: 5' - GGCGTACGGCGAAGACGACATGGCGG - 3' | → (SEQ ID NO: 14) |

The primer combination MS-4+MS-8 yielded a 379 bp fragment, which maps close to the 5' end of the gene. The primer combination MS-10+MS-6 yielded a 714 bp fragment that maps near the middle of the IleRS gene. The relationship between the new PCR fragments and the ~1.5 kb Ile-1B fragment is shown below.

```
        55   MS-4 + MS-8   434      747   MS-10 + MS-6   1461
1                                                              1487
```

The 379 bp and 714 bp PCR fragments were purified using a Geneclean kit (Bio101), radioactively labeled using a nick translation kit (Boehringer-Mannheim Biochemicals, Inc.), and used as probes to screen two sets of duplicate filters (one set from a plate with 5000 plaques and a second set from a plate with 40000 plaques) of the λgt11 expression library.

Following a plaque lift, each filter was denatured, neutralized, air dried, and baked under vacuum at 80° C. for two to three hours. The filters were then prehybridized for several hours at 65° C. in hybridization solution (5X Denhardt's, 5X SSC, 0.5% SDS, 10 mM EDTA and 20 μg/ml salmon sperm DNA) and hybridized overnight with each probe. The filters were then washed three times at 65° C. in 2X SSC, 0.1% SDS and exposed to X-ray film at −80° C. overnight. Eight phage plaques, MS-1, MS-2, MS-3, SS-1, SS-2, SS-3, SS-4 and SS-5, hybridized to both probes and were further characterized. Restriction analysis showed 6 populations of inserts.

EXAMPLE 5

Construction of *E. coli* Vectors
Construction of pBSi and pNBS

In order to introduce a BsiWI site into pUC19, the vector was cleaved with BamHI and EcoRI, and was gel purified. The following primers (top strand is SEQ ID NO:15; bottom strand is SEQ ID NO:16) were synthesized, kinased, and annealed:

```
5'-AATTCGAGCCGTACGCGGG
       GCTCGGCATGCGCCCCTAG-5'
```

The annealed primers were ligated into EcoRI-BamHI cut pUC19 (20:1 primer:vector). The ligation mixture was cleaved with KpnI to destroy vector background, and used to transform *E. coli* DH5α. The resulting construct, pBSi (also referred to as pUC19-BsiWI or pUC19-BsiW), was cleaved with BsiWI to confirm its structure.

In order to introduce additional restriction sites (NotI, BsiWI, and SpeI) into pUC19, the vector was cleaved with BamHI and EcoRI, and was gel purified. The following primers (top strand is SEQ ID NO:17; bottom strand is SEQ ID NO:18) were synthesized, kinased, and annealed:

```
5'-AATTCGAACTAGTTCCCGGGCGTACGGTTTAAACGCGGCCGCGG
       GCTTGATCAAGGGCCCGCATGCCAAATTTGCGCCGGCGCCCTAG-5'
```

The annealed primers were ligated into EcoRI-BamHI cut and gel-purified pUC19. The ligation mixture was used to transform *E. coli* DH5α, and the resulting construct, pNBS, was cleaved with NotI to confirm its structure.

Figure 3:
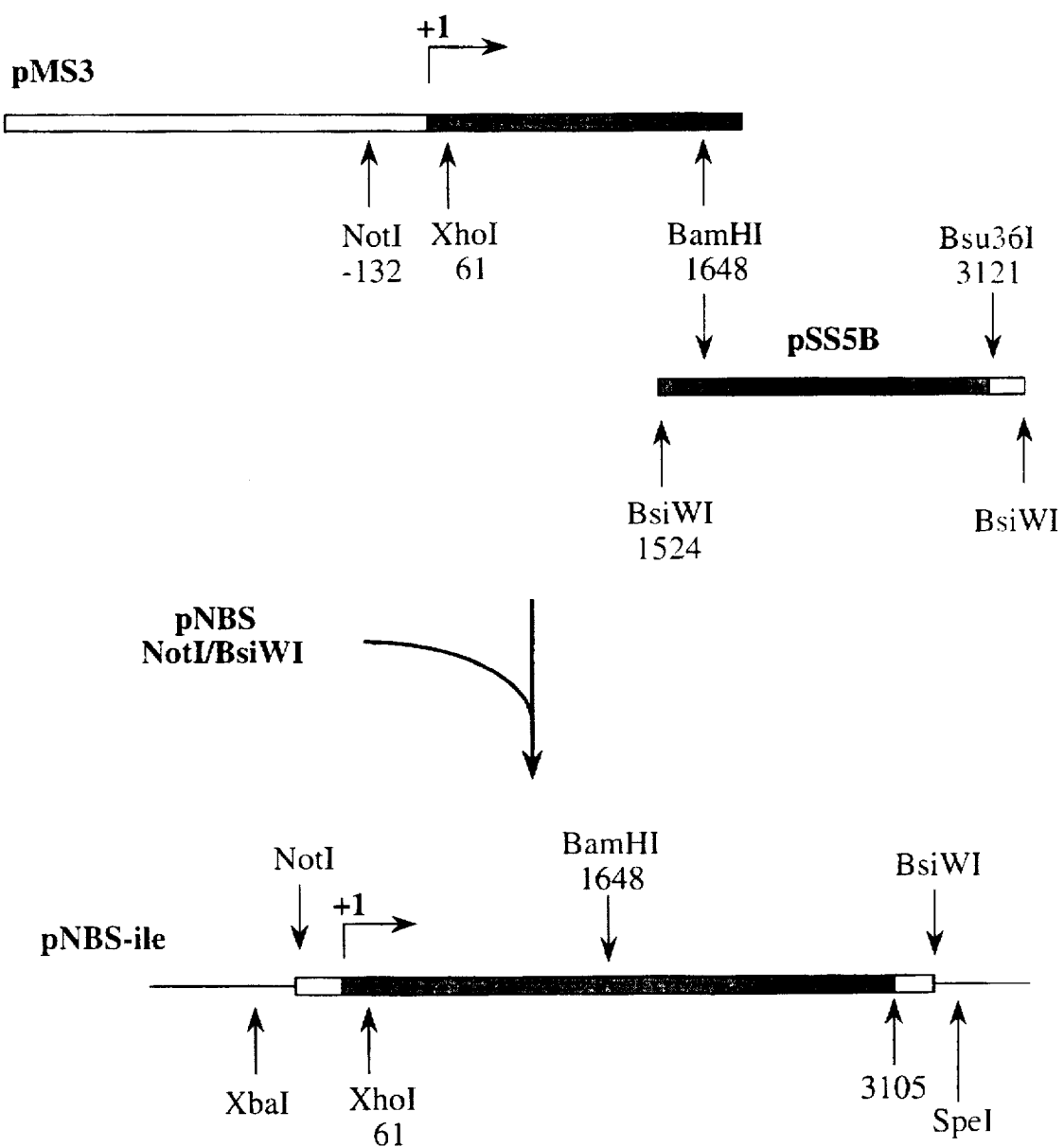
FIG. 3 is a diagram illustrating the construction of pNBS-ile which contains the full-length *M. tuberculosis* isoleucyl-tRNA synthetase gene, by ligation of portions of the *M. tuberculosis* gene present in subclones pMS3 and pSS5B into vector pNBS. The shaded regions indicate the open reading frame. The figure is oriented such that the 5' end of the gene is on the left. Numbering of nucleotides is from left to right, wherein +1 corresponds to the G at position 670 in FIG. 5C. The location of restriction sites is given relative to position +1.

Vectors pUC19 and pBSi were used for cloning fragments isolated from the λgt11 clones to yield pMS3 and pSS5B, respectively. pNBS was used as a vector in the construction of pNBS-ile (also referred to as pNBSTBIle), containing the *M. tuberculosis* IleRS gene (see Detailed Description and FIG. 3).

Construction of pNBS-ile

The full IleRS gene was reconstructed from two overlapping clones: pMS3 (which contains the 5' end of the gene) was digested with NotI and BamHI, and pSS5B (which contains the 3' end of the gene) was digested with BamHI and BsiWI. The two fragments were then purified and ligated into the pNBS vector cut with NotI/BsiWI, restoring the internal BamHI site. The shaded regions on FIG. 3 indicate the open reading frame. Extending from the 3' end of the gene to the BsiWI site is the right arm of λgt11. +1 corresponds to the G at position 670 in FIG. 5C and SEQ ID NO:1. The locations of restriction sites are given relative to position +1.

Plasmid pNBS-ile (in *E. coli* DH5α) was deposited in accordance with the provisions of the Budapest Treaty at the American Type Culture Collection (ATCC), 12301 Parklawn Drive, Rockville, Md. 20852, U.S.A. on Oct. 10, 1996, and assigned Accession Number 98221.

Construction of expression vectors pKS-51, pKS-56, pGX-56 and PTR56

FIG. 4 illustrates the strategy used to construct vectors, specifically pKS-56, for the expression of *M. tuberculosis* isoleucyl-tRNA synthetase. To construct pKS-51, isoleucyl-tRNA synthetase gene sequences from *M. tuberculosis* were cloned into the pBSKS(+) vector (Stratagene, Inc.), such that a fusion protein carrying the first 41 amino acids of the β-galactosidase protein fused in-frame to *M. tuberculosis* isoleucyl-tRNA synthetase can be expressed under the control of the *E. coli* lac promoter. To construct pKS-56, isoleucyl-tRNA synthetase gene sequences from *M. tuberculosis* were cloned into the pBSKS(+) vector such that a protein without the β-galactosidase fusion portion can be expressed. To construct pGX-56, the *M. tuberculosis* isoleucyl-tRNA synthetase gene was cloned into pGEX-4T-2 (Pharmacia) under the control of the tac promoter to produce a fusion protein having the GST protein fused to the N-terminus of the TB IleRS protein. To construct pTR56, the TB IleRS gene was cloned into vector pTrc 99 A (Pharmacia) behind the trc promoter.

In all expression constructs (pKS-51 pGX-56, pTR56 and pKS-56), the $G_{670}$ was modified to an A by PCR mutagenesis to yield an ATG initiation codon (marked *** below) to facilitate expression in *E. coli*. (The fusion genes do not include sequences upstream from position 670 in FIG. 5C and SEQ ID NO:1.) In addition, a BglII site was introduced upstream from the ATG to allow cloning into the compatible BamHI site of the expression vectors. The sequence of the primer (MS-56) used for PCR mutagenesis of the 5' end of the TB IleRS gene in pKS-56, pTR56 and pGX-56 is shown below (SEQ ID NO:27):

resulting PCR fragment was digested with XhoI and BglII, releasing a 67 basepair fragment containing the 5' end of the gene with the GTG to ATG mutation. The 67 basepair fragment was isolated on a 4% Nusiev agarose gel. A ~3.2 kb fragment comprising the 3' end of the *M. tuberculosis* IleRS gene and a portion of the right arm of λgt11 was obtained from pNBS-ile by digestion with XhoI and SpeI, followed by gel purification. The ~3.2 kb fragment contains a portion of the right arm of λgt11.

To construct pKS-51, the 67 bp and 3.2 kb fragments were ligated to BamHI/XbaI digested, gel-purified pBSKS(+) vector (Stratagene). pGX-56 was constructed in two different ways. (1) The 67 bp and 3.2 kb fragments were ligated to BamHI/XbaI digested pGEX-4T-2 (Pharmacia) in a triple ligation reaction. (2) The 67 bp fragment and 3.2 kb fragment were first ligated to BglII-SpeI digested, gel purified pLITMUS 28 vector (New England Biolabs) to generate pLIT56. To construct pGX-56, pLIT56 was digested with SpeI, blunt-ended with Klenow fragment, digested with BglII, gel purified and ligated into BamHI-SmaI digested pGEX-4T-2 (Pharmacia) to yield a fusion construct in which the 5' end of the IleRS gene is fused in frame to the GST gene of *Schistosoma japonicum*. To construct pTR56, pTrc 99 A (Pharmacia) was digested with NcoI, treated with mung bean nuclease, phenol extracted, digested with XbaI and gel purified. pLIT56 was digested with BglII, treated with mung bean nuclease, phenol extracted, digested with SpeI and gel purified. This yielded a ~3.2 kb fragment with one blunt and one SpeI end which contains the entire IleRS gene. The two fragments were ligated, yielding pTR56, which expresses the wild type TB IleRS under the control of the trc promoter.

pKS-56 and pKS-51 constructs are identical to each other, except for the deletion in pKS-56 of a single T residue (indicated in the 5' primer in bold face above) immediately upstream of the ATG codon (marked by ***).

As a result, pKS-51 encodes an in-frame fusion protein containing the first 41 amino acids of β-galactosidase fused to the TB IleRS protein. In contrast, in pKS-56, the absence of the T residue upstream of the ATG codon introduced at position 670 of FIG. 5C and SEQ ID NO:1 apparently prevents the synthesis of a fusion protein. However, in pKS-56, the introduction of the ATG at position 670 provides a new translation initiation site that can be used to produce a non-fusion protein that has activity comparable to that of wild type enzymes (from determinations of $K_m$ in the appropriate range). This protein is thought to be identical to

```
                        ***
5'-ATAAGAATGCGGCCGC AGATCT ATGACCGATAACGCATATCCAA-3'
                     BglII
```

The sequence of the PCR primer (MS-51) used for mutagenesis of the 5' end of the TB IleRS gene in pKS-51 is shown below (SEQ ID NO:19):

that encoded by pTR56. Plasmids pKS-51 and pKS-56 were used to transform *E. coli* strain DH5α.

```
                        ***
5'-ATAAGAATGCGGCCGC AGATCTTATGACCGATAACGCATATCCAA-3'
                     BglII
```

The last 21 nucleotides of the 5' primer correspond to the nucleotide sequence of the *M. tuberculosis* gene from position 671 on (See FIG. 5C and SEQ ID NO:1). The 3' primer was complementary to a downstream sequence within the *M. tuberculosis* isoleucyl-tRNA synthetase open reading frame. Either pMS3 or pNBS-ile was used as template. The A control construct was made in which pKS-51 was digested with Eco72I, which cuts twice within the open-reading frame of the IleRS gene at positions 2012 and 2763 (numbering as in FIGS. 6H–6J and SEQ ID NO:1), releasing a 751 basepair fragment. The digested plasmid was gel-purified and religated to yield pKS-51Δ, in which the IleRS gene has sustained a deletion of 751 bases, including the portion which encodes the essential KMSKS sequence.

EXAMPLE 6

Complementation Assay

Complementation experiments were carried out using different *E. coli* strains having two different types of defects in ileS.

1.) *E. coli* strains IQ843/pRMS711 and its derivative IQ844/pRMS711 (Shiba, K. and P. Schimmel, *Proc. Natl. Acad. Sci. USA*, 89:1880–1884 (1992); Shiba, K. and P. Schimmel, *Proc. Natl. Acad. Sci. USA*, 89:9964–9968 (1992); Shiba, K. and P. Schimmel, *J. Biol. Chem.*, 267:22703–22706 (1992)) contain a chromosomal deletion of the ileS gene, and are propagated by expression of wild type IleRS at 30° C. from a temperature-sensitive maintenance plasmid designated pRMS711, which encodes the wild type ileS gene and a gene which confers chloramphenicol resistance. pRMS711 cannot replicate at 42° C., thus, at the non-permissive temperature, the maintenance plasmid is lost. Following the introduction of a test construct into these strains, the growth of chloramphenicol sensitive colonies at 42° C. is indicative of complementation of the chromosomal ileS deletion by the introduced construct.

In these studies, pKS-51 and pKS-56 (Example 5) were used as test constructs and pKS-51Δ (Example 5) was used as the control construct. Plasmid pAG112, a derivative of pKK223 which expresses the wild-type *E. coli* methionyl-tRNA synthetase from the tac promoter, provided an additional negative control. Plasmid pKS21 (Shiba, K. and P. Schimmel, *Proc. Natl. Acad. Sci. USA*, 89:1880–1884 (1992)), encoding wild type *E. coli* isoleucyl-tRNA synthetase, was used as a positive control.

The test and control constructs were introduced into *E. coli* strains IQ843/pRMS711 and its derivative IQ844/pRMS711 (see above). The resulting transformants were plated on LB plus ampicillin agar (100 μg/ml) in the presence or absence of IPTG (1 mM final concentration), and were incubated at 30° C. or 42° C.

After 24 hours, colonies were readily observed on the plates incubated at 30° C. in the presence of IPTG. However, only pKQ21 transformants showed growth at 42° C. pKS21 transformants grew well in the absence of IPTG, but grew poorly in the presence of the inducer IPTG, indicating toxicity of the *E. coli* wild type IleRS when overexpressed. After 48 hours at 42° C., no visible growth was observed for cells transformed with the test (pKS-51 and pKS-56) or negative control constructs (pKS-51Δ, pAG112).

For each construct, an equivalent number of cells from 4 individual transformants that grew at 30° C. were transferred onto LB plus ampicillin plates with or without IPTG and onto M9 minimal plates containing casamino acids (200 μl of a 20% solution of casamino acids were spread on each M9 plate) with or without IPTG (1 mM final concentration). Plates were incubated at 30° C. or 42° C.

Transformants containing pKS21, encoding wild type *E. coli* isoleucyl-tRNA synthetase, grew well at 30° C. and 42° C. on LB or minimal medium in the absence of IPTG. Transformants containing negative control plasmid pAG112, encoding the wild-type *E. coli* methionyl-tRNA synthetase, did not yield colonies on plates incubated at 42° C. With regard to the test constructs pKS-51 and pKS-56, after 24 hours at 42° C., tiny colonies were observed on the minimal plates with casamino acids and IPTG, but not on the LB plus ampicillin plates. Growth of the IQ843/pRMS711 strains transformed with pKS-51 or with pKS-56 appeared stronger than that of the IQ844/pRMS711 strains transformed with pKS-51 or with pKS-56, possibly because of a lower level of lac repressor in the IQ843/pRMS711 strain. Moreover, in the IQ843/pRMS711 transformants, the difference in growth with IPTG as compared to growth without IPTG was less pronounced.

After 48 hours, transformants of IQ843/pRMS711 growing at 42° C. on M9 minimal medium+casamino acids and IPTG were tested for chloramphenicol sensitivity to verify the loss of the maintenance plasmid, which carries the cat marker. In particular, starting from a patch growing at 42° C. on M9 minimal medium+casamino acids+IPTG, 3 streaks each for test constructs and for control constructs were made on M9 minimal medium+casamino acids+IPTG to obtain single colonies at 42° C. A colony from each streak was tested for chloramphenicol resistance.

For pKS-51, one out of three of these colonies failed to grow. The remaining two colonies were found to be chloramphenicol sensitive, indicating loss of the maintenance plasmid. For pKS-56, one colony was chloramphenicol resistant, and two colonies were chloramphenicol sensitive. The observation of growth at the non-permissive temperature for pKS-51 and pKS-56 transformants contrasts with the lack of growth of transformants carrying the negative controls, plasmids pAG112 and pKS-51Δ.

In a separate experiment, *E. coli* strain IQ843/pRMS711 was transformed with the control construct pKS-51Δ or pKS-51. Three out of three of the pKS-51 transformants tested grew at 42° C. on M9 plates supplemented with casamino acids. In contrast, 0/3 of the pKS-51Δ transformants grew under the same conditions, indicating that complementation of the ileS defect at the non-permissive temperature requires an intact functional TB-IleRS gene.

The ability of these two chloramphenicol sensitive colonies to grow at 42° C. suggests that isoleucyl-tRNA synthetase from *M. tuberculosis*, which is expressed as a fusion protein here, can complement *E. coli* cells deficient in IleRS activity. Although complementation was detectable, it was quite weak as compared to that observed with the wild type *E. coli* gene control as indicated by growth rate.

2.) For complementation of isoleucine auxotrophy in MI1 cells carrying a mutation in *E. coli* ileS, electro-competent MI1 cells were transformed with plasmids pKS21 (*E. coli* wild type ileS), pTR56, pKS-56 or pGX-56, or with control plasmids pBSKS(+) or pGEX-4T-2 (negative constructs). Transformants were selected at 37° C. on LB agar containing 60 μg/ml of ampicillin. Six individual colonies from each transformation were resuspended in 100 μl M9 medium in a well of a 32-well plate, then an equal volume of each cell suspension was transferred with a multi-pronged inoculation manifold to LB plus ampicillin or minimal (M9+50 μM IPTG+thiamine, tryptophan and arginine+60 μg/ml ampicillin) plates that were incubated at 30° C., 37° C. and 42° C. (FIG. 10). All colonies grew on LB plus ampicillin incubated at 37° C. pBSKS(+) and pGEX-4T-2 transformants were not able to grow on minimal plates at any temperature. In contrast, MI1 cells transformed with pGX-56 and pKS-56 grew on minimal plates at 30° C. and 37° C. but very poorly at 42° C. Colonies appeared to grow slower at 37° C. than at 30° C. The effect of temperature on the efficiency of complementation of *E. coli* IleRS mutants by TB-IleRS correlated with the temperature/activity profile of the TB-IleRS enzyme obtained in vitro (FIG. 9B).

EXAMPLE 7

Assay for Aminoacylation Activity by *M. tuberculosis* Isoleucyl-tRNA Synthetase

*E. coli* strain MI1 (Iaccarino, M. and Berg, P., *J. Bacteriol.* 105:527–537 (1971)), which carries a chromosomal point mutation in the ileS gene (conferring a an isoleucine auxotrophy) was transformed with either pKS-51, pKS-56, pKS-51Δ, pBSKS(+) or pKS21, plated on LB plates containing 100 μg/ml ampicillin, and incubated at 37° C. Single colonies were used to inoculate 3 ml of liquid LB containing 100 μg/ml ampicillin, which were grown overnight at 37° C. One ml of each of these cultures was used to inoculate fresh 100 ml cultures (LB containing 100 μg/ml ampicillin) at 37° C. When the cells reached an $OD_{600}$ of 0.5, IPTG was added to a final concentration of 1 mM and the cells were allowed to grow for another three hours. Untransformed MI1 cells were cultured under the same conditions and subjected to IPTG induction. The cells were harvested by centrifugation at 6000 rpm for 10 minutes in a Sorvall SL-250T rotor. The cell paste was kept frozen until lysis.

To make crude extracts, cell pellets were thawed and resuspended in 4 ml of lysis buffer (50 mM potassium phosphate, pH 7.5, 0.1M NaCl, 50 mM β-mercaptoethanol). The cells were lysed by one passage through a French press, and the lysate was clarified by centrifugation at 15,000 rpm for 35 minutes in a Sorvall SL-50T. The clarified supernatant was tested for aminoacylation activity, using a procedure based on Shiba and Schimmel, *J. Biol. Chem.*, 267:22703 (1992).

The conditions of the charging assay were as follows: At time zero, 10 μl of crude extract or purified protein was added to a reaction mixture containing 50 mM HEPES, pH 7.5, 8 mM $MgCl_2$, 20 μM tritiated isoleucine (New England Nuclear) with a specific activity of 2200 cpm/pmol, 10 mM KF, 4 mM ATP, and 0.1 mM total tRNA from either *E. coli* (Sigma) or yeast (*S. cerevisiae*, Boehringer-Mannheim Biochemicals). At various times, 10–20 μl of the reaction were withdrawn, spotted onto Whatman 3 MM cellolose filter diskettes, and the reaction was quenched by placing the filters in 5% ice cold TCA (trichloroacetic acid). Diskettes were washed three times with ice cold 5% TCA, once with 5% ice cold ethanol, once with ether, and air dried. The amount of [$^3$H]-isoleucine incorporated into tRNA bound to the filter was determined by scintillation counting in 5 mls Betafluor (Packard 1600 TR scintillation counter).

Figure 7:
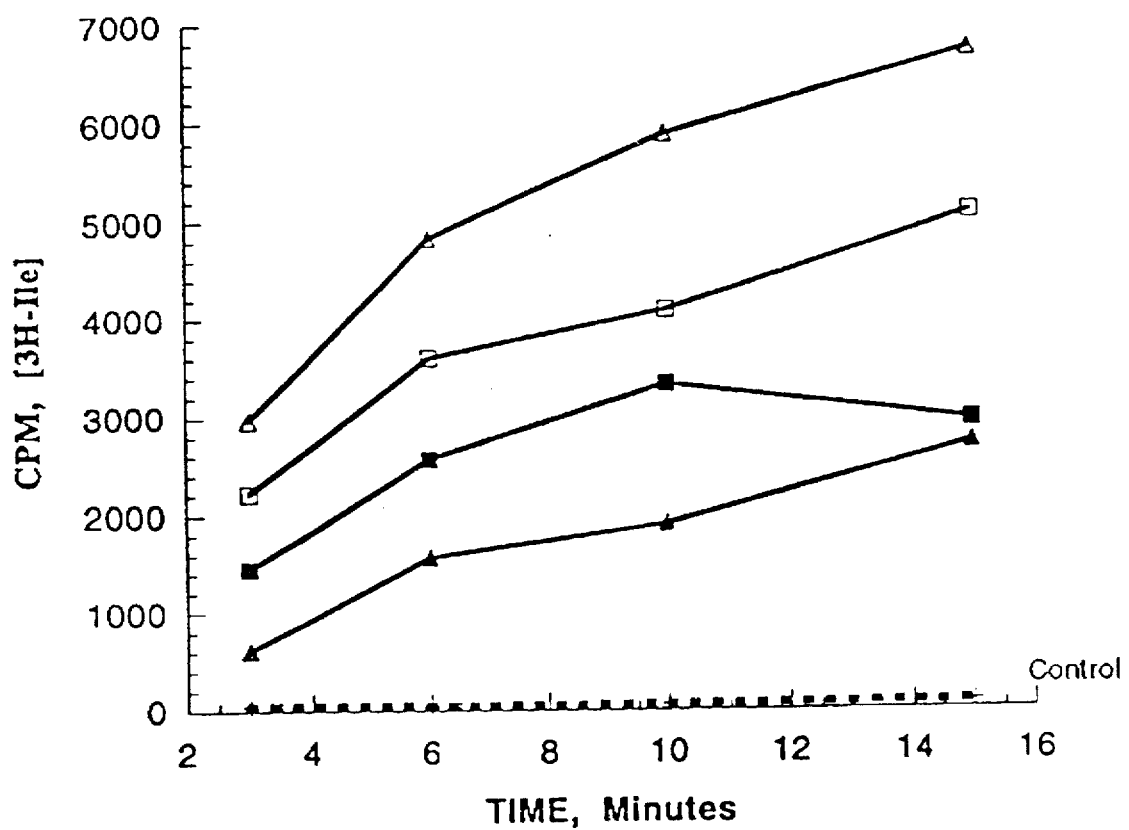
FIG. 7 is a graph illustrating the charging activity (counts per minute of $^3$H-isoleucine incorporated into tRNA) over time of crude extracts from *E. coli* MI1 cells transformed with either pKS-51 or pKS-56, using either total *E. coli* tRNA or yeast tRNA as a substrate (see Example 7). Open squares (□), MI1/pKS-56+*E. coli* tRNA; filled squares (■), MI1/pKS-51+*E. coli* tRNA; open triangles (△), MI1/pKS-56+yeast tRNA; filled triangles (▲), MI1/pKS-51+yeast tRNA; dashed line, no tRNA controls for MI1/pKS-51 and MI1/pKS-56.
Figure 8:
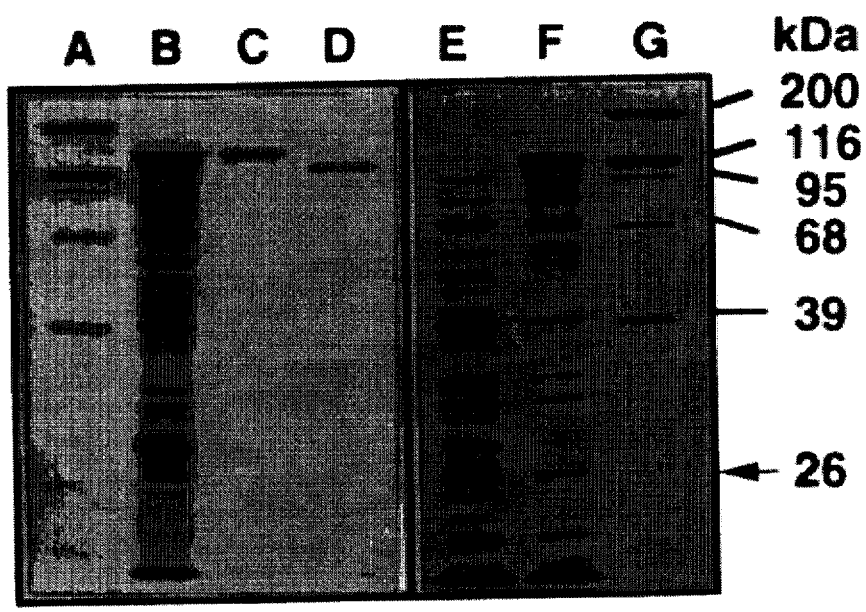
FIG. 8 is a photograph of a 10% SDS (sodium dodecylsulfate) polyacrylamide gel of proteins stained with Coomassie blue. Lanes A and G contain molecular weight markers. Lane B contains total soluble proteins from JM109 cells containing GST-IleRS fusion protein expressed from plasmid pGX-56. Lane C contains purified TB GST-IleRS protein. Lane D contains the products of thrombin cleavage of the purified TB GST-IleRS protein. Lanes E and F contain total soluble protein from JM109 *E. coli* cells containing plasmid pTR56, expressing a TB IleRS protein from the trc promoter before (lane E) and 3 hours after (lane F) induction with IPTG (isopropyl-β-D-thiogalactopyranoside).

In the experiment illustrated in FIG. 7, final reaction volumes were 50 μl, and protein concentrations were 8.75 mg/ml for MI1/pKS-51 extract and 7.0 mg/ml for MI1/pKS-56 extract. No-tRNA controls were included for each type of extract. The data was plotted in FIG. 7 without correction for protein concentration.

Figures 6A, 6B:
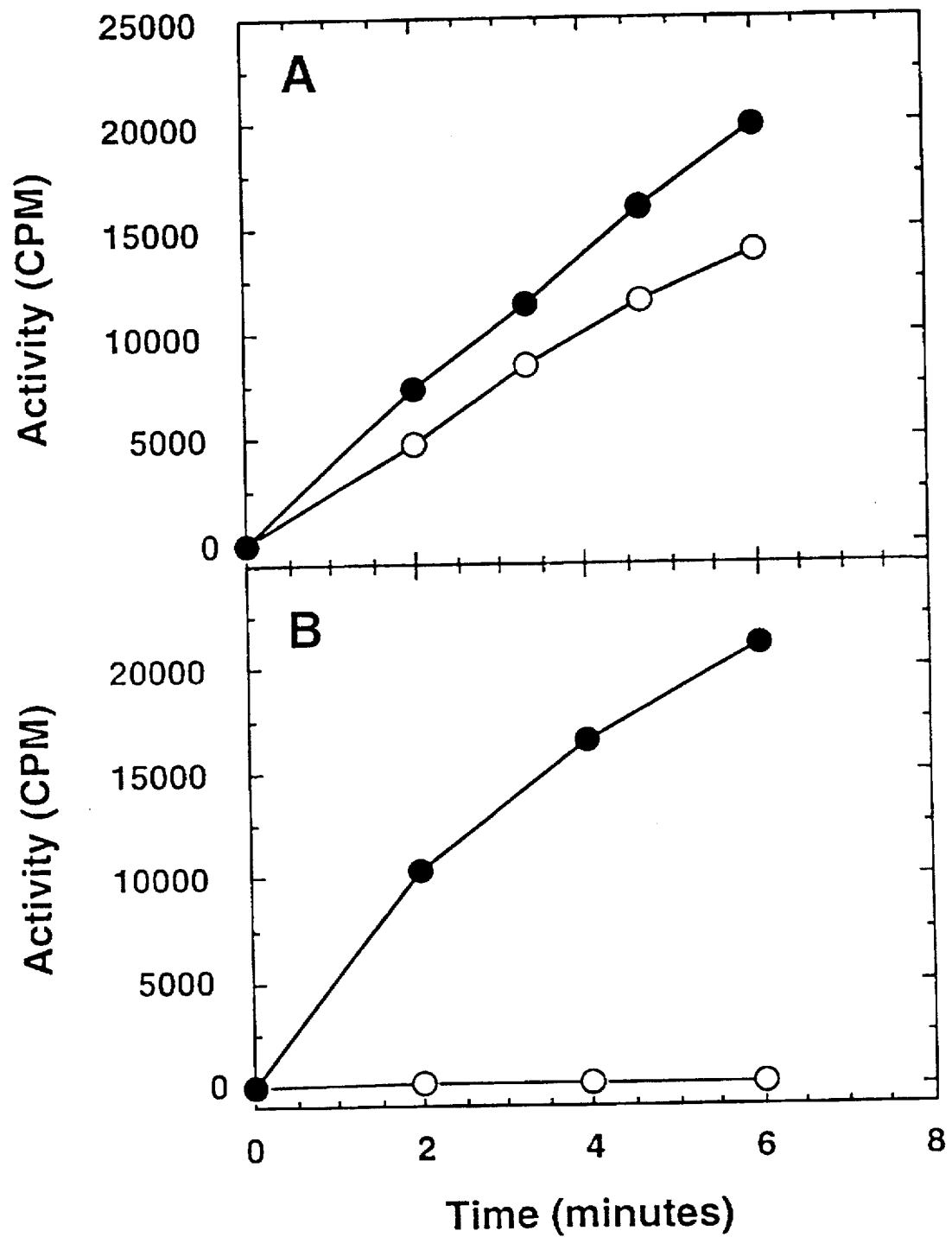
FIGS. 6A and 6B consist of graphs illustrating tRNA charging activity of TB GST-IleRS fusion protein affinity purified from pJM109/pGX-56 cells (FIG. 6A) or tRNA charging activity of *E. coli* IleRS protein purified from MV1184(pKS21) cells (FIG. 6B), with total tRNA from *E. coli* (filled circles) or from yeast (open circles) as substrate. ("TB" is used for "*M. tuberculosis*"; "GST" is glutathione S-transferase of *Schistosoma japonicum*.)

In the experiments illustrated in FIGS. 6A and 6B, the concentrations of purified enzymes were ~50 nM. *E. coli* IleRS was purified by DEAE chromatography to 90% homogeneity as determined by SDS-PAGE. TB GST-IleRS fusion protein was affinity purified as described in Example 8.

EXAMPLE 8

Partial Purification of the *M. tuberculosis* IleRS Protein from *E. coli*

DH5α cells containing construct pKS-56 were grown at 37° C. in 500 ml of LB plus ampicillin to a cell density corresponding to an $OD_{600}$ of 0.6. IPTG was added to a final concentration of 1 mM and the cells were incubated with vigorous shaking for another 4 hours and harvested by centrifugation for 10 minutes at 6000 rpm. The cell pellet was resuspended in 25 ml of lysis buffer and lysed as described above. The clarified extract was brought to 45% ammonium sulfate. Following centrifugation, the resuspended 45% ammonium sulfate precipitate was applied to a MonoQ anion exchange column (HR 10/6, Pharmacia) equilibrated with buffer A (50 mM $KPO_4$, pH 7.5). The column was washed with 10 column volumes, followed by elution with a linear salt gradient from 0 to 0.5M NaCl in buffer A. Six-ml fractions were collected and tested for aminoacylation activity using yeast tRNA as substrate. Fractions containing the activity were concentrated using a Centricon C-3 (Amicon).

Purification of the GST-IleRS Fusion Protein Expressed from pGX-56

JM109 cells containing plasmid pGX-56 were grown in LB plus ampicillin at 37° C. to mid-log phase. IPTG was added to 1 mM and the cells were shifted to 18° C. with vigorous shaking for 72 hours. The cell pellet was treated as above and the clarified extract was loaded onto a glutathione-Sepharose column (Pharmacia) equilibrated with PBS (phosphate buffered saline) containing 2 mM dithiothreitol. Bound proteins were eluted with 10 mM reduced gluthathione and concentrated in a Centricon C-3 (Amicon). Protein concentrations were determined by the Bradford assay. Thrombin cleavage was carried out at room temperature in 50 mM Tris-HCl pH 7.5, 150 mM NaCl, 2.5 mM $CaCl_2$ and 2 mM dithiothreitol for 16 hours.

$K_m$ Determination $K_m$ values for isoleucine were determined for purified TB GST-IleRS fusion protein with or without thrombin cleavage in the presence of either 200 μM of total yeast tRNA or 300 μM of total *E. coli* tRNA (saturating concentrations of tRNA substrate). Isoleucine concentrations were varied from 0.25 to 32 μM. The enzyme concentration was 6.5 nM. Reaction volumes were 50 μl. Aminoacylation assays were performed as described above (Example 7).

EXAMPLE 9

Pseudomonic Acid (PMA) Rescue

*E. coli* strains DH5α or Novablue (Novagen) were transformed with pBSKS(+), pGEX-4T-2, pKS21, pKS-56 or pGEX-56. Transformants were grown in LB plus ampicillin (100 μg/ml) overnight at 37° C., diluted 1:20 into LB plus ampicillin containing 25 μM IPTG and grown for 5–8 hours at 30° C., then diluted in LB plus ampicillin containing 25 μM IPTG to an $A_{600}$ of 0.1. Ten μl of each culture were placed in a 96-well microtiter plate, to which was added 100 μl of medium (LB plus ampicillin containing IPTG with varying amounts of pseudomonic acid). The plate was incubated at 30° C. (shaking at 200 rpm) for 36–40 hours, and $A_{600}$ values were read on a Spectramax plate reader (Molecular Devices). The percent relative growth of each strain was measured as the ratio of $A_{600}$ obtained for that strain in the absence of PMA. Results are shown in FIG. 11.

DH5α cells expressing wild-type IleRS on a plasmid (pKS21) were completely inhibited in LB plus ampicillin media containing 40 μg/ml PMA, while the cells expressing the *M. tuberculosis* IleRS gene (on pKS-56) showed no inhibition of growth (FIG. 11). Identical results were obtained for the TB GST-IleRS fusion construct, pGX-56. *E. coli* cells harboring pKS-56 continued to grow even in LB plus ampicillin with 640 μg/ml PMA (higher concentrations were not tested). Thus, the *M. tuberculosis* IleRS enzyme rescues *E. coli* from inhibition by PMA, presumably by providing tRNA aminoacylation activity in trans as suggested by the complementation experiments described above. The resistance of *M. tuberculosis* IleRS to PMA provides a rescue assay in which a cell which is sensitive to a compound of interest (such as PMA) is transformed with a mycobacterial IleRS, exposed to the compound, and maintained under conditions where the mycobacterial IleRS is expressed. If the effect of the compound is specific for the IleRS of the host cell, the mycobacterial IleRS will be able to rescue the host cells from the effect of the compound.

which can be used in the production of tester strains comprising recombinant mycobacterial aminoacyl-tRNA synthetase genes by methods analogous to those described herein. The approaches described herein, including, but not

TABLE 1

Strategy for design of oligonucleotide primers

| Amino Acid Sequence | Primer | Oligonucleotide Sequence | Direction |
|---|---|---|---|
| Region 1 | | | |
| GWDTHG(LV)P (SEQ ID NO:20) | KY-16 (SEQ ID NO:4) | GGITGGGAYACICAYGGISTICC | → |
| GWDCHG(Lv)P (SEQ ID NO:21) | KY-17 (SEQ ID NO:5) | GGITGGGAYTGYCAYGGICTICC | → |
| Region 2 | | | |
| (FY)(Mi)ES(Tvc)WW(VA) (FL)KQ (SEQ ID NO:22) | KY-37 (SEQ ID NO:6) | TWYATGGARTCIACITGGTGGGYITTIAARCA | → |
| Region 3 | | | |
| RQR(Yt)WG(IV)P(IM) (SEQ ID NO:23) | KY-18 (SEQ ID NO:7) | CGICARCGITAYTGGGGIRTICCIAT | → |
| R(Ns)R(YF)WG(Tn)P(IL) (SEQ ID NO:24) | KY-19 (SEQ ID NO:7) | CGIAAYCGITWYTGGGGIACICCIMT | → |
| Region 4 | | | |
| EG(ILsh)DQ(Th)RGWF (SEQ ID NO:25) | KY-20 (SEQ ID NO:9) | RAACCAICCICGIGTYTGRTCIWWICCYTC | ← |
| Region 5 | | | |
| WTTTPWTLP (SEQ ID NO:26) | KY-36 (SEQ IS NO:10) | GGIARIGTCCAIGGIGTIGTIGTCCA | ← |

The one letter code for amino acids is used to give the amino acid sequence of four regions that are well conserved among *E. coli* (Webster, T. A., et al., Science 226:1315–1317 (1984)), *M. thermoautotrophicum* (Jenal, U., et al., J. Biol. Chem. 266:10570–10577 (1991)), *S. cerevisiae* (Englisch, U., et al., Biol. Chem. Hoppe-Seyler 368:971–979 (1987) and Martindale, D. W., et al., Curr. Genet. 15.: 99–106 (1989)), and *T. thermophila* (Csank, C., et al., J. Biol. Chem. 267:4592–4599 (1992)) and *T. thermophilus* isoleucyl-tRNA synthetases. Variations in the amino acid residue at a given position are indicated by enclosing the residues in a parentheses. Lower case letters indicate amino acid residues whose codons are not complementary to the corresponding degenerate primer. For the oligonucleotide sequence, M = A or C; Y = C or T; R = A or G; W = A or T; S = G or C; I = inosine. Primers KY-16, -17 and -20 have an additional GCGAATTC, and primers KY-18 and -19 have an additional GCGAATT, at the 5' end to facilitate release of amplified fragments which have been cloned into a vector.

TABLE 2

| PCR FRAGMENT | PRIMER COMBINATIONS | EXPECTED SIZE | PRODUCT OBTAINED |
|---|---|---|---|
| Ile-1A | KIYO-16 + KIYO-20 | 1.5 kbp | No |
| Ile-1B | KIYO-17 + KIYO-20 | 1.5 kbp | Yes |
| Ile-2A | KIYO-18 + KIYO-20 | 0.3 kbp | No |
| Ile-2B | KIYO-19 + KIYO-20 | 0.3 kbp | Yes |
| Ile-3 | KIYO-37 + KIYO-36 | 0.3 kbp | No |
| Ile-4A | KIYO-16 + KIYO-36 | 0.45 kbp | Yes |
| Ile-4B | KIYO-17 + KIYO-36 | 0.45 kbp | Yes |
| Ile-5 | KIYO-37 + KIYO-20 | 1.3 kbp | Yes |

Related Mycobacterial Aminoacyl tRNA Synthetases and Tester Strains

In addition to the gene encoding isoleucyl-tRNA synthetase described herein, genes encoding methionyl-, leucyl-, seryl-, and tyrosyl-tRNA synthetases from *M. tuberculosis* have been isolated and sequenced as described in U.S. Ser. No. 08/305,766 (Attorney Docket No. CPI94-05), U.S. Ser. No. 08/305,171 (Attorney Docket No. CPI94-06), U.S. Ser. No. 08/305,172 (Attorney Docket No. CPI94-07), and U.S. Ser. No. 08/305,181 (Attorney Docket No. CPI94-20), respectively, all filed on Sep. 13, 1994, and in U.S. Ser. No. 08/390,453 (Attorney Docket No. CPI94-20A), filed on Feb. 17, 1995, and U.S. Ser. No. 08/451,774 (Attorney Docket No. CPI94-06A), filed concurrently herewith, the teachings of which are each incorporated herein by reference in their entirety. These isolated genes are representatives of a broader class of mycobacterial aminoacyl-tRNA synthetase genes, including synthetase genes encoding enzymes specific for each amino acid and derived from various species of mycobacteria, each of which gene can be used to express mycobacterial aminoacyl-tRNA synthetase protein, with utilities corresponding to those described herein, and limited to, the approaches to isolate and manipulate the methionyl-, leucyl-, seryl-, isoleucyl- and tyrosyl-tRNA synthetase genes of *M. tuberculosis*, to construct vectors and host strains, to produce and use the enzymes, to produce antibodies, etc., can be applied to other aminoacyl-tRNA synthetases of the genus Mycobacterium.

Equivalents

Those skilled in the art will know, or be able to ascertain using no more than routine experimentation, many equivalents to the specific embodiments of the invention described herein. These and all other equivalents are intended to be encompassed by the following claims.

5,756,327

---

What is claimed is:

1. An isolated nucleic acid encoding an isoleucyl-tRNA synthetase of the genus Mycobacterium which shares at least about 86% amino acid sequence identity with SEQ ID NO: 2.

2. An essentially pure nucleic acid which hybridizes under stringent temperature conditions to DNA having the sequence SEQ ID NO: 1 and encodes an isoleucyl-tRNA synthetase of the genus Mycobacterium.

3. An isolated, recombinant nucleic acid which encodes a isoleucyl-tRNA synthetase of *Mycobacterium tuberculosis*.

4. An essentially pure nucleic acid which hybridizes under stringent temperature conditions to DNA having SEQ ID NO: 1 and encodes an isoleucyl-tRNA synthetase of *Mycobacterium tuberculosis*.

5. An essentially pure nucleic acid which encodes the amino acid sequence SEQ ID NO: 2.

6. A recombinant nucleic acid vector comprising nucleic acid which encodes a mycobacterial isoleucyl-tRNA synthetase and which hybridizes to DNA having SEQ ID NO: 1 under stringent temperature conditions.

7. A recombinant nucleic acid vector comprising the nucleic acid of claim 1.

8. A recombinant nucleic acid vector of claim 6 wherein the isoleucyl-tRNA synthetase is an isoleucyl-tRNA synthetase of *Mycobacterium tuberculosis*.

9. A recombinant DNA vector comprising DNA which encodes an isoleucyl-tRNA synthetase of *Mycobacterium tuberculosis*.

10. A host cell comprising the nucleic acid of claim 1.

11. A host cell of claim 10 in which the recombinant mycobacterial isoleucyl-tRNA synthetase is a *Mycobacterium tuberculosis* isoleucyl-tRNA synthetase.

12. An expression vector comprising a nucleic acid encoding a fusion protein comprising a mycobacterial isoleucyl-tRNA synthetase, wherein said nucleic acid comprises a coding sequence for the mycobacterial isoleucyl-tRNA synthetase, which coding sequence hybridizes to DNA having SEQ ID NO: 1 under stringent temperature conditions, and wherein the coding sequence is under the control of transcription signals and is linked to appropriate translation signals for expression in a suitable host cell.

13. A tester strain comprising host cells containing a recombinant mycobacterial isoleucyl-tRNA synthetase gene which hybridizes under stringent temperature conditions to DNA having SEQ ID NO: 1, and which expresses a mycobacterial isoleucyl-tRNA synthetase which complements or substitutes in function for a host isoleucyl-tRNA synthetase gene.

14. A tester strain of claim 13 in which a host gene encoding an isoleucyl-tRNA synthetase has been lost or has been altered relative to wild type so as to make no gene product, a gene product which is inactive, or a gene product which can be conditionally made inactive.

15. A tester strain of claim 13 in which the host cells are non-mycobacterial cells.

16. The tester strain of claim 13 in which the recombinant mycobacterial isoleucyl-tRNA synthetase gene which expresses a mycobacterial isoleucyl-tRNA synthetase is a *Mycobacterium tuberculosis* isoleucyl-tRNA synthetase gene.

17. A method for producing active mycobacterial isoleucyl-tRNA synthetase comprising the following steps:
   a) constructing a recombinant nucleic acid vector comprising a recombinant nucleic acid which hybridizes under stringent temperature conditions to DNA having the sequence SEQ ID NO: 1 and encodes an isoleucyl-tRNA synthetase of the genus Mycobacterium, wherein the nucleic acid is under the control of transcription signals and is linked to appropriate translation signals;
   b) introducing the vector into suitable host cells which support the replication of the vector; and
   c) maintaining the host cells under conditions in which mycobacterial isoleucyl-tRNA synthetase is expressed.

18. A method for producing isolated, recombinant mycobacterial isoleucyl-tRNA synthetase comprising the following steps:
   a) providing host cells comprising a recombinant nucleic acid which hybridizes under stringent temperature conditions to DNA having the sequence SEQ ID NO: 1 and encodes an isoleucyl-tRNA synthetase of the genus Mycobacterium;
   b) maintaining the host cells under conditions in which the gene is expressed; and
   c) isolating mycobacterial isoleucyl-tRNA synthetase from the host cells.

19. An isolated nucleic acid comprising a nucleic acid having a sequence complementary to a DNA strand having SEQ ID NO: 1 or to an RNA counterpart of SEQ ID NO: 1.

20. An essentially pure nucleic acid which hybridizes under stringent temperature conditions to DNA having the sequence SEQ ID NO: 3 and which encodes an isoleucyl-tRNA synthetase of the genus Mycobacterium.

21. The essentially pure nucleic acid of claim 2 wherein the hybridization is performed at 65° C. in 5X Denhardt's solution, 10 mM EDTA, 20 µg/ml salmon sperm DNA, 5X SSC and 0.5% SDS, with three washes in 2X SSC, 0.1% SDS at 65°.

22. A host cell comprising the nucleic acid of claim 2.

23. An isolated nucleic acid, wherein said nucleic acid encodes a protein comprising an isoleucyl-tRNA synthetase which is encoded by pNBS-ile as deposited under ATCC Accession No. 98221, or by a derivative of pNBS-ile in which G at position 640 is altered to A, or by a derivative of pNBS-ile in which G at position 670 is altered to A.

24. The isolated nucleic acid of claim 23, wherein the protein is a fusion protein.

25. The isolated nucleic acid of claim 23, which is essentially pure.

26. A host cell comprising a recombinant nucleic acid, wherein said nucleic acid encodes a protein comprising an isoleucyl-tRNA synthetase which is encoded by pNBS-ile as deposited under ATCC Accession No. 98221 or by a derivative of pNBS-ile in which G at position 640 is altered to A, or by a derivative of pNBS-ile in which G at position 670 is altered to A.

27. A method for producing a protein comprising an isoleucyl-tRNA synthetase, comprising maintaining a host cell of claim 26 under conditions suitable for expression of said protein, whereby said protein is produced.

28. Plasmid pNBS-ile of host cells deposited under ATCC Accession No. 98221.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
( A ) LENGTH: 3905 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 640..3774

( x i ) SEQUENCE DESCRIPTION: SEQ ID NO:1:

```
TTGCGCTGAG  TCGTCACCAG  ATCAGCCTCT  TGGATCGACC  GCTACGGACG  GACCAACTCG      60
GTTCAGTCCA  TATGTGCTCG  TTTTGATTTC  CGTCCTCGCT  TGCAACTCCG  TCTAGGAGGT     120
CAGATCATGA  CCGCTGCTCT  GCACAATGAC  GTAGTAACCG  TAGCTTCGGC  CCCCAAGCTG     180
CGGGTGGTGC  GGGATGTGCC  CCCGGCCCCC  GCGTCCAAGA  AGGTTGCTCG  CCGGCTCGAN     240
GNGCAGCCTT  TCGGCACCGG  AGGGGACCCG  CTGGTCGACG  GGGCAGCTCG  TTTGCTGAGC     300
ATTCCGCTGC  GCCACCTCTA  CGCCGCGTTG  TGGCGCGTCG  GGCTGCTCGA  GGTCCAGGCC     360
TAGTCCGATG  GGCAGGCAGC  CGACCTTGCG  CCGCGATGTG  GATTTGCGGC  GCTGGGCGAC     420
AATCCCCGTA  GAATCAGGGG  AACGGCATCG  ATCCGGCGAT  CACCGGGGAG  CCTTCGGAAG     480
AACGGCCGGT  TAGGCCAGTA  GAACCGAACG  GGTTGGCCCG  TCACAGCCTC  AAGTCGAGCG     540
GCCGCGCATC  GGCGTGGCAA  GCGGGGTGGT  ACCGCGGCGT  TCGCGCACCG  GCGTGGCGTC     600
GTCCCCGAGC  CTGGATTGCA  GGCGACGCAG  TGCCGAACG GTG CTG GGG CCT GGG          654
                                             Met Leu Gly Pro Gly
                                              1               5
```

```
GAG ACG ACG CGC AAA GTG ACC GAT AAC GCA TAT CCA AAG CTG GCC GGC           702
Glu Thr Thr Arg Lys Xaa Thr Asp Asn Ala Tyr Pro Lys Leu Ala Gly
              10                  15                  20

GGG GCA CCC GAC CTC CCG GCA CTC GAA CTC GAG GTC CTC GAC TAC TGG           750
Gly Ala Pro Asp Leu Pro Ala Leu Glu Leu Glu Val Leu Asp Tyr Trp
          25                  30                  35

TCC CGT GAC GAC ACC TTC CGG GCC AGC ATT GCT CGC CGC GAT GGC GCC           798
Ser Arg Asp Asp Thr Phe Arg Ala Ser Ile Ala Arg Arg Asp Gly Ala
      40                  45                  50

CCC GAG TAT GTG TTC TAT GAC GGG CCG CCG TTT GCC AAC GGT CTG CCG           846
Pro Glu Tyr Val Phe Tyr Asp Gly Pro Pro Phe Ala Asn Gly Leu Pro
  55                  60                  65

CAT TAT GGG CAC CTG CTC ACC GGC TAC GTC AAA GAC ATC GTG CCG CGA           894
His Tyr Gly His Leu Leu Thr Gly Tyr Val Lys Asp Ile Val Pro Arg
 70                  75                  80                  85

TAT CGC ACT ATG CGC GGT TAC AAG GTG GAG CGT CGC TTC GGC TGG GAC           942
Tyr Arg Thr Met Arg Gly Tyr Lys Val Glu Arg Arg Phe Gly Trp Asp
                 90                  95                 100

ACT CAC GGG CTG CCC GCC GAA CTC GAA GTC GAG CGC CAG CTT GGC ATC           990
Thr His Gly Leu Pro Ala Glu Leu Glu Val Glu Arg Gln Leu Gly Ile
            105                 110                 115

ACT GAC AAA TCC CAG ATC GAG GCC ATG GGT ATC GCC GCC TTC AAC GAT          1038
Thr Asp Lys Ser Gln Ile Glu Ala Met Gly Ile Ala Ala Phe Asn Asp
        120                 125                 130
```

-continued

| | | | | | | | | | | | | | | | | |
|---|---|---|---|---|---|---|---|---|---|---|---|---|---|---|---|---|
| GCC | TGC | CGC | GCA | TCC | GTG | TTG | CGC | TAC | ACC | GAC | GAG | TGG | CAG | GCG | TAT | 1086 |
| Ala | Cys | Arg | Ala | Ser | Val | Leu | Arg | Tyr | Thr | Asp | Glu | Trp | Gln | Ala | Tyr | |
| | 135 | | | | 140 | | | | | 145 | | | | | | |
| GTA | ACT | CGG | CAA | GCT | CGC | TGG | GTC | GAC | TTC | GAC | AAC | GAT | TAC | AAG | ACG | 1134 |
| Val | Thr | Arg | Gln | Ala | Arg | Trp | Val | Asp | Phe | Asp | Asn | Asp | Tyr | Lys | Thr | |
| 150 | | | | | 155 | | | | | 160 | | | | | 165 | |
| CTC | GAT | CTG | GCT | TAC | ATG | GAG | TCG | GTG | ATT | TGG | GCC | TTC | AAA | CAG | TTG | 1182 |
| Leu | Asp | Leu | Ala | Tyr | Met | Glu | Ser | Val | Ile | Trp | Ala | Phe | Lys | Gln | Leu | |
| | | | | 170 | | | | | 175 | | | | | 180 | | |
| TGG | GAC | AAG | GGC | CTG | GCC | TAC | GAG | GGC | TAC | CGG | GTG | CTG | CCG | TAC | TGC | 1230 |
| Trp | Asp | Lys | Gly | Leu | Ala | Tyr | Glu | Gly | Tyr | Arg | Val | Leu | Pro | Tyr | Cys | |
| | | | 185 | | | | | 190 | | | | | 195 | | | |
| TGG | CGC | GAC | GAA | ACT | CCG | CTG | TCG | AAT | CAC | GAA | CTG | CGG | ATG | GAC | GAC | 1278 |
| Trp | Arg | Asp | Glu | Thr | Pro | Leu | Ser | Asn | His | Glu | Leu | Arg | Met | Asp | Asp | |
| | | 200 | | | | | 205 | | | | | 210 | | | | |
| GAC | GTC | TAC | CAA | AGC | CGC | CAA | GAT | CCC | GCG | GTA | ACG | GTG | GGC | TTC | AAG | 1326 |
| Asp | Val | Tyr | Gln | Ser | Arg | Gln | Asp | Pro | Ala | Val | Thr | Val | Gly | Phe | Lys | |
| | | 215 | | | | | 220 | | | | | 225 | | | | |
| GTG | GTG | GGT | GGC | CAA | CCA | GAC | AAC | GGG | CTA | GAC | GGT | GCC | TAC | TTG | CTG | 1374 |
| Val | Val | Gly | Gly | Gln | Pro | Asp | Asn | Gly | Leu | Asp | Gly | Ala | Tyr | Leu | Leu | |
| 230 | | | | | 235 | | | | | 240 | | | | | 245 | |
| GTG | TGG | ACG | ACG | ACT | CCG | TGG | ACC | CTG | CCG | TCG | AAC | CTC | GCA | GTT | GCG | 1422 |
| Val | Trp | Thr | Thr | Thr | Pro | Trp | Thr | Leu | Pro | Ser | Asn | Leu | Ala | Val | Ala | |
| | | | | 250 | | | | | 255 | | | | | 260 | | |
| GTA | AGC | CCG | GAC | ATC | ACC | TAC | GTA | CAG | GTC | CAG | GCG | GGC | GAT | CGC | CGT | 1470 |
| Val | Ser | Pro | Asp | Ile | Thr | Tyr | Val | Gln | Val | Gln | Ala | Gly | Asp | Arg | Arg | |
| | | | 265 | | | | | 270 | | | | | 275 | | | |
| TTC | GTA | CTG | GCC | GAG | GCA | CGG | CTG | GCC | CGT | TAC | GCC | CGC | GAA | CTC | GGT | 1518 |
| Phe | Val | Leu | Ala | Glu | Ala | Arg | Leu | Ala | Arg | Tyr | Ala | Arg | Glu | Leu | Gly | |
| | | 280 | | | | | 285 | | | | | 290 | | | | |
| GAA | GAG | CCC | GTG | GTG | CTC | GGC | ACC | TAT | CGC | GGC | GCC | GAA | CTG | CTG | GGC | 1566 |
| Glu | Glu | Pro | Val | Val | Leu | Gly | Thr | Tyr | Arg | Gly | Ala | Glu | Leu | Leu | Gly | |
| | 295 | | | | | 300 | | | | | 305 | | | | | |
| ACC | CGC | TAC | CTG | CCG | CCG | TTT | GCC | TAT | TTC | ATG | GAC | TGG | CCC | AAC | GCT | 1614 |
| Thr | Arg | Tyr | Leu | Pro | Pro | Phe | Ala | Tyr | Phe | Met | Asp | Trp | Pro | Asn | Ala | |
| 310 | | | | | 315 | | | | | 320 | | | | | 325 | |
| TTT | CAG | GTG | CTA | GCA | GGC | GAC | TTT | GTA | ACG | ACC | GAC | GAT | GGC | ACC | GGC | 1662 |
| Phe | Gln | Val | Leu | Ala | Gly | Asp | Phe | Val | Thr | Thr | Asp | Asp | Gly | Thr | Gly | |
| | | | | 330 | | | | | 335 | | | | | 340 | | |
| ATC | GTG | CAT | ATG | GCA | CCG | GCC | TAT | GGT | GAG | GAC | GAC | ATG | GTG | GTC | GCG | 1710 |
| Ile | Val | His | Met | Ala | Pro | Ala | Tyr | Gly | Glu | Asp | Asp | Met | Val | Val | Ala | |
| | | | 345 | | | | | 350 | | | | | 355 | | | |
| GAG | GCG | GTC | GGT | ATC | GCG | CCG | GTG | ACT | CCG | GTC | GAC | TCC | AAG | GGA | CGC | 1758 |
| Glu | Ala | Val | Gly | Ile | Ala | Pro | Val | Thr | Pro | Val | Asp | Ser | Lys | Gly | Arg | |
| | | 360 | | | | | 365 | | | | | 370 | | | | |
| TTC | GAC | GTC | ACC | GTT | GCC | GAT | TAC | CAA | GGG | CAG | CAT | GTC | TTT | GAC | GCC | 1806 |
| Phe | Asp | Val | Thr | Val | Ala | Asp | Tyr | Gln | Gly | Gln | His | Val | Phe | Asp | Ala | |
| 375 | | | | | 380 | | | | | 385 | | | | | | |
| AAC | GCG | CAG | ATC | GTC | CGG | GAC | CTG | AAG | ACC | CAA | AGC | GGC | CCG | GCT | GCG | 1854 |
| Asn | Ala | Gln | Ile | Val | Arg | Asp | Leu | Lys | Thr | Gln | Ser | Gly | Pro | Ala | Ala | |
| 390 | | | | | 395 | | | | | 400 | | | | | 405 | |
| GTG | AAT | GGC | CCA | GTG | TTG | ATT | CGT | CAC | GAA | ACC | TAC | GAG | CAC | CCT | TAC | 1902 |
| Val | Asn | Gly | Pro | Val | Leu | Ile | Arg | His | Glu | Thr | Tyr | Glu | His | Pro | Tyr | |
| | | | | 410 | | | | | 415 | | | | | 420 | | |
| CCA | CAC | TGC | TGG | CGA | TGC | CGT | AAC | CCG | CTG | ATC | TAC | CGG | TCG | GTG | TCG | 1950 |
| Pro | His | Cys | Trp | Arg | Cys | Arg | Asn | Pro | Leu | Ile | Tyr | Arg | Ser | Val | Ser | |
| | | | 425 | | | | | 430 | | | | | 435 | | | |
| TCG | TGG | TTC | GTC | AGG | GTG | ACG | GAC | TTC | CGA | GAC | CGC | ATG | GTG | GAG | CTA | 1998 |
| Ser | Trp | Phe | Val | Arg | Val | Thr | Asp | Phe | Arg | Asp | Arg | Met | Val | Glu | Leu | |
| | | 440 | | | | | 445 | | | | | 450 | | | | |

| | | | | | | | | | | | | | | | | |
|---|---|---|---|---|---|---|---|---|---|---|---|---|---|---|---|---|
| AAC | CAG | CAG | ATC | ACG | TGG | TAT | CCC | GAA | CAC | GTC | AAG | GAC | GGC | CAG | TTC | 2046 |
| Asn | Gln | Gln | Ile | Thr | Trp | Tyr | Pro | Glu | His | Val | Lys | Asp | Gly | Gln | Phe | |
| 455 | | | | | 460 | | | | | | 465 | | | | | |
| GGC | AAG | TGG | CTG | CAG | GGC | GCC | CGC | GAT | TGG | TCG | ATC | TCC | CGG | AAT | CGC | 2094 |
| Gly | Lys | Trp | Leu | Gln | Gly | Ala | Arg | Asp | Trp | Ser | Ile | Ser | Arg | Asn | Arg | |
| 470 | | | | | 475 | | | | 480 | | | | | | 485 | |
| TAC | TGG | GGT | ACC | CCG | ATT | CCG | GTA | TGG | AAG | TCC | GAC | GAC | CCG | GCC | TAC | 2142 |
| Tyr | Trp | Gly | Thr | Pro | Ile | Pro | Val | Trp | Lys | Ser | Asp | Asp | Pro | Ala | Tyr | |
| | | | | 490 | | | | | 495 | | | | | 500 | | |
| CCG | CGC | ATC | GAT | GTC | TAC | GGC | AGC | CTC | GAC | GAG | CTG | GAG | CGC | GAC | TTC | 2190 |
| Pro | Arg | Ile | Asp | Val | Tyr | Gly | Ser | Leu | Asp | Glu | Leu | Glu | Arg | Asp | Phe | |
| | | | 505 | | | | | 510 | | | | | 515 | | | |
| GGC | GTA | CGC | CCG | GCC | AAT | TTG | CAC | CGG | CCC | TAC | ATC | GAC | GAG | CTC | ACC | 2238 |
| Gly | Val | Arg | Pro | Ala | Asn | Leu | His | Arg | Pro | Tyr | Ile | Asp | Glu | Leu | Thr | |
| | | 520 | | | | | 525 | | | | | 530 | | | | |
| CGT | CCC | AAC | CCA | GAC | GAT | CCG | ACT | GGC | CGT | AGC | ACG | ATG | CGA | CGC | ATT | 2286 |
| Arg | Pro | Asn | Pro | Asp | Asp | Pro | Thr | Gly | Arg | Ser | Thr | Met | Arg | Arg | Ile | |
| | | 535 | | | | | 540 | | | | | 545 | | | | |
| CCC | GAT | GTG | CTC | GAC | GTG | TGG | TTC | GAC | TCG | GGA | TCC | ATG | CCG | TAT | GCC | 2334 |
| Pro | Asp | Val | Leu | Asp | Val | Trp | Phe | Asp | Ser | Gly | Ser | Met | Pro | Tyr | Ala | |
| 550 | | | | | 555 | | | | | 560 | | | | | 565 | |
| CAG | GTG | CAC | TAC | CCG | TTC | GAG | AAC | CTG | GAT | TGG | TTC | CAG | GGA | CAC | TAC | 2382 |
| Gln | Val | His | Tyr | Pro | Phe | Glu | Asn | Leu | Asp | Trp | Phe | Gln | Gly | His | Tyr | |
| | | | | 570 | | | | | 575 | | | | | 580 | | |
| CCC | GGC | GAC | TTC | ATC | GTC | GAG | TAC | ATC | GGG | CAG | ACC | CGT | GGC | TGG | TTT | 2430 |
| Pro | Gly | Asp | Phe | Ile | Val | Glu | Tyr | Ile | Gly | Gln | Thr | Arg | Gly | Trp | Phe | |
| | | | 585 | | | | | 590 | | | | | 595 | | | |
| TAC | ACA | CTG | CAT | GTG | TTG | GCG | ACC | GCG | CTC | TTT | GAC | CGG | CCG | GCA | TTC | 2478 |
| Tyr | Thr | Leu | His | Val | Leu | Ala | Thr | Ala | Leu | Phe | Asp | Arg | Pro | Ala | Phe | |
| | | 600 | | | | | 605 | | | | | 610 | | | | |
| AAA | ACC | TGT | GTG | GCG | CAT | GGG | ATT | GTC | CTT | GGT | TTC | GAT | GGC | CAG | AAG | 2526 |
| Lys | Thr | Cys | Val | Ala | His | Gly | Ile | Val | Leu | Gly | Phe | Asp | Gly | Gln | Lys | |
| 615 | | | | | 620 | | | | | 625 | | | | | | |
| ATG | AGC | AAG | TCG | GTG | CGC | AAC | TAT | CCA | GAC | GTA | ACA | GAG | GTG | TTC | GAT | 2574 |
| Met | Ser | Lys | Ser | Val | Arg | Asn | Tyr | Pro | Asp | Val | Thr | Glu | Val | Phe | Asp | |
| 630 | | | | | 635 | | | | | 640 | | | | | 645 | |
| CGC | GAC | GGC | TCC | GAC | GCC | ATG | CGG | TGG | TTC | CTG | ATG | GCA | TCG | CCG | ATT | 2622 |
| Arg | Asp | Gly | Ser | Asp | Ala | Met | Arg | Trp | Phe | Leu | Met | Ala | Ser | Pro | Ile | |
| | | | | 650 | | | | | 655 | | | | | 660 | | |
| CTG | CGC | GGC | GGC | AAC | CTG | ATC | GTC | ACT | GAG | CAA | GGA | ATT | CGC | GAC | GGT | 2670 |
| Leu | Arg | Gly | Gly | Asn | Leu | Ile | Val | Thr | Glu | Gln | Gly | Ile | Arg | Asp | Gly | |
| | | | 665 | | | | | 670 | | | | | 675 | | | |
| GTG | CGA | CAA | GTC | CTG | CTG | CCC | CTG | TGG | AAC | ACC | TAC | AGC | TTC | CTG | GCG | 2718 |
| Val | Arg | Gln | Val | Leu | Leu | Pro | Leu | Trp | Asn | Thr | Tyr | Ser | Phe | Leu | Ala | |
| | | 680 | | | | | 685 | | | | | 690 | | | | |
| CTG | TAT | GCA | CCG | AAA | GTC | GGT | ACC | TGG | CGC | GTC | GAT | TCG | GTG | CAC | GTG | 2766 |
| Leu | Tyr | Ala | Pro | Lys | Val | Gly | Thr | Trp | Arg | Val | Asp | Ser | Val | His | Val | |
| | 695 | | | | | 700 | | | | | 705 | | | | | |
| CTG | GAT | CGC | TAT | ATC | CTG | GCC | AAG | CTG | GCG | GTG | CTG | CGC | GAC | GAC | CTC | 2814 |
| Leu | Asp | Arg | Tyr | Ile | Leu | Ala | Lys | Leu | Ala | Val | Leu | Arg | Asp | Asp | Leu | |
| 710 | | | | | 715 | | | | | 720 | | | | | 725 | |
| AGC | GAG | TCG | ATG | GAA | GTT | TAC | GAT | ATT | CCC | GGT | GCC | TGT | GAA | CAT | TTG | 2862 |
| Ser | Glu | Ser | Met | Glu | Val | Tyr | Asp | Ile | Pro | Gly | Ala | Cys | Glu | His | Leu | |
| | | | | 730 | | | | | 735 | | | | | 740 | | |
| CGT | CAG | TTC | ACT | GAG | GCG | TTG | ACT | AAT | TGG | TAT | GTG | CGA | CGG | TCG | CGT | 2910 |
| Arg | Gln | Phe | Thr | Glu | Ala | Leu | Thr | Asn | Trp | Tyr | Val | Arg | Arg | Ser | Arg | |
| | | | 745 | | | | | 750 | | | | | 755 | | | |
| TCG | CGG | TTC | TGG | GCA | GAA | GAC | GCC | GAT | GCC | ATC | GAC | ACG | CTA | CAC | ACC | 2958 |
| Ser | Arg | Phe | Trp | Ala | Glu | Asp | Ala | Asp | Ala | Ile | Asp | Thr | Leu | His | Thr | |
| | | | 760 | | | | | 765 | | | | 770 | | | | |

```
GTG TTG GAG GTG ACC ACG AGG CTG GCC GCC CCG CTG CTT CCG CTG ATC        3006
Val Leu Glu Val Thr Thr Arg Leu Ala Ala Pro Leu Leu Pro Leu Ile
    775             780             785

ACC GAG ATA ATC TGG CGT GGT CTG ACA CGC GAG CGA TCG GTG CAC CTG        3054
Thr Glu Ile Ile Trp Arg Gly Leu Thr Arg Glu Arg Ser Val His Leu
790             795             800                 805

ACG GAC TGG CCA GCG CCC GAC CTG CTG CCG TCG GAT GCC GAC CTG GTC        3102
Thr Asp Trp Pro Ala Pro Asp Leu Leu Pro Ser Asp Ala Asp Leu Val
                810             815                 820

GCC GCG ATG GAC CAG GTC CGC GAC GTG TGC TCG GCG GCA TCC TCS STG        3150
Ala Ala Met Asp Gln Val Arg Asp Val Cys Ser Ala Ala Ser Ser Xaa
            825             830                 835

CGC AAG GCC AAG AAG CTA CGG GTG CGC CTG CCG CTA CCG AAA CTC ATT        3198
Arg Lys Ala Lys Lys Leu Arg Val Arg Leu Pro Leu Pro Lys Leu Ile
        840             845             850

GTG GCA GTT GAG AAT CCG CAA CTT CTG AGG CCG TTC GTC GAC CTC ATT        3246
Val Ala Val Glu Asn Pro Gln Leu Leu Arg Pro Phe Val Asp Leu Ile
855             860             865

GGC GAC GAG CTT AAC GTG AAG CAG GTC GAA CTG ACC GAT GCC ATC GAC        3294
Gly Asp Glu Leu Asn Val Lys Gln Val Glu Leu Thr Asp Ala Ile Asp
870             875             880                 885

ACC TAT GGC CGA TTC GAG CTC ACG GTC AAC GCC CGG GTA GCC GGA CCA        3342
Thr Tyr Gly Arg Phe Glu Leu Thr Val Asn Ala Arg Val Ala Gly Pro
            890             895             900

CGG CTG GGC AAA GAT GTG CAG GCC GCC ATC AAG GCG GTC AAG GCC GGC        3390
Arg Leu Gly Lys Asp Val Gln Ala Ala Ile Lys Ala Val Lys Ala Gly
        905             910             915

GAC GGC GTC ATA AAC CCG GAC GGC ACC TTG TTG GCG GGC CCC GCG GTG        3438
Asp Gly Val Ile Asn Pro Asp Gly Thr Leu Leu Ala Gly Pro Ala Val
        920             925             930

CTG ACG CCC GAC GAG TAC AAC TCC CGG CTG GTG GCC GCC GAC CCG GAG        3486
Leu Thr Pro Asp Glu Tyr Asn Ser Arg Leu Val Ala Ala Asp Pro Glu
935             940             945

TCC ACC GCG GCG TTG CCC GAC GGC GCC GGG CTG GTC GTT CTG GAT GGC        3534
Ser Thr Ala Ala Leu Pro Asp Gly Ala Gly Leu Val Val Leu Asp Gly
950             955             960                 965

ACC GTC ACT GCC GAA CTC GAA GCC GAG GGC TGG GCC AAA GAT CCG ATC        3582
Thr Val Thr Ala Glu Leu Glu Ala Glu Gly Trp Ala Lys Asp Pro Ile
            970             975             980

CGC GAA CTG CAA GAG CTG CGT AAG TCG ACC GGG CTG GAC GTT TCC GAC        3630
Arg Glu Leu Gln Glu Leu Arg Lys Ser Thr Gly Leu Asp Val Ser Asp
        985             990             995

CGC ATC CGG GTG GTG ATG TCG GTG CCT GCG GAA CGC GAA GAC TGG GCG        3678
Arg Ile Arg Val Val Met Ser Val Pro Ala Glu Arg Glu Asp Trp Ala
        1000            1005            1010

CGC ACC CAT CGC GAC CTC ATT GCC GGA GAA ATC TTG GCT ACC GAC TTC        3726
Arg Thr His Arg Asp Leu Ile Ala Gly Glu Ile Leu Ala Thr Asp Phe
    1015            1020            1025

GAA TTC GCC GAC CTC GCC GAT GGT GTG GCC ATC GGC GAC GCG TGC GGG        3774
Glu Phe Ala Asp Leu Ala Asp Gly Val Ala Ile Gly Asp Ala Cys Gly
1030            1035            1040            1045

TAAGCATCGA AAAGACCTGA GGTCGAGCTG GGCGACGAGC GTAACGTCAC GGCTGAAAAT     3834

CCGTGCCCGA CTTCGCCGTG GCGTTACGCT CGCGGCGCGG GGACCCGATC TCTAGGGCGT     3894

TGTCGCCCCA G                                                          3905
```

( 2 ) INFORMATION FOR SEQ ID NO:2:

( i ) SEQUENCE CHARACTERISTICS:
        ( A ) LENGTH: 1045 amino acids
        ( B ) TYPE: amino acid (D) TOPOLOGY: linear (ii) MOLECULE TYPE: protein (xi) SEQUENCE DESCRIPTION: SEQ ID NO:2:

```
Met Leu Gly Pro Gly Glu Thr Thr Arg Lys Xaa Thr Asp Asn Ala Tyr
 1               5                  10                      15

Pro Lys Leu Ala Gly Gly Ala Pro Asp Leu Pro Ala Leu Glu Leu Glu
            20                  25                  30

Val Leu Asp Tyr Trp Ser Arg Asp Thr Phe Arg Ala Ser Ile Ala
            35                  40                  45

Arg Arg Asp Gly Ala Pro Glu Tyr Val Phe Tyr Asp Gly Pro Pro Phe
        50                  55                  60

Ala Asn Gly Leu Pro His Tyr Gly His Leu Leu Thr Gly Tyr Val Lys
 65                 70                  75                      80

Asp Ile Val Pro Arg Tyr Arg Thr Met Arg Gly Tyr Lys Val Glu Arg
                85                  90                  95

Arg Phe Gly Trp Asp Thr His Gly Leu Pro Ala Glu Leu Glu Val Glu
            100                 105                 110

Arg Gln Leu Gly Ile Thr Asp Lys Ser Gln Ile Glu Ala Met Gly Ile
            115                 120                 125

Ala Ala Phe Asn Asp Ala Cys Arg Ala Ser Val Leu Arg Tyr Thr Asp
    130                 135                 140

Glu Trp Gln Ala Tyr Val Thr Arg Gln Ala Arg Trp Val Asp Phe Asp
145                 150                 155                 160

Asn Asp Tyr Lys Thr Leu Asp Leu Ala Tyr Met Glu Ser Val Ile Trp
                165                 170                 175

Ala Phe Lys Gln Leu Trp Asp Lys Gly Leu Ala Tyr Glu Gly Tyr Arg
            180                 185                 190

Val Leu Pro Tyr Cys Trp Arg Asp Glu Thr Pro Leu Ser Asn His Glu
            195                 200                 205

Leu Arg Met Asp Asp Asp Val Tyr Gln Ser Arg Gln Asp Pro Ala Val
210                 215                 220

Thr Val Gly Phe Lys Val Val Gly Gly Gln Pro Asp Asn Gly Leu Asp
225                 230                 235                 240

Gly Ala Tyr Leu Leu Val Trp Thr Thr Thr Pro Trp Thr Leu Pro Ser
                245                 250                 255

Asn Leu Ala Val Ala Val Ser Pro Asp Ile Thr Tyr Val Gln Val Gln
            260                 265                 270

Ala Gly Asp Arg Arg Phe Val Leu Ala Glu Ala Arg Leu Ala Arg Tyr
            275                 280                 285

Ala Arg Glu Leu Gly Glu Glu Pro Val Val Leu Gly Thr Tyr Arg Gly
    290                 295                 300

Ala Glu Leu Leu Gly Thr Arg Tyr Leu Pro Pro Phe Ala Tyr Phe Met
305                 310                 315                 320

Asp Trp Pro Asn Ala Phe Gln Val Leu Ala Gly Asp Phe Val Thr Thr
                325                 330                 335

Asp Asp Gly Thr Gly Ile Val His Met Ala Pro Ala Tyr Gly Glu Asp
            340                 345                 350

Asp Met Val Val Ala Glu Ala Val Gly Ile Ala Pro Val Thr Pro Val
    355                 360                 365

Asp Ser Lys Gly Arg Phe Asp Val Thr Val Ala Asp Tyr Gln Gly Gln
    370                 375                 380

His Val Phe Asp Ala Asn Ala Gln Ile Val Arg Asp Leu Lys Thr Gln
385                 390                 395                 400
```

| | | | | | | | | | | | | | |
|---|---|---|---|---|---|---|---|---|---|---|---|---|---|
| Ser | Gly | Pro | Ala | Ala | Val | Asn | Gly | Pro | Val | Leu | Ile | Arg | His | Glu | Thr |
| | | | | 405 | | | | 410 | | | | | 415 |
| Tyr | Glu | His | Pro | Tyr | Pro | His | Cys | Trp | Arg | Cys | Arg | Asn | Pro | Leu | Ile |
| | | | 420 | | | | 425 | | | | | 430 |
| Tyr | Arg | Ser | Val | Ser | Ser | Trp | Phe | Val | Arg | Val | Thr | Asp | Phe | Arg | Asp |
| | | 435 | | | | 440 | | | | 445 |
| Arg | Met | Val | Glu | Leu | Asn | Gln | Gln | Ile | Thr | Trp | Tyr | Pro | Glu | His | Val |
| | 450 | | | | 455 | | | | | 460 |
| Lys | Asp | Gly | Gln | Phe | Gly | Lys | Trp | Leu | Gln | Gly | Ala | Arg | Asp | Trp | Ser |
| 465 | | | | 470 | | | | 475 | | | | | 480 |
| Ile | Ser | Arg | Asn | Arg | Tyr | Trp | Gly | Thr | Pro | Ile | Pro | Val | Trp | Lys | Ser |
| | | | 485 | | | | 490 | | | | | 495 |
| Asp | Asp | Pro | Ala | Tyr | Pro | Arg | Ile | Asp | Val | Tyr | Gly | Ser | Leu | Asp | Glu |
| | | | 500 | | | | 505 | | | | | 510 |
| Leu | Glu | Arg | Asp | Phe | Gly | Val | Arg | Pro | Ala | Asn | Leu | His | Arg | Pro | Tyr |
| | | 515 | | | | 520 | | | | | 525 |
| Ile | Asp | Glu | Leu | Thr | Arg | Pro | Asn | Pro | Asp | Asp | Pro | Thr | Gly | Arg | Ser |
| | 530 | | | | 535 | | | | | 540 |
| Thr | Met | Arg | Arg | Ile | Pro | Asp | Val | Leu | Asp | Val | Trp | Phe | Asp | Ser | Gly |
| 545 | | | | 550 | | | | 555 | | | | | 560 |
| Ser | Met | Pro | Tyr | Ala | Gln | Val | His | Tyr | Pro | Phe | Glu | Asn | Leu | Asp | Trp |
| | | | 565 | | | | 570 | | | | | 575 |
| Phe | Gln | Gly | His | Tyr | Pro | Gly | Asp | Phe | Ile | Val | Glu | Tyr | Ile | Gly | Gln |
| | | | 580 | | | | 585 | | | | | 590 |
| Thr | Arg | Gly | Trp | Phe | Tyr | Thr | Leu | His | Val | Leu | Ala | Thr | Ala | Leu | Phe |
| | | 595 | | | | 600 | | | | 605 |
| Asp | Arg | Pro | Ala | Phe | Lys | Thr | Cys | Val | Ala | His | Gly | Ile | Val | Leu | Gly |
| | 610 | | | | 615 | | | | | 620 |
| Phe | Asp | Gly | Gln | Lys | Met | Ser | Lys | Ser | Val | Arg | Asn | Tyr | Pro | Asp | Val |
| 625 | | | | 630 | | | | 635 | | | | | 640 |
| Thr | Glu | Val | Phe | Asp | Arg | Asp | Gly | Ser | Asp | Ala | Met | Arg | Trp | Phe | Leu |
| | | | 645 | | | | 650 | | | | | 655 |
| Met | Ala | Ser | Pro | Ile | Leu | Arg | Gly | Gly | Asn | Leu | Ile | Val | Thr | Glu | Gln |
| | | | 660 | | | | 665 | | | | | 670 |
| Gly | Ile | Arg | Asp | Gly | Val | Arg | Gln | Val | Leu | Leu | Pro | Leu | Trp | Asn | Thr |
| | | 675 | | | | 680 | | | | 685 |
| Tyr | Ser | Phe | Leu | Ala | Leu | Tyr | Ala | Pro | Lys | Val | Gly | Thr | Trp | Arg | Val |
| | 690 | | | | 695 | | | | | 700 |
| Asp | Ser | Val | His | Val | Leu | Asp | Arg | Tyr | Ile | Leu | Ala | Lys | Leu | Ala | Val |
| 705 | | | | 710 | | | | 715 | | | | | 720 |
| Leu | Arg | Asp | Asp | Leu | Ser | Glu | Ser | Met | Glu | Val | Tyr | Asp | Ile | Pro | Gly |
| | | | 725 | | | | 730 | | | | | 735 |
| Ala | Cys | Glu | His | Leu | Arg | Gln | Phe | Thr | Glu | Ala | Leu | Thr | Asn | Trp | Tyr |
| | | | 740 | | | | 745 | | | | | 750 |
| Val | Arg | Arg | Ser | Arg | Ser | Arg | Phe | Trp | Ala | Glu | Asp | Ala | Asp | Ala | Ile |
| | | 755 | | | | 760 | | | | 765 |
| Asp | Thr | Leu | His | Thr | Val | Leu | Glu | Val | Thr | Thr | Arg | Leu | Ala | Ala | Pro |
| | 770 | | | | 775 | | | | | 780 |
| Leu | Leu | Pro | Leu | Ile | Thr | Glu | Ile | Ile | Trp | Arg | Gly | Leu | Thr | Arg | Glu |
| 785 | | | | 790 | | | | 795 | | | | | 800 |
| Arg | Ser | Val | His | Leu | Thr | Asp | Trp | Pro | Ala | Pro | Asp | Leu | Leu | Pro | Ser |
| | | | 805 | | | | 810 | | | | | 815 |
| Asp | Ala | Asp | Leu | Val | Ala | Ala | Met | Asp | Gln | Val | Arg | Asp | Val | Cys | Ser |

|  |  |  |  |  |  |  |  |  |  |  |  |  |  |
|---|---|---|---|---|---|---|---|---|---|---|---|---|---|
|  |  |  | 820 |  |  |  | 825 |  |  |  | 830 |  |  |
| Ala | Ala | Ser | Ser | Xaa | Arg | Lys | Ala | Lys | Lys | Leu | Arg | Val | Arg | Leu | Pro |
|  |  | 835 |  |  |  | 840 |  |  |  | 845 |
| Leu | Pro | Lys | Leu | Ile | Val | Ala | Val | Glu | Asn | Pro | Gln | Leu | Leu | Arg | Pro |
|  | 850 |  |  |  | 855 |  |  |  | 860 |
| Phe | Val | Asp | Leu | Ile | Gly | Asp | Glu | Leu | Asn | Val | Lys | Gln | Val | Glu | Leu |
| 865 |  |  |  | 870 |  |  |  | 875 |  |  |  | 880 |
| Thr | Asp | Ala | Ile | Asp | Thr | Tyr | Gly | Arg | Phe | Glu | Leu | Thr | Val | Asn | Ala |
|  |  |  | 885 |  |  |  | 890 |  |  |  | 895 |
| Arg | Val | Ala | Gly | Pro | Arg | Leu | Gly | Lys | Asp | Val | Gln | Ala | Ala | Ile | Lys |
|  |  |  | 900 |  |  |  | 905 |  |  |  | 910 |
| Ala | Val | Lys | Ala | Gly | Asp | Gly | Val | Ile | Asn | Pro | Asp | Gly | Thr | Leu | Leu |
|  |  | 915 |  |  |  | 920 |  |  |  | 925 |
| Ala | Gly | Pro | Ala | Val | Leu | Thr | Pro | Asp | Glu | Tyr | Asn | Ser | Arg | Leu | Val |
|  | 930 |  |  |  | 935 |  |  |  | 940 |
| Ala | Ala | Asp | Pro | Glu | Ser | Thr | Ala | Ala | Leu | Pro | Asp | Gly | Ala | Gly | Leu |
| 945 |  |  |  | 950 |  |  |  | 955 |  |  |  | 960 |
| Val | Val | Leu | Asp | Gly | Thr | Val | Thr | Ala | Glu | Leu | Glu | Ala | Glu | Gly | Trp |
|  |  |  | 965 |  |  |  | 970 |  |  |  | 975 |
| Ala | Lys | Asp | Pro | Ile | Arg | Glu | Leu | Gln | Glu | Leu | Arg | Lys | Ser | Thr | Gly |
|  |  |  | 980 |  |  |  | 985 |  |  |  | 990 |
| Leu | Asp | Val | Ser | Asp | Arg | Ile | Arg | Val | Val | Met | Ser | Val | Pro | Ala | Glu |
|  |  | 995 |  |  |  | 1000 |  |  |  | 1005 |
| Arg | Glu | Asp | Trp | Ala | Arg | Thr | His | Arg | Asp | Leu | Ile | Ala | Gly | Glu | Ile |
|  | 1010 |  |  |  | 1015 |  |  |  | 1020 |
| Leu | Ala | Thr | Asp | Phe | Glu | Phe | Ala | Asp | Leu | Ala | Asp | Gly | Val | Ala | Ile |
| 1025 |  |  |  | 1030 |  |  |  | 1035 |  |  |  | 1040 |
| Gly | Asp | Ala | Cys | Gly |
|  |  |  | 1045 |

( 2 ) INFORMATION FOR SEQ ID NO:3:

( i ) SEQUENCE CHARACTERISTICS:
        ( A ) LENGTH: 1487 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
GGGTGGGATT GCCACGGGCT GCCCGCCGAA CTCGAGGTCG AGCGCCCATG GGCATCACC    60
GACAAATCGC AGATCGACGC CATGGGGATC GCCGCGTTCA ACGATGCCTG CCGGGCTTCG   120
GTGTTGCGCT ACACCGGCGA GTGGCAGGCA TATGTGACCC GCCAAGCTCG CTGGGTCGAT   180
TTCGACAACG ACTACAAGAC GCTCGATCTG TCGTATATGG AATCGGTGAT CTGGGCGTTC   240
AAACAACTCT GGGACAAGGG CCTGGCATAC GAGGGATACC GGGTGCTGCC CTACCTNGTG   300
GCGCGACGAA ACCCCGCTAT CCAATCACGA ACTGCGNATG GACGACGACG TCTACCAGAG   360
CCGTCAGGAC CCGCTATCAC GGTGGGATTC AAAGTAGCGG GTGGCCAACC ACTTGAAGAG   420
CTGGCCGGCG CATTCCTGTT GGTGTGGACG ACGACACCGT GGACGCTGCC GTCAAACCTG   480
GCCGTCGCGG TAAACCCCGA GACGACATAT GTACAGATCA AAGCCGGCGA TCGGCGCTTT   540
GTGCTGGCCG AGGCAAGGGT GCCTGCCTAC GCTCGAGAGT TCGGAGAAGA ACCCGAGGTT   600
CTCGGTACCT ATCGCGGCGC CGACCTACTG GATATTCGGT ACCAACCGCC CTTTACATAC   660
TTTAGGGATT CGCAGAACGC ATTTCGCGTA CTGTCAGGCG ATTTCGTCAC CACCGAAGAC   720
```

```
GGTACCGGCA TCGTACATAT GGCCCCGGCG TACGGCGAAG ACGACATGGC GGTCGCGGAG      780

GCTGCCGGCA TCGCGCCGGT GACTCCGGTC GATGCCAAGG GCCGCTTCGA CGCCACCGTC      840

GCCGATTACC AGGGGCAGCA CGTGTTCGAC GCCAATGCCC AGATCATCCA TGACCTGAAG      900

AAACAAAGTG GTCCGGCGGC GGCNGAACGG CGCGGTGTTG ATCCGCCACG AATCCTACGA      960

ACACCCTTAC CCACATTGCT GGCGCTGCCG TAACCCGTTG ATCTACCGTG CGGTGTCGTC     1020

CTGGTTCGTC ACGGTGACGG AATTCCGCGA GCGCATGGTC GAACTCAACC AGCAGATCAC     1080

CTGGTATCCC GAGCACGTCA AGGACGGCCA GTTCGGAAAG TGGCTGCAGG GTGCCCGCGA     1140

TTGGTCCATC TCACGAAACC GCTACTGGGG CACCCCGATT CCGGTGTGGA AGTCCGATGA     1200

TCCCTCCTAT CCGAGAATCG ATGTGTACGG CAGCTTGGAC GAGCTGGAAC GCGATTTCGG     1260

GGTCCGGCCG GACAACTTGC ACCGGCCCTA CATCGACGAG CTGACCCGGC CCAACCCCGA     1320

CGATCCCACC GGGGAAAGCA CGATGCGGCG CATCCCCGAC GTGCTCGACG TGTGGTTCGA     1380

CTCGGGCTCC ATGCCCTACG CCCAGGTGCA CTACCCATTC GAAAACCGTG GCTGGTTCGA     1440

CGGGGTCGAT TGCGCCGATC CGGACCAACG GGTCGACGCC CACTATC                   1487
```

( 2 ) INFORMATION FOR SEQ ID NO:4:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: other nucleic acid ( i x ) FEATURE:
    ( A ) NAME/KEY: modified_base
    ( B ) LOCATION: 11
    ( D ) OTHER INFORMATION: /mod_base=i ( i x ) FEATURE:
    ( A ) NAME/KEY: modified_base
    ( B ) LOCATION: 20
    ( D ) OTHER INFORMATION: /mod_base=i ( i x ) FEATURE:
    ( A ) NAME/KEY: modified_base
    ( B ) LOCATION: 26
    ( D ) OTHER INFORMATION: /mod_base=i ( i x ) FEATURE:
    ( A ) NAME/KEY: modified_base
    ( B ) LOCATION: 29
    ( D ) OTHER INFORMATION: /mod_base=i ( x i ) SEQUENCE DESCRIPTION: SEQ ID NO:4:

```
GCGAATTCGG NTGGGAYACN CAYGGNSTNC C                                      31
```

( 2 ) INFORMATION FOR SEQ ID NO:5:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 11
    ( D ) OTHER INFORMATION: /mod_base=i ( i x ) FEATURE:
    ( A ) NAME/KEY: modified_base
    ( B ) LOCATION: 26
    ( D ) OTHER INFORMATION: /mod_base=i ( i x ) FEATURE:
        ( A ) NAME/KEY: modified_base
        ( B ) LOCATION: 29
        ( D ) OTHER INFORMATION: /mod_base=i ( x i ) SEQUENCE DESCRIPTION: SEQ ID NO:5:

GCGAATTCGG NTGGGAYTGY CAYGGNCTNC C     31

( 2 ) INFORMATION FOR SEQ ID NO:6:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 12
        ( D ) OTHER INFORMATION: /mod_base=i ( i x ) FEATURE:
        ( A ) NAME/KEY: modified_base
        ( B ) LOCATION: 15
        ( D ) OTHER INFORMATION: /mod_base=i ( i x ) FEATURE:
        ( A ) NAME/KEY: modified_base
        ( B ) LOCATION: 24
        ( D ) OTHER INFORMATION: /mod_base=i ( i x ) FEATURE:
        ( A ) NAME/KEY: modified_base
        ( B ) LOCATION: 27
        ( D ) OTHER INFORMATION: /mod_base=i ( x i ) SEQUENCE DESCRIPTION: SEQ ID NO:6:

TWYATGGART CNACNTGGTG GGYNTTNAAR CA    32

( 2 ) INFORMATION FOR SEQ ID NO:7:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=i ( i x ) FEATURE:
        ( A ) NAME/KEY: modified_base
        ( B ) LOCATION: 16
        ( D ) OTHER INFORMATION: /mod_base=i ( i x ) FEATURE:
        ( A ) NAME/KEY: modified_base
        ( B ) LOCATION: 25
        ( D ) OTHER INFORMATION: /mod_base=i ( i x ) FEATURE:
        ( A ) NAME/KEY: modified_base
        ( B ) LOCATION: 28
        ( D ) OTHER INFORMATION: /mod_base=i ( i x ) FEATURE:
        ( A ) NAME/KEY: modified_base
        ( B ) LOCATION: 31
        ( D ) OTHER INFORMATION: /mod_base=i ( x i ) SEQUENCE DESCRIPTION: SEQ ID NO:7:

GCGAATTCGN CARCGNTAYT GGGGNRTNCC NAT    33

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=i ( i x ) FEATURE:
        ( A ) NAME/KEY: modified_base
        ( B ) LOCATION: 16
        ( D ) OTHER INFORMATION: /mod_base=i ( i x ) FEATURE:
        ( A ) NAME/KEY: modified_base
        ( B ) LOCATION: 25
        ( D ) OTHER INFORMATION: /mod_base=i ( i x ) FEATURE:
        ( A ) NAME/KEY: modified_base
        ( B ) LOCATION: 28
        ( D ) OTHER INFORMATION: /mod_base=i ( i x ) FEATURE:
        ( A ) NAME/KEY: modified_base
        ( B ) LOCATION: 31
        ( D ) OTHER INFORMATION: /mod_base=i ( x i ) SEQUENCE DESCRIPTION: SEQ ID NO:8:

```
GCGAATTCGN AAYCGNTWYT GGGGNACNCC NMT                                    33
```

( 2 ) INFORMATION FOR SEQ ID NO:9:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 15
        ( D ) OTHER INFORMATION: /mod_base=i ( i x ) FEATURE:
        ( A ) NAME/KEY: modified_base
        ( B ) LOCATION: 18
        ( D ) OTHER INFORMATION: /mod_base=i ( i x ) FEATURE:
        ( A ) NAME/KEY: modified_base
        ( B ) LOCATION: 21
        ( D ) OTHER INFORMATION: /mod_base=i ( i x ) FEATURE:
        ( A ) NAME/KEY: modified_base
        ( B ) LOCATION: 30
        ( D ) OTHER INFORMATION: /mod_base=i ( i x ) FEATURE:
        ( A ) NAME/KEY: modified_base
        ( B ) LOCATION: 33
        ( D ) OTHER INFORMATION: /mod_base=i ( x i ) SEQUENCE DESCRIPTION: SEQ ID NO:9:

```
GCGAATTCRA ACCANCCNCG NGTYTGRTCN WWNCCYTC                               38
```

( 2 ) INFORMATION FOR SEQ ID NO:10:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i x ) FEATURE:
  ( A ) NAME/KEY: modified_base
  ( B ) LOCATION: 3
  ( D ) OTHER INFORMATION: /mod_base=i ( i x ) FEATURE:
  ( A ) NAME/KEY: modified_base
  ( B ) LOCATION: 6
  ( D ) OTHER INFORMATION: /mod_base=i ( i x ) FEATURE:
  ( A ) NAME/KEY: modified_base
  ( B ) LOCATION: 12
  ( D ) OTHER INFORMATION: /mod_base=i ( i x ) FEATURE:
  ( A ) NAME/KEY: modified_base
  ( B ) LOCATION: 15
  ( D ) OTHER INFORMATION: /mod_base=i ( i x ) FEATURE:
  ( A ) NAME/KEY: modified_base
  ( B ) LOCATION: 18
  ( D ) OTHER INFORMATION: /mod_base=i ( i x ) FEATURE:
  ( A ) NAME/KEY: modified_base
  ( B ) LOCATION: 21
  ( D ) OTHER INFORMATION: /mod_base=i ( x i ) SEQUENCE DESCRIPTION: SEQ ID NO:10:

GGNARNGTCC ANGGNGTNGT NGTCCA      26

( 2 ) INFORMATION FOR SEQ ID NO:11:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

TCACCGACAA ATCGCAGATC GACGCCAT      28

( 2 ) INFORMATION FOR SEQ ID NO:12:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

GGATCGGCGC AATCGACCCC GT      22

( 2 ) INFORMATION FOR SEQ ID NO:13:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

AATGCGCCGG CCAGCTCTTC AA      22

( 2 ) INFORMATION FOR SEQ ID NO:14:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GGCGTACGGC GAAGACGACA TGGCGG　　　　　　　　　　　　　　　　　　　　　　　　　　26

( 2 ) INFORMATION FOR SEQ ID NO:15:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

AATTCGAGCC GTACGCGGG　　　　　　　　　　　　　　　　　　　　　　　　　　　　　19

( 2 ) INFORMATION FOR SEQ ID NO:16:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GATCCCCGCG TACGGCTCG　　　　　　　　　　　　　　　　　　　　　　　　　　　　　19

( 2 ) INFORMATION FOR SEQ ID NO:17:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

AATTCGAACT AGTTCCCGGG CGTACGGTTT AAACGCGGCC GCGG　　　　　　　　　　　　　　44

( 2 ) INFORMATION FOR SEQ ID NO:18:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GATCCCGCGG CCGCGTTTAA ACCGTACGCC CGGGAACTAG TTCG　　　　　　　　　　　　　　44

( 2 ) INFORMATION FOR SEQ ID NO:19:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

ATAAGAATGC GGCCGCAGAT CTTATGACCG ATAACGCATA TCCAA　　　　　　　　　　　　　45

( 2 ) INFORMATION FOR SEQ ID NO:20:

( i ) SEQUENCE CHARACTERISTICS:
: ( A ) LENGTH: 8 amino acids
: ( B ) TYPE: amino acid
: ( C ) STRANDEDNESS: unknown
: ( D ) TOPOLOGY: linear ( i i ) MOLECULE TYPE: peptide ( x i ) SEQUENCE DESCRIPTION: SEQ ID NO:20:

Gly Trp Asp Thr His Gly Xaa Pro
1               5

( 2 ) INFORMATION FOR SEQ ID NO:21:

( i ) SEQUENCE CHARACTERISTICS:
: ( A ) LENGTH: 8 amino acids
: ( B ) TYPE: amino acid
: ( C ) STRANDEDNESS:
: ( D ) TOPOLOGY: linear ( i i ) MOLECULE TYPE: peptide ( x i ) SEQUENCE DESCRIPTION: SEQ ID NO:21:

Gly Trp Asp Cys His Gly Xaa Pro
1               5

( 2 ) INFORMATION FOR SEQ ID NO:22:

( i ) SEQUENCE CHARACTERISTICS:
: ( A ) LENGTH: 11 amino acids
: ( B ) TYPE: amino acid
: ( C ) STRANDEDNESS:
: ( D ) TOPOLOGY: linear ( i i ) MOLECULE TYPE: peptide ( x i ) SEQUENCE DESCRIPTION: SEQ ID NO:22:

Xaa Xaa Glu Ser Xaa Trp Trp Xaa Xaa Lys Gln
1               5                       10

( 2 ) INFORMATION FOR SEQ ID NO:23:

( i ) SEQUENCE CHARACTERISTICS:
: ( A ) LENGTH: 9 amino acids
: ( B ) TYPE: amino acid
: ( C ) STRANDEDNESS:
: ( D ) TOPOLOGY: linear ( i i ) MOLECULE TYPE: peptide ( x i ) SEQUENCE DESCRIPTION: SEQ ID NO:23:

Arg Gln Arg Xaa Trp Gly Xaa Pro Xaa
1               5

( 2 ) INFORMATION FOR SEQ ID NO:24:

( i ) SEQUENCE CHARACTERISTICS:
: ( A ) LENGTH: 9 amino acids
: ( B ) TYPE: amino acid
: ( C ) STRANDEDNESS:
: ( D ) TOPOLOGY: linear ( i i ) MOLECULE TYPE: peptide ( x i ) SEQUENCE DESCRIPTION: SEQ ID NO:24:

Arg Xaa Arg Xaa Trp Gly Xaa Pro Xaa
1               5

( 2 ) INFORMATION FOR SEQ ID NO:25:

(i) SEQUENCE CHARACTERISTICS:
    (A) LENGTH: 10 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:25:

Glu Gly Xaa Asp Gln Xaa Arg Gly Trp Phe
1               5                   10

(2) INFORMATION FOR SEQ ID NO:26:

(i) SEQUENCE CHARACTERISTICS:
    (A) LENGTH: 9 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:26:

Trp Thr Thr Thr Pro Trp Thr Leu Pro
1               5

(2) INFORMATION FOR SEQ ID NO:27:

(i) SEQUENCE CHARACTERISTICS:
    (A) LENGTH: 44 base pairs
    (B) TYPE: nucleic acid
    (C) STRANDEDNESS: single
    (D) TOPOLOGY: linear (xi) SEQUENCE DESCRIPTION: SEQ ID NO:27:

ATAAGAATGC GGCCGCAGAT CTATGACCGA TAACGCATAT CCAA    44